US012597503B2

(12) United States Patent
Nielsen et al.

(10) Patent No.: US 12,597,503 B2
(45) Date of Patent: Apr. 7, 2026

(54) MEDICAL VISUALIZATION DEVICES AND SYSTEMS

(71) Applicant: AMBU A/S, Ballerup (DK)

(72) Inventors: Brian Nielsen, Næstved (DK); Kasper Rieland Jakobsen, Roskilde (DK); Chun-Chieh Chen, Rødovre (DK)

(73) Assignee: AMBU A/S, Ballerup (DK)

( * ) Notice: Subject to any disclaimer, the term of this patent is extended or adjusted under 35 U.S.C. 154(b) by 110 days.

(21) Appl. No.: 18/240,847

(22) Filed: Aug. 31, 2023

(65) Prior Publication Data

US 2023/0410983 A1 Dec. 21, 2023

Related U.S. Application Data

(63) Continuation-in-part of application No. 18/277,312, filed on Aug. 15, 2023, and a continuation-in-part of (Continued)

(30) Foreign Application Priority Data

Mar. 5, 2021 (DK) ............................ PA 2021 70098
Mar. 5, 2021 (DK) ............................ PA 2021 70099

(Continued)

(51) Int. Cl.
*G16H 30/20* (2018.01)
*G06T 1/00* (2006.01)

(52) U.S. Cl.
CPC ........... *G16H 30/20* (2018.01); *G06T 1/0007* (2013.01); *G06T 2210/41* (2013.01)

(58) Field of Classification Search
CPC ........ G16H 30/20; G16H 30/40; G16H 40/40; G16H 40/63; G06T 1/0007; G06T 2210/41; A61B 1/00016; A61B 1/00124

(Continued)

(56) References Cited

U.S. PATENT DOCUMENTS 4,646,721 A 3/1987 Arakawa
5,940,126 A 8/1999 Kimura
(Continued)

FOREIGN PATENT DOCUMENTS

CN 103188987 A 7/2013
EP 1827258 B1 10/2011
(Continued)

OTHER PUBLICATIONS

Corrected International Search Report received for PCT/EP2022/055134, mailed Jul. 26, 2022, 5 pages., Jul. 26, 2022.

(Continued)

*Primary Examiner* — Prabodh M Dharia
(74) *Attorney, Agent, or Firm* — Faegre Drinker Biddle & Reath LLP

(57) ABSTRACT

A medical visualisation system including a main component including an image sensor and a light emitter; a first auxiliary component configured to transmit image data based on the signals; a second auxiliary component configured to receive signals from the main component and to transmit image data based on the signals, the second auxiliary component including a second memory having embedded therein data; and a video processing apparatus including a high frequency wireless transceiver configured to establish an image data communication channel with the high frequency wireless transceiver of the first auxiliary component or with the high frequency wireless transceiver of the second auxiliary component and to receive the image data with the image data communication channel, wherein the first auxiliary component is configured to, based on the data, cause adjustment of one or more components of the main component or the video processing apparatus.

20 Claims, 26 Drawing Sheets

Related U.S. Application Data application No. 18/277,303, filed on Aug. 15, 2023, and a continuation-in-part of application No. 18/276,866, filed on Aug. 10, 2023, and a continuation-in-part of application No. 18/276,861, filed on Aug. 10, 2023, and a continuation-in-part of application No. 18/276,868, filed as application No. PCT/EP2022/055134, filed as application No. PCT/EP2022/055136, filed as application No. PCT/EP2022/055139, filed as application No. PCT/EP2022/055135, filed as application No. PCT/EP2022/055133 on Mar. 1, 2022.

(30) Foreign Application Priority Data

| Mar. 5, 2021 | (DK) | ............................ | PA 2021 70100 |
| Mar. 5, 2021 | (DK) | ............................ | PA 2021 70101 |
| Mar. 5, 2021 | (DK) | ............................ | PA 2021 70102 |

(58) Field of Classification Search
USPC ......................................................... 345/418
See application file for complete search history.

(56) References Cited

U.S. PATENT DOCUMENTS

| 6,106,457 | A | 8/2000 | Perkins et al. | |
| 6,796,939 | B1 | 9/2004 | Hirata et al. | |
| 7,520,853 | B2 | 4/2009 | Amling et al. | |
| 7,753,842 | B2 | 7/2010 | Glukhovsky et al. | |
| 8,194,121 | B2 | 6/2012 | Blumzvig et al. | |
| 8,194,122 | B2 | 6/2012 | Amling et al. | |
| 8,465,421 | B2 | 6/2013 | Finkman et al. | |
| 8,599,250 | B2 | 12/2013 | Amling et al. | |
| 8,723,936 | B2 | 5/2014 | Amling et al. | |
| 9,007,450 | B2 | 4/2015 | Amling et al. | |
| 9,030,544 | B2 | 5/2015 | Tashiro et al. | |
| 9,033,870 | B2 | 5/2015 | Farr et al. | |
| 9,179,831 | B2 | 11/2015 | Mcgrail et al. | |
| 9,386,914 | B2 | 7/2016 | Birnkrant et al. | |
| 9,861,334 | B2 | 1/2018 | Tajima et al. | |
| 11,265,450 | B2 | 3/2022 | Katsuki | |
| 2003/0195390 | A1 | 10/2003 | Graumann | |
| 2003/0228553 | A1 | 12/2003 | Mandelkern et al. | |
| 2004/0243448 | A1 | 12/2004 | Shoji et al. | |
| 2006/0116667 | A1* | 6/2006 | Hamel | A61B 50/13 606/1 |
| 2007/0162095 | A1 | 7/2007 | Kimmel et al. | |
| 2007/0195539 | A1 | 8/2007 | Dashiell | |
| 2008/0139881 | A1 | 6/2008 | Cover et al. | |
| 2008/0214896 | A1 | 9/2008 | Krupa et al. | |
| 2009/0076331 | A1 | 3/2009 | Konwitz et al. | |
| 2009/0247824 | A1 | 10/2009 | Kawasaki et al. | |
| 2009/0270679 | A1 | 10/2009 | Hoeg et al. | |
| 2009/0318758 | A1 | 12/2009 | Farr et al. | |
| 2010/0014174 | A1 | 1/2010 | Togino | |
| 2010/0097453 | A1 | 4/2010 | Endo et al. | |
| 2010/0141744 | A1 | 6/2010 | Amling et al. | |
| 2010/0208054 | A1 | 8/2010 | Farr | |
| 2011/0222746 | A1 | 9/2011 | Kotula et al. | |
| 2011/0243116 | A1 | 10/2011 | Endo et al. | |
| 2012/0134410 | A1 | 5/2012 | Kawasaki et al. | |
| 2012/0162472 | A1 | 6/2012 | Amling et al. | |
| 2012/0209071 | A1 | 8/2012 | Bayer et al. | |
| 2012/0246374 | A1 | 9/2012 | Fino | |
| 2012/0289858 | A1 | 11/2012 | Ouyang et al. | |
| 2013/0092173 | A1 | 4/2013 | Alexander et al. | |
| 2013/0103907 | A1 | 4/2013 | Katori et al. | |
| 2013/0204085 | A1 | 8/2013 | Alexander et al. | |
| 2014/0135576 | A1 | 5/2014 | Hebert | |
| 2014/0275763 | A1 | 9/2014 | King et al. | |
| 2015/0035967 | A1 | 2/2015 | Wodnicki et al. | |
| 2015/0293877 | A1 | 10/2015 | Liang et al. | |
| 2016/0000300 | A1* | 1/2016 | Williams | A61B 1/05 600/109 |

| 2016/0066770 | A1 | 3/2016 | Barbato et al. | |
| 2016/0073855 | A1 | 3/2016 | Farr et al. | |
| 2016/0213236 | A1 | 7/2016 | Hruska et al. | |
| 2016/0299629 | A1* | 10/2016 | Doyle | G02F 1/13338 |
| 2016/0344992 | A1* | 11/2016 | D'Alfonso | A61B 1/0669 |
| 2017/0095297 | A1 | 4/2017 | Richmond et al. | |
| 2017/0209027 | A1 | 7/2017 | Raj et al. | |
| 2017/0280988 | A1 | 10/2017 | Barbato et al. | |
| 2017/0311777 | A1 | 11/2017 | Hirayama et al. | |
| 2018/0084986 | A1 | 3/2018 | Ochi et al. | |
| 2018/0220873 | A1 | 8/2018 | Tani | |
| 2018/0296067 | A1 | 10/2018 | Amling et al. | |
| 2019/0052560 | A1 | 2/2019 | Smith | |
| 2019/0104922 | A1 | 4/2019 | Kasumi | |
| 2019/0133430 | A1 | 5/2019 | Inglis et al. | |
| 2019/0142256 | A1 | 5/2019 | Zhao et al. | |
| 2019/0261844 | A1 | 8/2019 | Walker et al. | |
| 2019/0313881 | A1 | 10/2019 | Francher | |
| 2019/0320879 | A1 | 10/2019 | Langell et al. | |
| 2019/0335987 | A1 | 11/2019 | Cook | |
| 2019/0350438 | A1 | 11/2019 | Masuno et al. | |
| 2020/0113412 | A1 | 4/2020 | Jensen | |
| 2020/0273575 | A1 | 8/2020 | Wolf et al. | |
| 2020/0287899 | A1* | 9/2020 | Koizumi | A61B 1/00 |
| 2020/0305684 | A1 | 10/2020 | Hagihara | |
| 2020/0405124 | A1 | 12/2020 | Sonnenborg et al. | |
| 2021/0105467 | A1 | 4/2021 | Tani | |
| 2021/0113059 | A1 | 4/2021 | Kasumi | |
| 2021/0266435 | A1 | 8/2021 | Katsuki | |
| 2021/0338040 | A1 | 11/2021 | Michihata et al. | |
| 2021/0358086 | A1* | 11/2021 | Jørgensen | G06T 5/73 |
| 2022/0039634 | A1 | 2/2022 | Williams | |
| 2022/0230643 | A1 | 7/2022 | Pai et al. | |
| 2023/0037178 | A1* | 2/2023 | Kamon | G06T 7/0012 |
| 2024/0021103 | A1 | 1/2024 | Jørgensen et al. | |
| 2024/0108207 | A1 | 4/2024 | Yazdi et al. | |

FOREIGN PATENT DOCUMENTS

| EP | 2445210 | A1 | 4/2012 |
| EP | 2286718 | B1 | 12/2013 |
| EP | 2778999 | A2 | 9/2014 |
| EP | 3417758 | A1 | 12/2018 |
| EP | 3636133 | A1 | 4/2020 |
| JP | 4918599 | B2 | 4/2012 |
| JP | 2012-090974 | A | 5/2012 |
| WO | 2008/063565 | A2 | 5/2008 |
| WO | 2015/163942 | A1 | 10/2015 |
| WO | 2019/198364 | A1 | 10/2019 |
| WO | 2019/211938 | A1 | 11/2019 |
| WO | 2020/031717 | A1 | 2/2020 |
| WO | 2020/039716 | A1 | 2/2020 |

OTHER PUBLICATIONS

Examination and Search Report for Denmark Application No. DK PA202170102, mailed on Jun. 21, 2021, 9 pages.

Examination and Search Report for Denmark Application No. PA202170098, mailed on May 18, 2021, 12 pages.

Examination and Search Report for Denmark Application No. PA202170099, mailed on Jun. 25, 2021, 8 pages.

Examination and Search Report for Denmark Application No. PA202170100, mailed on Jun. 25, 2021, 8 pages.

Examination and Search Report for Denmark Application No. PA202170101, mailed on Jun. 21, 2021, 9 pages.

International Search Report and Written Opinion received for PCT Patent Application No. PCT/EP2022/055139, mailed on Jun. 22, 2022, 14 pages.

International Search Report and Written Opinion received for PCT Patent Application No. PCT/EP2022/055133, mailed on Jun. 3, 2022, 10 pages.

International Search Report and Written Opinion received for PCT Patent Application No. PCT/EP2022/055134, mailed on Jul. 26, 2022, 14 pages.

International Search Report and Written Opinion received for PCT Patent Application No. PCT/EP2022/055135, mailed on Jun. 22, 2022, 9 pages.

(56)                    References Cited

OTHER PUBLICATIONS

International Search Report and Written Opinion received for PCT
Patent Application No. PCT/EP2022/055136, mailed on Aug. 5,
2022, 17 pages.
Office Action in related U.S. Appl. No. 18/276,868 (1155) dated
Aug. 4, 2025, 15 pages.
Office Action in related U.S. Appl. No. 18/277,303 (1158) dated
Aug. 27, 2025, 32 pages.
Office Action in related U.S. Appl. No. 18/276,861 (1157) dated
Aug. 1, 2025, 27 pages.
Office Action in related U.S. Appl. No. 18/277,312 (1159) dated
Dec. 17, 2025, 31 pages.
Office Action in related U.S. Appl. No. 18/276,866 (1156) dated Jan.
16, 2026, 26 pages.

* cited by examiner

510

MEDICAL VISUALIZATION DEVICES AND SYSTEMS

This application is a continuation-in-part of U.S. patent application Ser. No. 18/276,868, filed Aug. 10, 2023, which is a National Phase entry under 35 U.S.C. § 371 of International Application No. PCT/EP2022/055133, filed Mar. 1, 2022, which claims the benefit of and priority from Danish Patent Application No. PA 2021 70098, filed Mar. 5, 2021; is a continuation-in-part of U.S. patent application Ser. No. 18/276,866, filed Aug. 10, 2023, which is a National Phase entry under 35 U.S.C. § 371 of International Application No. PCT/EP2022/055134, filed Mar. 1, 2022, which claims the benefit of and priority from Danish Patent Application No. PA 2021 70099, filed Mar. 5, 2021; is a continuation-in-part of U.S. patent application Ser. No. 18/276,861, filed Aug. 10, 2023, which is a National Phase entry under U.S.C. § 371 of International Application No. PCT/EP2022/055135, filed Mar. 1, 2022, which claims the benefit of and priority from Danish Patent Application No. PA 2021 70100, filed Mar. 5, 2021; is a continuation-in-part of U.S. patent application Ser. No. 18/277,303, filed Aug. 15, 2023, is a National Phase entry under 35 U.S.C. § 371 of International Application No. PCT/EP2022/055136, filed Mar. 1, 2022, which claims the benefit of and priority from Danish Patent Application No. PA 2021 70101, filed March 2021; and is a continuation-in-part of U.S. patent application Ser. No. 18/277,312, filed Aug. 15, 2023, which is a National Phase entry under 35 U.S.C. § 371 of International Application No. PCT/EP2022/055139, filed Mar. 1, 2022, which claims the benefit of and priority from Danish Patent Application No. PA 2021 70102, filed Mar. 5, 2021, all the disclosures of the aforementioned applications are incorporated by reference herein in their entirety.

TECHNICAL FIELD

The present disclosure relates to a medical visualisation system and components thereof. More specifically, the medical visualisation system comprises a medical visualisation device and a video processing apparatus, wherein image data is transmitted from the medical visualisation device and the video processing apparatus.

BACKGROUND

Reusable medical visualization devices are capable of being sterilized and are very expensive relative to single-use medical visualization devices, which are discarded after, typically, a single use.

The medical visualization devices may utilize wireless communication from a medical device to a processing device. Some wireless communication techniques are known in the art. However, these technical solutions are not widespread as commercially available products, and particularly they are not widespread when it comes to single use products. There exists a vast spectrum of technical solutions providing a wireless communication link, but few fulfil the needs for medical devices at hospital settings.

For instance, not all communication frequencies may be used at hospitals and for medical devices, and in particular visualisation devices, such as endoscopes, very low latency is an important parameter. Moreover, usability, disposability and cost are driving factors defining suitable technical solutions.

SUMMARY

The present disclosure relates to a medical visualisation device and a visualisation system. The visualisation system may further comprise a video processing apparatus (VPA) to be connected to the medical visualisation device, e.g. the VPA may be configured to receive image data from the medical visualisation device.

One problem addressed by the present disclosure is how to handle medical visualisation devices when their batteries do not have enough charge to perform a procedure, particularly when a medical visualisation device comprises data that is used to configure wireless communication channels, adapt to operator or hospital preferences, modify image data, or configure an image sensor. Another problem addressed by the present disclosure is how to disinfect medical visualisation devices in a logistically efficient manner. A further problem addressed by the present disclosure is how to mitigate the cost and environmental impact of disposable devices.

The present disclosure provides solutions to the problems identified above and to the issues with prior art systems. One solution is to enable pairing of one medical visualisation device with another, to thereby initiate transfer of the relevant data. The transfer is typically from the device with depleted battery to a charged device. However, increasing the functionality of the medical visualisation device increases its cost. In a hospital setting, where many medical visualisation devices are used, one solution is to provide a handling system that can be configured to simplify, and reduce the cost, of the medical visualisation devices. Further solutions are described below.

The present disclosure provides a solution for transferring data, such as the initial data, between auxiliary components, such as to enable replacement of one auxiliary component with another auxiliary component. For example, this may be needed if an auxiliary component is running low on battery. A method and handling system for transferring the data may further cause transmittal of data from the auxiliary memory of the first auxiliary component to the auxiliary memory of the second auxiliary component. The handling system, or a portion thereof, may be referred to as a "charging station."

It is an advantage of the handling system that it reduces or avoid the need to employ buttons or similar on the auxiliary components, as the user may manage the auxiliary components through the handling system.

It is a further advantage of the handling system that in addition to facilitate transfer of data between auxiliary components, it also facilitates charging of the auxiliary component from which the data is being transferred. As the most likely scenario for wanting to transfer the data is that the currently used auxiliary component is running low on power, it is advantageous that the handling system provides both transfer of data, as well as charging of the auxiliary component from which the data is transferred. Thereby, the auxiliary component from which data is transferred may be ready at the handling system for the next time there is a need to swap an auxiliary component.

It is an object of the present disclosure to provide a medical visualisation system and components thereof to enhance flexibility and usability of the system. For example, the present disclosure provides solutions for enabling wireless transmission of video data from a medical visualisation device, such as an endoscope or a laryngoscope, to a VPA or other suitable equipment.

Accordingly, a medical visualisation system and elements thereof are disclosed. The medical visualisation system may comprise one or more or all of the elements disclosed in the following.

A medical visualisation device is disclosed. The medical visualisation system may comprise the medical visualisation device. The medical visualisation device may completely or partly be a single-use product. The medical visualisation device may be an endoscope. For example, the medical visualisation device may comprise a handle and an insertion cord extending from the handle to a distal tip. The handle may comprise a control button adapted to receive an input in a first input direction and/or in a second input direction. The touch input in the first input direction may cause a bending section of the insertion cord to bend in a first bending direction. The touch input in the second input direction may cause the bending section to bend in a second bending direction. Other examples of the medical visualisation device may be a laryngoscope or an endotracheal tube with integrated camera.

The medical visualisation device comprises an image sensor adapted to generate image data indicative of a view from the medical visualisation device and a light emitter adapted to provide illumination of the view. The view may be a view from a distal end of the visualization device. The light emitter may be an LED, an optical fibre, or similar element known to provide illumination. The medical visualisation device further comprises a device processing unit adapted to receive the image data from the image sensor and optionally encode the image data to provide encoded image data based on the image data. The device processing unit may comprise an image signal processor (ISP), a complex programmable logic device (CPLD), a field-programmable gate array (FPGA) and/or other suitable processing unit elements. The device processing unit may comprise memory, such as buffer memory.

The medical visualisation device comprises a device communication interface. For example, the medical visualisation device may comprise a device transceiver adapted to communicate with a VPA transceiver of a VPA, such as the VPA also disclosed herein. The device transceiver may be connected to the device processing unit and be configured to send data to and receive data from the VPA. The device transceiver is adapted to receive the image data and/or the encoded image data from the device processing unit and transmit the image data and/or the encoded image data using a downstream data channel to the VPA wireless communication module. The device transceiver may be adapted to transmit initial data (or non-image data) to the VPA and receive configuration data from the VPA. The device transceiver is further adapted to receive settings data using an upstream data channel from a VPA wireless communication module.

The medical visualisation system may comprise an auxiliary component couplable to a main component to form the disclosed medical visualisation device. The main component comprises the image sensor, the light emitter and a main coupling part. The main component may be a single-use product, meaning that it is not designed to survive sterilization and other aggressive cleaning. Therefore, the main component is designed to be discarded after use in a single patient, typically after a medical procedure or procedures are completed in a single operating room setting. The main component is typically in a sterile package. The sterile package is opened to perform the procedure(s) and whence the procedure(s) is completed the main component is thrown away. The main component of an endoscope may comprise an insertion cord comprising an insertion cord, a bending section and a tip part. The tip part may comprise a tip housing enclosing the image sensor and the light emitter. The main component of a video laryngoscope may comprise a flexible cord comprising, at a distal end thereof, the image sensor and the light emitter. The main component of the video laryngoscope may also comprise a blade including, at a distal end thereof, the image sensor and the light emitter.

The auxiliary component comprises an auxiliary coupling part adapted to couple with the main coupling part. The auxiliary component may comprise the device processing unit and one or more auxiliary communication interfaces. For example, the auxiliary component may comprise the device wireless communication module. The auxiliary component may be a re-usable product. Hence, the auxiliary component may be adapted to be coupled, one at a time, to a plurality of main components.

The auxiliary component or part thereof may be a dongle for insertion into a designated receiver cavity of the main component. Alternatively or additionally, the auxiliary component, or a part thereof, may be a wearable device, such as a wristwatch or an armband.

The auxiliary component may comprise memory, denoted as auxiliary memory. The auxiliary memory may store initial data. The initial data is preferably stored in the auxiliary memory prior to coupling the auxiliary component and the main component, such as prior to coupling the auxiliary coupling part and the main coupling part. The initial data may be different than and/or unrelated to the image data and may consisting of non-image data, e.g. not generated by the image sensor.

The medical visualisation system may comprise the VPA. The VPA is operable to receive image data from a medical visualisation device. The VPA comprises a first housing. The medical visualisation system may comprise a display. The VPA may comprise the display, e.g. accommodated in the first housing or couplable to the first housing, e.g. the display may be supported by the first housing or affixed to the first housing. Alternatively, the VPA may be communicatively couplable to the display. The display may be an external display. The VPA may be devoid of a display. The display, whether forming part of the VPA or not, may be a touch sensitive display.

The VPA further comprises one or more VPA communication interfaces. For example, the VPA may comprise a VPA transceiver adapted to communicate with the device transceiver of the medical visualisation device. The VPA transceiver may be adapted to receive image data and/or encoded image data using a downstream data channel from the device transceiver to the VPA wireless communication module.

The VPA further comprises a VPA controller, or VPA processor, adapted to receive the image data and/or the encoded image data from the VPA wireless communication module, optionally decode the encoded image data, and cause the display to display a live representation of the image data. The VPA controller may comprise memory, such as buffer memory.

The VPA may further comprise memory, denoted as VPA memory. The VPA memory may be connected to the VPA controller. The VPA controller may be adapted to read and/or write data from the VPA memory. The VPA memory may be any suitable electronic memory.

The VPA transceiver may further be adapted to transmit settings data using an upstream data channel from the VPA transceiver to the device wireless communication module. The VPA controller may be adapted to provide and/or generate the settings data based on the image data to adjust settings of one or more components of the medical visualisation device, such as the light emitter and/or the image sensor of the medical visualisation device.

The VPA controller may be adapted to receive the initial data from the auxiliary component and adjust one or more parameters of the medical visualisation system based on the initial data.

The present disclosure provides solutions for transferring data between auxiliary components, such as to enable replacement of one auxiliary component, e.g. storing personal and/or unique information, with another auxiliary component. For example, this may be needed if an auxiliary component is running low on battery.

A first auxiliary component and a second auxiliary component may be adapted to transmit, via respective auxiliary communication interfaces, data from the auxiliary memory of the second auxiliary component to the auxiliary memory of the first auxiliary component. The transmission may be in response to receiving one or more user inputs indicative of a user request to transmit the data from the auxiliary memory of the second auxiliary component to the auxiliary memory of the first auxiliary component. The user inputs may be received at an auxiliary user interface of the first auxiliary component and/or an auxiliary user interface of the second auxiliary component and/or at an user interface of a handling system.

Also disclosed is a method for handling auxiliary components. The method may comprise handling the auxiliary components by use of the below disclosed handling system. In one embodiment, the method comprises receiving a first auxiliary component, receiving a second auxiliary component, e.g. after receiving the first auxiliary component, and transmitting the initial data from the auxiliary memory of the second auxiliary component to the auxiliary memory of the first auxiliary component. The method may further comprise providing the first auxiliary component for retrieval after transmitting the data from the auxiliary memory of the second auxiliary component to the auxiliary memory of the first auxiliary component.

Also disclosed is a handling system used to perform the foregoing embodiment of the method for handling auxiliary components. The handling system comprises a first system communication interface adapted to couple with the auxiliary communication interface of the first auxiliary component and a second system communication interface adapted to couple with the auxiliary communication interface of the second auxiliary component. The handling system is adapted to, via the first system communication interface and/or the second system communication interface, cause transmittal of data from the auxiliary memory of the second auxiliary component to the auxiliary memory of the first auxiliary component.

The handling system may further be adapted to, via the first system communication interface and/or the second system communication interface, cause transmittal of data from the auxiliary memory of the first auxiliary component to the auxiliary memory of the second auxiliary component.

The medical visualisation system may comprise a plurality of medical visualisation devices, each of which may comprise some or all of the features as described in relation to the medical visualisation device disclosed herein. The plurality of medical visualisation devices may comprise different visualisation devices. In an example, a first medical visualisation device may be an endoscope and a second medical visualisation device may be a video laryngoscope. The first and second visualisation devices may comprise different endoscopes.

As used herein, the term "endoscope" refers to a medical visualization device with a positioning interface, or handle, and an insertion cord extending from the positioning interface. As such, the term "endoscope" includes procedure-specific endoscopes, such as bronchoscopes, colonoscopes, cystoscopes, duodenoscopes, enteroscopes, gastroscopes, laparoscopes, ureteroscopes, etc.

The plurality of medical visualisation devices may be different types, e.g. configured for different clinical purposes. For example, the first medical visualisation device may be a first device type configured for a first clinical purpose, and the second medical visualisation device may be a second device type configured for a second clinical purpose. An exemplary clinical purpose may be urology. For example, the first device type or the second device type may be a urology endoscope, such as a cystoscope or a ureteroscope. Another exemplary clinical purpose may be gastroenterology. For example, the first device type or the second device type may be a gastro-intestinal endoscope, such as a gastroscope, a duodenoscope or a colonoscope. Yet another exemplary clinical purpose may be pulmonology. For example, the first device type or the second device type may be a pulmonology endoscope, such as a bronchoscope.

The plurality of medical visualisation devices may comprise image sensors of same or different image sensor type. For example, the image sensor of the first medical visualisation device may be a first image sensor type and the image sensor of the second medical visualisation device may be a second image sensor type. Alternatively, the image sensor of the second medical visualisation device may be the first image sensor type. Alternatively or additionally, the image sensor of a third medical visualisation device may be a third image sensor type or the second image sensor type. The image sensor types may differ on various aspects, e.g. by power supply voltage, by image resolution, by physical size etc.

The auxiliary component may be couplable to the plurality of medical visualisation devices, e.g. the auxiliary component may be couplable both to the first medical visualisation device and the second medical visualisation device and/or the third medical visualisation device. Hence, for example, one auxiliary component may be couplable to a range of different medical visualisation devices.

The present disclosure also provides a solution for providing wireless transmission of image (including video sequences) data from medical visualisation devices to the VPA or other suitable equipment, which act to fulfil requirements for medical visualisation procedures, e.g. reduced latency and utilizing suitable communication bands for hospital settings. Furthermore, the present disclosure provides a solution which allows a VPA or other related devices to adjust parameters of the medical visualisation device, e.g. by wireless data transfer, such that need for processing in a, possibly disposable, visualisation device is reduced.

It is an advantage of the embodiments of the devices and systems disclosed herein that existing protocols and standard components may, to a large degree, be used, making it easier to implement, and reducing manufacturing costs, which is of particular relevance for disposable devices.

It is another advantage of the embodiments of the devices and systems disclosed herein that, in addition to facilitating wireless transfer of image data from the image sensor, the auxiliary component may ease setup of the system prior to a procedure and/or may be used to contain data obtained from the procedure.

It is a further advantage of the embodiments of the devices and systems disclosed herein that operators may use equipment of other departments (e.g. where conventional setup may be different) in a familiar way.

BRIEF DESCRIPTION OF THE FIGURES

Embodiments of the disclosure will be described in more detail in the following with regard to the accompanying figures. The figures show one way of implementing the present disclosure and are not to be construed as being limiting to other possible embodiments falling within the scope of the attached claim set.

DETAILED DESCRIPTION

Figure 1A:
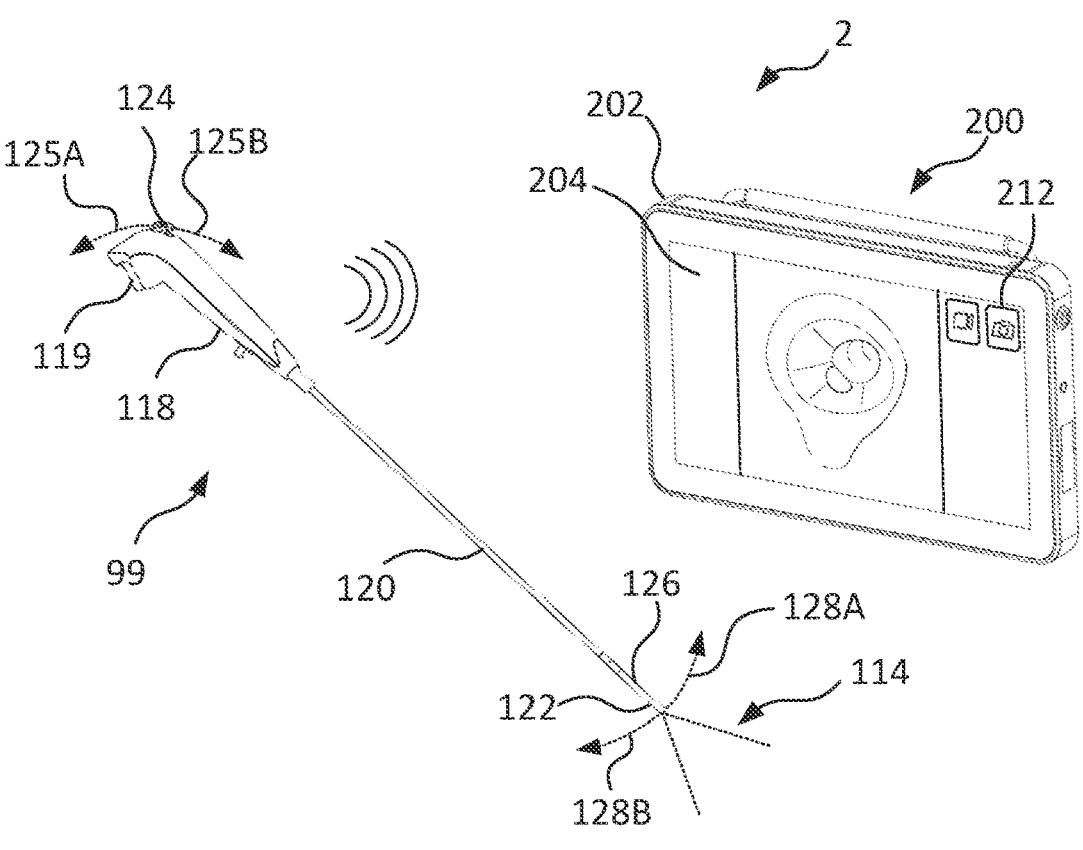
FIG. 1A schematically illustrates an embodiment of a medical visualisation system.

Various embodiments, examples, variations thereof, and details are described hereinafter, with reference to the figures when relevant. The figures may or may not be drawn to scale and that elements of similar structures or functions are represented by like reference numerals throughout the figures. It should also be noted that the figures are only intended to facilitate the description of the embodiments and are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

FIG. 1A schematically illustrates an embodiment of a medical visualisation system 2 comprising a medical visualisation device 99 and a video processing apparatus, or VPA, 200. As shown, the medical visualisation device 99 is an endoscope. Endoscopes comprise specialized devices, which may be tailored for specific procedures, and include bronchoscopes, colonoscopes, duodenoscopes, gastro-intestinal endoscopes, and others. Other medical visualisation devices include laryngoscopes, endotracheal tubes, and, generally, devices insertable into a patient and comprising means to capture video streams of distal or lateral views of the medical visualisation device.

The medical visualisation device 99 comprises a handle 118, an insertion cord 120 extending from the handle 118 to a distal tip 122. The handle may, as illustrated, comprise a control button 124 and the insertion cord 120 may comprise a bending section 126. The control button 124 is adapted to receive an input in a first input direction 125A and in a second input direction 126B. The handle 118 is an example of a positioning interface. Positioning interfaces are described further below. The bending section 126 is adapted to bend accordingly in a first bending direction 128A and a second bending direction 128B. A touch input in the first input direction 125A causes the bending section 126 to bend in the first bending direction 128A. A touch input in the second input direction 125B causes the bending section 126 to bend in the second bending direction 128B. In a variation thereof, the medical visualization device 99 is bendable in two planes, corresponding to four directions, and comprises two control wheels to effect bending in four directions.

The medical visualisation device 99 has an image sensor 112 (shown in FIG. 4) adapted to generate image data indicative of a view 114 from the medical visualisation device. As illustrated, the view 114 from the medical visualisation device 99 may be from the distal tip 122 of the insertion cord 120. The medical visualisation device 99 further comprises a light emitter 116 (shown in FIG. 4) adapted to provide illumination of the view 114. An image capture button 119 may be provided on the handle, its functionality being described below. In a variation thereof, the view 114 is lateral to the longitudinal extent of the insertion cord 120. The image data may have a first resolution, such as 400×400 pixels, or at least 400×400 pixel, such as 800×800 pixels, or at least 800×800 pixels, and may be generated at a first frame rate, such as 30 frames per second, or at least 30 frames per second, such as 60 frames per second, or at least 60 frames per second. The image data, including still images and video sequences, may be used to provide a live view with the VPA. A live view is a view obtained in real-time, during a procedure. Preferably, the VPA is configured to present the images/video sequences with minimal latency. Latency refers to the delay before a transfer of data begins following an instruction for its transfer. Latency is, preferably, smaller than 100 milliseconds. The controller and the transceivers may be structured to minimize latency or at least to reduce latency to an acceptable level, so that latency is not perceived by the operator during the visualization procedure.

The video processing apparatus 200 comprises a first housing 202 and a display 204 surrounded and supported by the housing 202. An image capture button 212 is presented with the display 204. The medical visualisation system 2 may be operable to store an image data file and/or a video stream, or video sequence, file, in response to receipt of a user input signal indicative of a user activating the image capture button 119, 212. The video processing apparatus (VPA) may be a portable video processing apparatus. The portable video processing apparatus may have height H, a width W, and a depth D, with a surface area defined as H×W measuring no more than 12×16 squared inches. The depth may be less than 6 inches. The portable video processing apparatus may comprise a carrying handle and the display may form part of the abovementioned surface area. The portable video processing apparatus may also be devoid of a carrying handle and a display.

The medical visualisation device 99 and the video processing apparatus 200 are adapted to communicate wirelessly. For example, the medical visualisation device 99 is adapted to transmit image data using a downstream data channel from the medical visualisation device 99 to the video processing apparatus 200. Alternatively or additionally, the medical visualisation device may be adapted to receive settings data using an upstream data channel from the video processing apparatus 200 to the medical visualisation device 99.

Figure 1B:
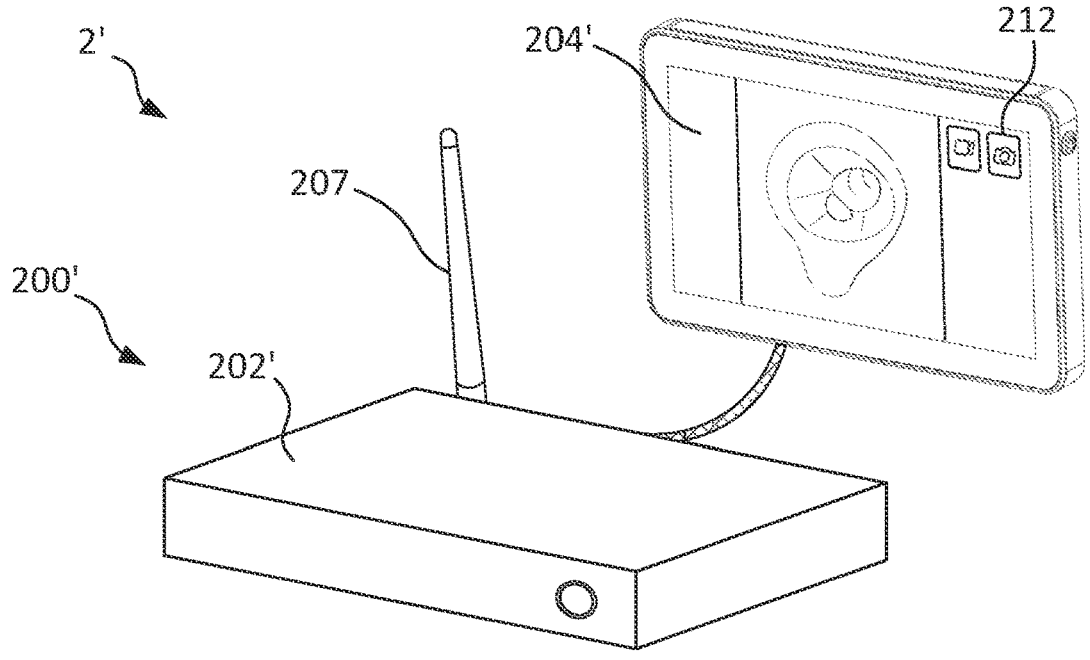
FIG. 1B schematically illustrates components of another embodiment of a medical visualisation system.

FIG. 1B schematically illustrates components of another embodiment of a medical visualisation system 2', albeit with a medical visualization device omitted from the figure. The medical visualisation system 2' comprises a video processing apparatus 200' including a first housing 202' supporting an antenna 207. The medical visualisation system 2' also comprises a display 204' communicatively connected to the video processing apparatus 200'. As shown, the display 204' is communicatively connected to the video processing apparatus 200' via a cable. In variations of the present embodiment, the display 204' is communicatively connected to the video processing apparatus 200' wirelessly via transceivers. Other than the display 204' being external to the first housing 202', the video processing apparatus 200' may be similar and comprise the same functionality as the video processing apparatus 200. For example, the video processing apparatus 200' is operable to receive image data from the medical visualisation device 99 and to cause presentation of a live representation of the image data, indicative of the view 114 from the medical visualisation device 99, on the display 204, 204'. The display 204, 204' may be a touch sensitive display.

The video processing apparatus 200, 200' may be adapted to wirelessly communicate with the medical visualisation device 99. For example, the video processing apparatus 200, 200' may be adapted to receive image data using the downstream data channel from the medical visualisation device 99 to the video processing apparatus 200, 200'. The video processing apparatus 200, 200' may further be adapted to transmit settings data using an upstream data channel from the video processing apparatus 200, 200' to the medical visualisation device 99. Such settings data may, for example, be used to adjust brightness of the light emitter (e.g. by adjusting current, voltage, PWM, duty-cycle etc., depending on how power is supplied to the light emitter) or control colour, contrast, gain and/or exposure settings of the image sensor. These settings may be adaptively adjusted by the video processing apparatus based on the received image data, e.g. to adjust under/over exposure or similar and thus enhance the quality of the images.

In the following description the video processing apparatus 200 may be substituted by the video processing apparatus 200', and both may generally be referred to as the video processing apparatus.

Figure 2:
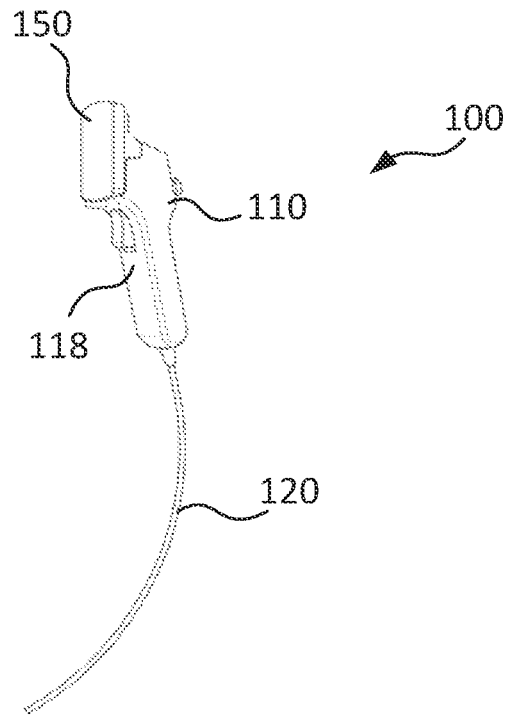
FIG. 2 is a perspective view of an embodiment of a medical visualisation device.

FIG. 2 is a perspective view of another embodiment of a medical visualisation device 100. The medical visualisation device 100 may be an endoscope comprising the same functionality as the medical visualisation device 99. However, the medical visualisation device 100 comprises an auxiliary component 150 and a main component 110. The main component 110 comprises the handle 118, the insertion cord 120, the light emitter and the image sensor, as described with respect to FIG. 1A. The auxiliary component 150 comprises various electronic components, e.g. for establishing wireless communication with the video processing apparatus.

The auxiliary component 150 may be adapted to be used multiple times, e.g. being reusable, while the main component 110 may be configured as a single-use product, e.g. being disposable. By providing electronic components in a reusable component the cost of the main component is reduced. Additionally, in use the main component 110 is in direct contact with the patient's internal tissue and is, preferably, disposed after single use. The reduced cost makes disposability more economically feasible. Thus, valuable resources may be preserved and costs may be lowered, while observing increased patient safety and reduced risk of cross contamination.

The main coupling part and the auxiliary coupling part may have corresponding engagement members, for mechanically coupling the main coupling part and the auxiliary coupling part. The main coupling part may be engaging mechanical coupling with the auxiliary coupling part by displacing the main coupling part along an engagement direction. The main coupling part may be disengaging mechanical coupling with the auxiliary coupling part by displacing the main coupling part along a disengagement direction. The disengagement direction may be opposite the engagement direction. Alternatively, the disengagement direction may be perpendicular to the engagement direction. The auxiliary coupling part may be engaging mechanical coupling with the main coupling part by displacing the auxiliary coupling part along an engagement direction. The auxiliary coupling part may be disengaging mechanical coupling with the main coupling part by displacing the auxiliary coupling part along a disengagement direction. The disengagement direction may be opposite the engagement direction. Alternatively, the disengagement direction may be perpendicular to the engagement direction.

The main coupling part may have a main primary engagement member. The main coupling part may have a main surface with the main primary engagement member. Alternatively or additionally, the main coupling part may comprise a primary surface accommodating exposed portions of the one or more main terminals. The primary surface may be substantially perpendicular to the main surface. The auxiliary coupling part may have an auxiliary primary engagement member adapted to engage with the main primary engagement member of the main coupling part, e.g. to restrict movement of the auxiliary primary engagement member along the main surface and/or perpendicular to the primary surface. The main primary engagement member may be a recess or a protrusion. The auxiliary primary engagement member may be a recess or a protrusion. The auxiliary primary engagement member may be opposite the main primary engagement member. For example, the auxiliary primary engagement member may be a recess and the main primary engagement member may be a protrusion. Alternatively, the auxiliary primary engagement member may be a protrusion and the main primary engagement member may be a recess.

The auxiliary coupling part may have a secondary surface accommodating exposed portions of the one or more auxiliary terminals adapted to contact the exposed portions of the one or more main terminals, when the main coupling part and the auxiliary coupling part are coupled.

The main coupling part may have a main secondary engagement member. The primary surface may be between the main primary engagement member and the main secondary engagement member. The auxiliary coupling part may have an auxiliary secondary engagement member. The auxiliary secondary engagement member may be adapted to engage with the main secondary engagement member of the main coupling part, e.g. to restrict movement of the auxiliary secondary engagement member perpendicular to the main surface and/or along the primary surface.

Figure 3A:
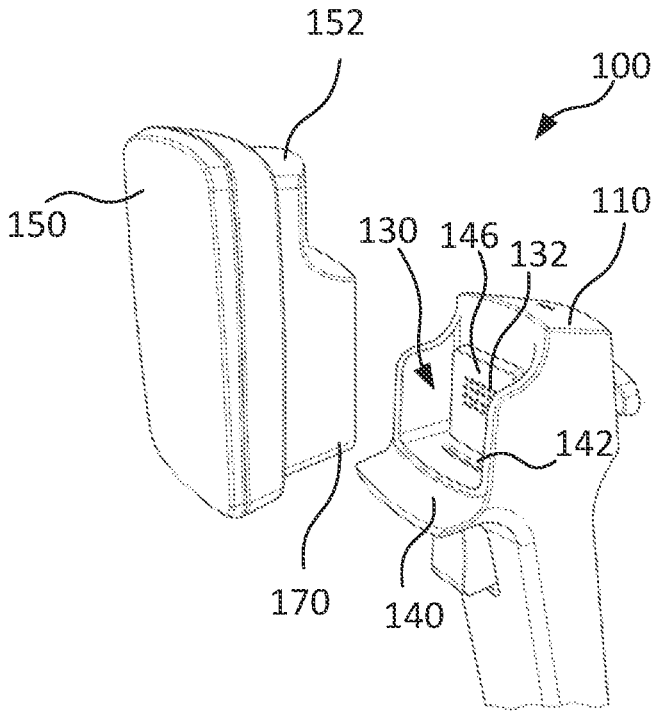
FIGS. 3A and 3B are perspective exploded partial views of the medical visualisation device of FIG. 2.
Figure 3B:
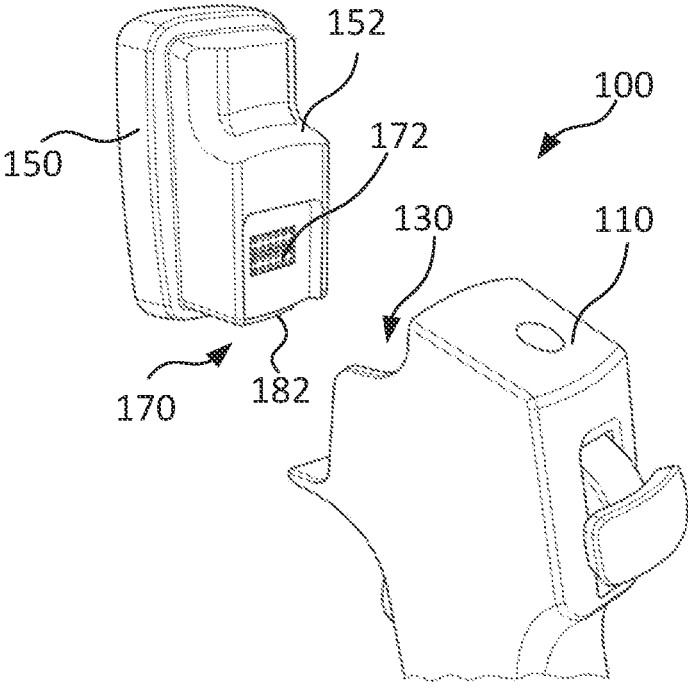

FIGS. 3A and 3B are perspective exploded partial views of the medical visualisation device 100. The auxiliary component 150 comprises an auxiliary housing 152 and an auxiliary coupling part 170. The auxiliary housing 152 may be fluid-tight to the outside such that the auxiliary component 150 is adapted for wet cleaning, e.g. by immersion in a liquid. For example, the auxiliary housing 152 may be surface coated with a sealing liquid, e.g. by immersion in the sealing liquid, to make the auxiliary housing 152 fluid-tight. Alternatively or additionally, terminals of the auxiliary component 150 may be provided by insert moulding, whereby the conductive terminals may be provided, during moulding, in respective positions in the mould for moulding, e.g. by injection moulding, the auxiliary housing. The auxiliary housing may be IP67 compliant. Additional details pertaining to the auxiliary component 150 are described with reference to FIG. 4.

The auxiliary coupling part 170 comprises one or more auxiliary terminals 172 and an auxiliary primary engagement member 182. The auxiliary coupling part may comprise one or more auxiliary terminals adapted to connect to the one or more main terminals, e.g. when the auxiliary coupling part is coupled with the main coupling part. One or more auxiliary communication interfaces may comprise the auxiliary coupling part and/or the one or more auxiliary terminals of the auxiliary coupling part.

The main component 110 comprises a main coupling part 130 adapted to couple with the auxiliary coupling part 170. The main coupling part 130 comprises one or more main terminals 132. The one or more main terminals 132 may be electrically connected to the light emitter and the image sensor. The one or more auxiliary terminals 172 are adapted to connect to the one or more main terminals 132 of the main coupling part 130, when the auxiliary coupling part 170 is coupled with the main coupling part 130. Additional details pertaining to the main component 110 are described with reference to FIG. 4.

The main coupling part 130 has a main surface 140, a main primary engagement member 142, and a primary surface 146. The main primary engagement member 142 may be a recess, as illustrated. Alternatively, the main primary engagement member 142 may be a protrusion. The main primary engagement member 142 may be another suitable engagement member. The main primary engagement member 142 may extend from, or be recessed from, the main surface 140. The primary surface 146 accommodates exposed portions of the one or more main terminals 132. The primary surface 146 may be substantially perpendicular to the main surface 140, as illustrated.

Figure 5:
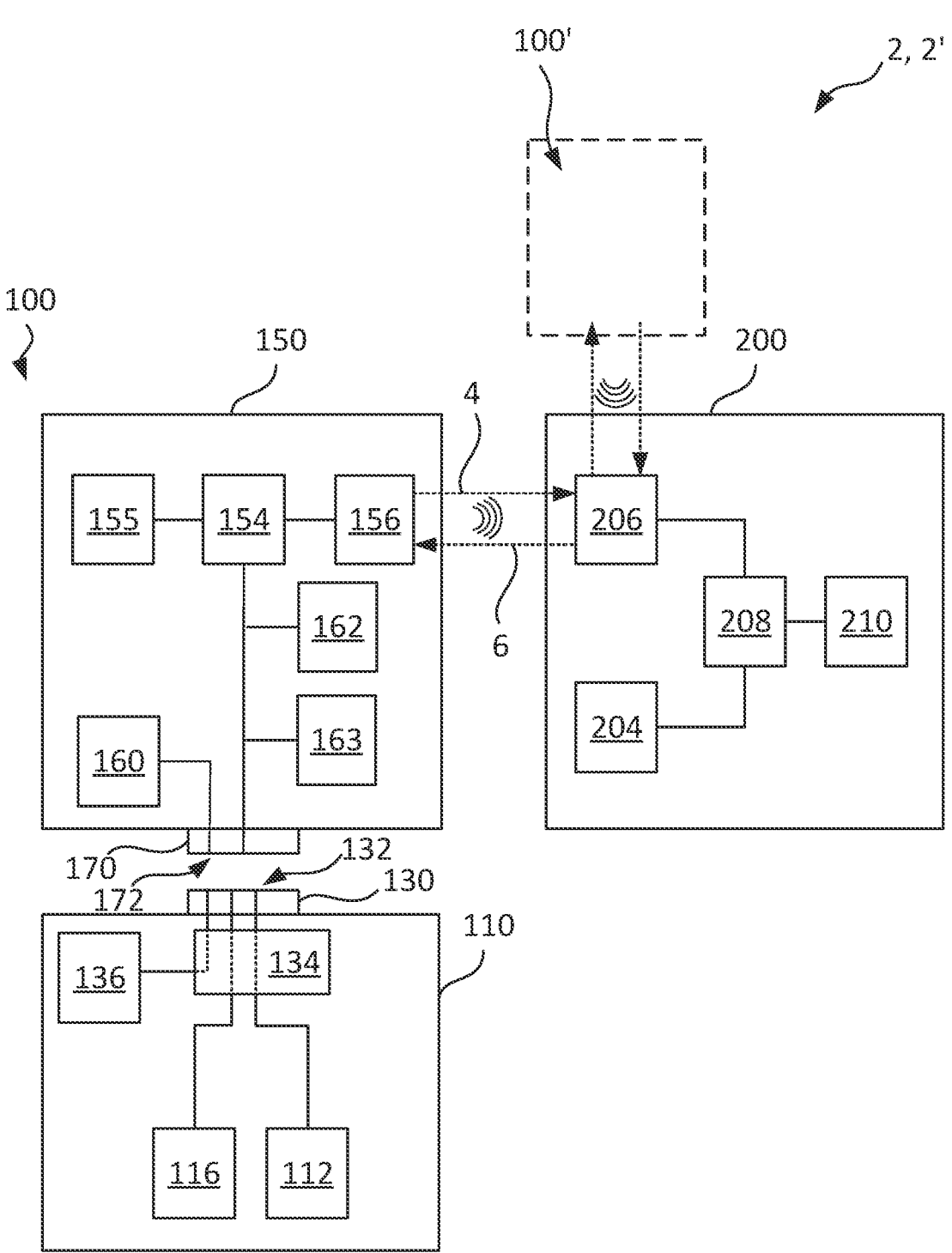
FIG. 5 is a block diagram schematically illustrating an embodiment of a medical visualisation system.

The auxiliary primary engagement member 182 is adapted to engage with the main primary engagement member 142, such as to restrict movement of the auxiliary primary engagement member 182 along the main surface 140. For example, the auxiliary primary engagement member 182 may be a cooperating member of the main primary engagement member 142. For example, the auxiliary primary engagement member 182 may be a protrusion, as illustrated. Alternatively, the auxiliary primary engagement member 182 may be a recess. The auxiliary primary engagement member 182 may be another suitable engagement member. The auxiliary component 150 may further comprise a battery 160, as illustrated in FIG. 5. The battery 160 may be a rechargeable battery.

The main coupling part 130 may have a main secondary engagement member, and the auxiliary coupling part may have an auxiliary secondary engagement member adapted to engage with the main secondary engagement member, such as to restrict movement of the auxiliary secondary engagement member perpendicular to the main surface 140. The primary surface 146 may be between the main primary engagement member 142 and the main secondary engagement member.

The battery 160 is adapted to power the medical visualisation device 100. The battery 160 is adapted to power the electronic elements of the auxiliary component 150, such as the device controller 154 and the device transceiver 156. For example, the battery 160 may be connected to the electronic components of the auxiliary component 150, e.g. the device controller 154 and/or the device transceiver. The battery 160 is electrically connected to the one or more auxiliary terminals 172, such as to power the main component 110 and/or the electronic elements thereof, when the auxiliary component 150 is coupled to the main component 110, such as when the main coupling part 130 is coupled with the auxiliary coupling part 170. For example, the battery 160 may be adapted to power the image sensor 112 and light emitter 114 of the main component 110. The battery 160 may be adapted to power the device identifier 136. The battery may, when fully charged, comprise a battery capacity allowing at least 2 hours of continued usage of the medical visualisation device.

Figure 4A:
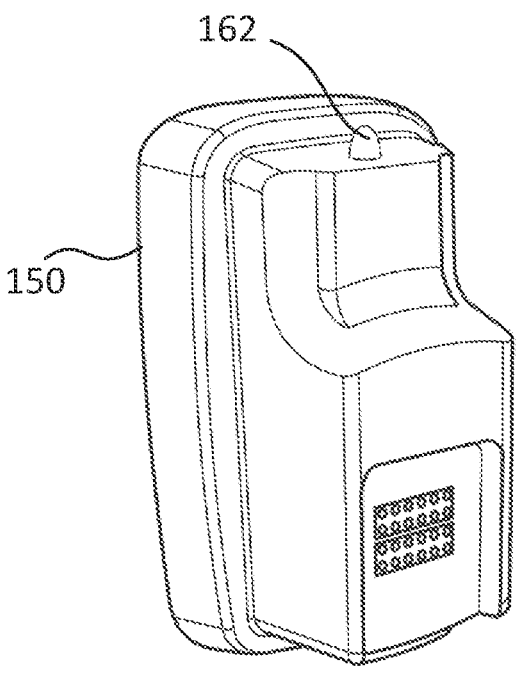
FIGS. 4A and 4B are perspective views of embodiments of auxiliary components of the medical visualisation device of FIG. 2 illustrating examples of wireless communication modules.
Figure 4B:
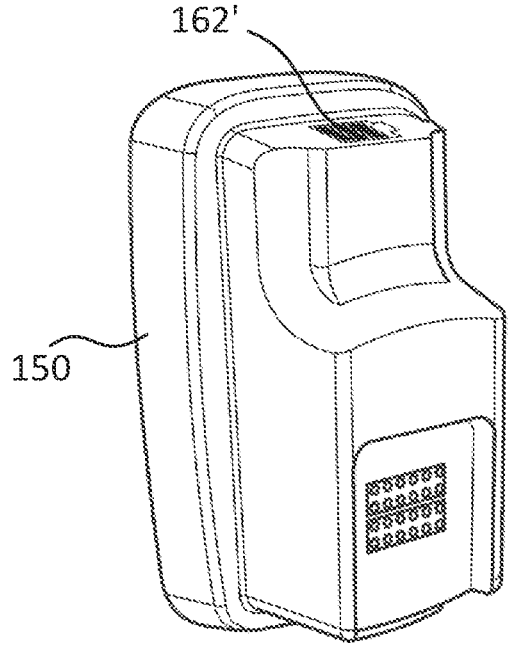

Referring now to FIGS. 4A and 4B, variations of the auxiliary component 150, such as the auxiliary component 150 as described with respect to FIGS. 3A and 3B, may comprise a battery indicator 162, 162' operable to indicate a remaining charge of the battery, particularly when the charge is low. The battery indicator 162, 162' may be an LED or other suitable means for providing an indication of remaining battery charge, thereby making the operator aware of when it is necessary to use a different auxiliary component, and consequently when it is needed to transfer the data stored in the auxiliary memory to another auxiliary component, with a more charged battery.

The battery indicator 162 may comprise an LED, which may indicate the remaining battery charge by being lit in different colours, e.g. green (indicative of full or near full charge), yellow (medium capacity), red (low capacity). The battery indicator 162 may be flashing, e.g. red, when the battery charge is below a threshold amount. In this context, charge refers to the amount of available battery capacity, where full charge is the total capacity of the battery. The threshold amount may be sufficient to effect a full data transfer, for example 10% of the total capacity.

The battery indicator 162' may comprise a plurality of bars (e.g. five) indicative of charge, e.g. fewer bars displayed for less battery charge. The battery indicator 162', comprising a plurality of bars, may be combined with being lit in different colours. For example, by the five following levels of indication, from full charge to near empty: five bars and green, four bars and green, three bars and yellow, two bars and yellow, one bar and red. The battery indicator may be flashing, e.g. red, when the battery capacity is below a threshold charge. The threshold charge may be a charge insufficient to complete a visualization procedure in a typical amount of time, for example, which time may be included in the procedure data. The threshold charge may be a predetermined amount, such as 20% of capacity.

The battery indicator 162, 162' may be comprised in a button adapted to receive a user input. For example, the user may press the battery indicator 162, 162', and the auxiliary device may be adapted to, in response to receiving the user input on the battery indicator 162, 162', to indicate the present battery capacity. For example, the battery indicator 162 may, in response to receiving the user input, light up the battery indicator 162 in accordance with the current battery charge. The battery indicator 162' may, in response to receiving the user input on the battery indicator 162, display the plurality of bars. Thus, battery charge may be conserved by displaying the indication of battery capacity "on demand" when a user presses the battery indicator 162, 162'. Alternatively or additionally, when the battery charge is critically low, the battery indicator 162, 162' may indicate battery charge, e.g. by flashing red, regardless of receiving or not receiving the user input. The battery indicator 162' may be provided using an e-ink display, e.g. such that the battery indicator 162' only uses power when updating the display, e.g. once every day when not being used.

Although the battery indicator 162, 162' is illustrated as being provided on top of the auxiliary device 150, it should be understood that it may be positioned at other convenient positions, depending on the circumstances.

FIG. 5 is a block diagram schematically illustrating an embodiment of a medical visualisation system, such as the medical visualisation system 2, 2' as described with respect to previous figures. The medical visualisation system comprises the medical visualisation device 100 and the video processing apparatus 200, 200'.

The auxiliary component 150 comprises a device processing unit, or device controller, 154 and a device wireless communication module, or device transceiver, 156, which is operable to wirelessly transmit and receive data. The auxiliary component 150 may further comprise an auxiliary memory 155. The device controller 154 may be adapted to read and/or write to/from the auxiliary memory 155. The auxiliary memory 155 may be integrated with the device controller 154. The auxiliary component 150 may further comprise the battery indicator 162, 162' and a pairing/transfer button 163. The pairing/transfer button 163 may be comprised in a button adapted to receive a user input and may be provided on top of the auxiliary device 150 next to the battery indicator 162 or elsewhere in the housing. It should be understood that pairing/transfer button 163 may be positioned at other convenient positions, depending on the circumstances. Alternatively, a further input, e.g. on a second button of the auxiliary component, may indicate whether the data 510 should be transmitted from the first auxiliary component 150 to the second auxiliary component 150' or vice versa.

As described further below, the pairing/transfer button 163 can be actuated by a user to initiate pairing with another auxiliary component and/or to initiate transfer of data from one of the auxiliary components to another. The transfer is discussed below as a transmission of data or, more specifically, of initial data. The transfer may be performed via short-range wireless communication circuits (see FIG. 12) or via a handling system (see FIGS. 17 to 22), for example. The transmitting auxiliary component typically needs to be charged while the receiving auxiliary component may be sufficiently charged, for example to complete a visualization procedure. The pairing/transfer button 163 may be omitted from the auxiliary components, to simplify their manufacture and reduce their cost, if a handling system is used. The pairing/transfer button 163 is only shown in FIG. 5 but can be provided in any of the embodiments of the auxiliary components 150, 150' discussed below. The pairing/transfer button 163 can be programmed to initiate pairing, for example to cause a Bluetooth controller to transmit a pairing signal, as is known in the art. Since one of the purposes of pairing is to transmit or receive data, activation of the pairing button can also be interpreted as a user input to initiate the transfer of data. To distinguish the transmission vs. reception of data, the button may be held activated for a longer or shorter period of time to indicate whether the auxiliary component is to transmit or receive the data. For example, holding the button a long period, for example more than 1 second, can indicate that the auxiliary component is to receive the data. In another example, after pairing the pair of auxiliary devices may transmit to each other their battery charge level and if there is a material difference in charge, as there should be, the auxiliary device with the largest charge is the transmitter and the auxiliary device with the lowest charge is the receiver of the data. Below, the transmitter is generally referred as the second auxiliary component and the receiver of the data is the first auxiliary component.

The main component 110 comprises the image sensor 112, the light emitter 116, and the main coupling part 130, having one or more main terminals 132 electrically connected to the light emitter 116 and the image sensor 112. The main component 110 may further comprise a safety circuit 134 and a device identifier 136, which are described further below.

The video processing apparatus 200, 200' comprises a VPA transceiver 206, a VPA controller 208, and a VPA memory 210. The VPA transceiver 206 is operable to wirelessly transmit and receive data. The VPA controller may be a single integrated circuit part or may comprise more than one integrated circuit part. The VPA memory may be a single part or may comprise more than one part. The VPA 200 incorporates the VPA display 204. The VPA 200' does not incorporate a display. The VPA transceiver 206 may also communicate with a second medical visualization device 100'. The medical visualization devices 100 and 100' may be the same or may be different.

The second medical visualisation device 100' may generally comprise the similar features and components as the first medical visualisation device 100 and is therefore, for brevity, not described in further details. As seen the video processing apparatus 200, such as the VPA transceiver 206 may be adapted to communicate with the second medical visualisation device 100', such as with a device transceiver of the second medical visualisation device 100'. For example, the VPA transceiver 206 may be adapted to receive image data and/or encoded image data using a downstream data channel from the second medical visualisation device 100'. The VPA controller 208 may be adapted to cause the display 204 to display a live representation of the image data of the second medical visualisation device 100', e.g. simultaneously with display of the image data of the first medical visualisation device 100, e.g. side by side or picture-in-picture, or in another arrangement.

The VPA transceiver 206 may further be adapted to transmit settings data using an upstream data channel from the VPA transceiver 206 to the second medical visualisation device 100', such as to a device transceiver of the second medical visualisation device, as similarly described with respect to the medical visualisation device 100.

As used herein, the term "memory" comprises any form of data and instructions storage that may be accessed/read by a controller, including primary and secondary storage. Primary storage, often referred to as random access memory (RAM), is where data is processed and is accessible directly by the controller. RAM may be incorporated in the controller and, if so, may be referred to as controller memory. RAM may also be located in a separate integrated circuit and connected to the controller over a bus. In either structure the RAM used for this purpose may be referred to as cache memory. Secondary storage is where data and instructions are stored. Instructions are, generally, stored in non-volatile memory, which may be referred to as read-only memory (ROM). Other memory may require power to remain in a temporary non-volatile state. Secondary storage memory may comprise flash memory, EEPROM, solid-state drive (SSD) memory, harddisk memory, etc. Some subcontrollers, such as field programmable gate arrays, comprise circuits that combine processing and secondary storage functions.

As used herein, the term "controller" comprises a device or devices capable of processing instructions. A controller typically converts coded instructions into timing and control signals that direct the operation of the other components of the device or system, such as memory, arithmetic logic unit, input and output devices, etc.

Examples of controllers include complex programmable logic devices (CPLD), central processing units (CPU), graphics processing units (GPU), field programmable gate arrays (FPGAs), etc. A controller may be a single integrated circuit part or may comprise more than one integrated circuit part. For example, a controller may comprise a combination of a CPU and an FPGA, or a combination of a CPU, a GPU, and an FPGA. If the controller comprises more than one integrated circuit part, the integrated circuit parts are linked in a supervised or a distributed manner. For example, a primary integrated circuit part can instruct other integrated circuit parts to execute tasks programmed for the other integrated circuit parts. Alternatively, the other integrated circuit parts may execute their functions independently.

In one example, one of the other integrated circuit parts forms part of an input/output interface of the VPA, is programmed to control receipt of the image data from the medical visualization device (MVD), and may be referred to as the MVD I/O subcontroller. The image data may be serial data. The MVD I/O subcontroller may cause conversion of the serial data to parallel data and store it in memory. The primary contoller can then access the parallel data over a parallel bus for processing and presentation with a display.

The device controller 154 is electrically connected to the one or more auxiliary terminals 172 and adapted to process the image data from the image sensor 112, when the auxiliary component 150 is coupled to the main component 110. The device controller 154 may further be adapted to encode the image data to provide encoded image data based on the image data and to transmit the image data and/or the encoded image data to the device transceiver 156, for wireless transmission to the video processing apparatus 200, 200'. For example, the device controller 154 may encode the image data in accordance with a wireless video transmission protocol.

The device transceiver 156 is connected to the device controller 154 and adapted to communicate with the VPA transceiver 206. The device transceiver 156 is adapted to receive the image data and/or the encoded image data and transmit the image data and/or the encoded image data using a downstream data channel 4 to the VPA transceiver.

The VPA transceiver 206 is adapted to receive image data and/or encoded image data using the downstream data channel 4 from the device transceiver 156. The VPA transceiver 206 is connected to the VPA controller 208. The VPA controller 208 may further be adapted to decode the encoded image data. The VPA controller 208 may be adapted to cause the display 204, 204' to display a live representation of the image data. The VPA transceiver 206 may further be adapted to transmit settings data using an upstream data channel 6 from the VPA transceiver 206 to the device transceiver 156, which is adapted to receive the settings data using the upstream data channel 6.

The VPA controller 208 may be adapted to generate and/or provide the settings data to the VPA transceiver 206 for transmission to the medical visualisation device. For example, the VPA controller 208 may generate the settings data based on the image data, e.g. to adjust settings of one or more components of the medical visualisation device 100, e.g. the light emitter 116 and/or the image sensor 112. The device controller 154 may be adapted to receive the settings data from the device transceiver 156 and adjust settings of one or more components of the medical visualisation device 100 based on the settings data. For example, the settings data may be indicative of adjustment of the image sensor, e.g. including colour, contrast, gain, and/or exposure settings. Alternatively or additionally, the settings data may be indicative of adjustment of the light emitter, e.g. including current, brightness, and/or pulse-width-modulation (PWM) settings. By utilizing the upstream data channel 6 to transmit settings data, the VPA controller 208 may process the image data received and continuously adjust settings of the light emitter 116 and/or image sensor 112, to enhance the image quality. Thereby, the heavier computational image analysis may be performed in the video processing apparatus 200, 200', allowing the medical visualisation device 100 to draw less power, needing less battery capacity and effectively allowing the medical visualisation device to be lighter and more compact.

Figure 6:
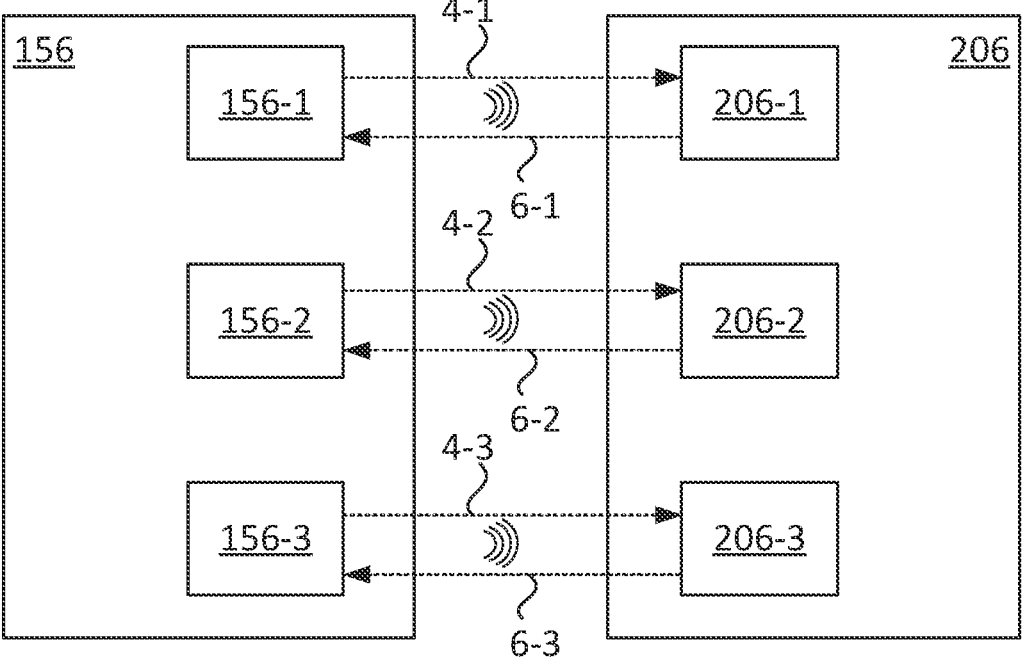
FIG. 6 is a block diagram schematically illustrating examples of wireless communication modules, or transceivers, configured to implement various methods disclosed herein.

FIG. 6 is a block diagram schematically illustrating examples of a multi-channel device transceiver 156 and VPA transceiver 206. The device transceiver comprises a plurality of device transceiver submodules 156-1, 156-2, 156-3 (in this case three transceiver submodules), and the VPA transceiver 206 comprises a plurality of VPA transceiver submodules 206-1, 206-2, 206-3 (in this case three transceiver submodules), each pair of submodules handling one communication subchannel. Each of the VPA transceiver submodules 156-1, 156-2, 156-3 communicates with a respective device transceiver submodule 206-1, 206-2, 206-3. Thereby, the device transceiver 156 and the VPA transceiver 206 may communicate with a plurality of downstream data subchannels 4-1, 4-2, 4-3 collectively forming the downstream data channel 4 of FIG. 4, and a plurality of upstream data subchannels 6-1, 6-2, 6 3 collectively forming the upstream data channel 6 of FIG. 4. A multi-channel transceiver pair can communicate with improved data transmission rates and quality of service. The multi-channel transceiver may be physical, as described with reference to FIG. 5. The multi-channel transceiver may be virtual, in which case it is implemented with single-channel physcial layer using a virtualization technique which may be implemented in an FPGA to provide multiple channels (also referred to as subchannels of the multi-channel transceiver) concurrently. The virtual multi-channel transceiver can offer the same performance, in terms of sensitivity, with less hardware resources. Although 3 upstream and 3 downstream subchannels are discussed, a plurality of downstream and/or upstream subchannels may be implemented to reduce cost or increase bandwidth.

The upstream data channel from the VPA transceiver to the device transceiver may have a limited bandwidth compared to the downstream data channel from the device transceiver to the VPA transceiver. The upstream data channel may have a maximum transmission capacity of or be limited to less than 500 bits per second, such as less than 250 bits per second, such as less than 100 bits per second, such as less than 80 bits per second. The downstream data channel may be able to transmit more than 4 Gbits per second, such as more than 10 Gbits per second, such as more than 15 Gbits per second, such as more than 20 Gbits per second, such as more than 25 Gbits per second.

The communication between the device transceiver and the VPA transceiver may be in accordance with a standard wireless specification. Example standards include the Wireless HD (WiHD) specification and/or the Wireless Gigabit Alliance (WiGig) specification. The device and VPA transceivers may be adapted accordingly. For example, the device and VPA transceivers may comprise a Wireless HD chipset and/or a Wireless Gigabit Alliance chipset.

The image data may be encoded to encoded image data to allow wireless transmission of the image data in accordance with a wireless specification and other reasons. The encoded image data may use a format with a total number of bits, such as 24 bits. A first portion of the total number of bits may be used to encode the image data. The first portion of the total number of bits may be less than the total number of bits. For example, the first portion of the first number of bits may be 10 bits. A second portion of the total number of bits may be used to embed additional information, such as battery status or settings information in the encoded image data.

The device and VPA transceivers may be adapted to communicate using a radio frequency of more than 10 GHz, such as using a radio frequency between 57-66 GHz, such as between 57-64 GHz, such as between 57.05-64 GHz, such as between 59-64 GHz, such as between 59.4-63.56, such as between 59.4-62.9 GHz. These frequencies facilitate high bandwidth and low latency for the live images to be displayed on the display. Furthermore, the example frequencies have a limited range making it advantageous to use for medical visualisation procedures, as this lowers the risk of the image data being interceptable or interfering with other procedures outside the room wherein the procedure is being performed. For example, the VPA and MVD transceivers may operate with the IEEE 802.11ad wireless networking standard which provides a WiGig network using a Multiple Gigabit Wireless System (MGWS) standard at 60 GHz frequency. The 60 GHz band covers the frequency of 57 to 71 GHz. The frequency band is subdivided into 6 different channels in IEEE 802.11ad, each of them occupy 2160 MHz of space and provide 1760 MHz of bandwidth, enabling usage scenarios like transmission of uncompressed UHD video over the wireless network.

The device transceiver may comprise or be configured to connect to a device antenna. The device antenna may be enclosed in a housing of the medical visualisation device and/or of the auxiliary component, such as an auxiliary housing of the auxiliary component. The auxiliary housing may be formed to allow transmission therethrough of the wireless signal between the device and the VPA transceivers. Alternatively, the device antenna may form part of the housing of the medical visualisation device and/or of the auxiliary component. The device antenna may be positioned external to a housing of the auxiliary component, such as the auxiliary housing. Alternatively, the device antenna may extend external of the housing of the medical visualisation device and/or of the auxiliary component. The device antenna may be positioned at a distance from the housing of the medical visualisation device and/or of the auxiliary component, e.g. of more than 0.5 meters, and/or the device antenna may be adapted to be positioned near or at the head of an operator of the medical visualisation device.

It may be advantageous to ensure or promote line of sight between the device antenna and the VPA antenna. Especially for wireless communication utilizing very high radio frequencies, e.g. above GHz, such as between 57-66 GHz, obstacles between transmitter and receiver have a high likelihood of influencing the data transfer. The VPA antenna may be positioned external to a housing of the VPA, such as the first housing. The VPA antenna may be positioned at a distance from the housing, e.g. of more than 2 meters, and/or the VPA antenna may be adapted to be positioned above an operating setting, such as at the ceiling of an operating room. The VPA antenna may be positioned above the first housing. The VPA antenna may be wired to a housing of the VPA, such as the first housing.

Figure 7:
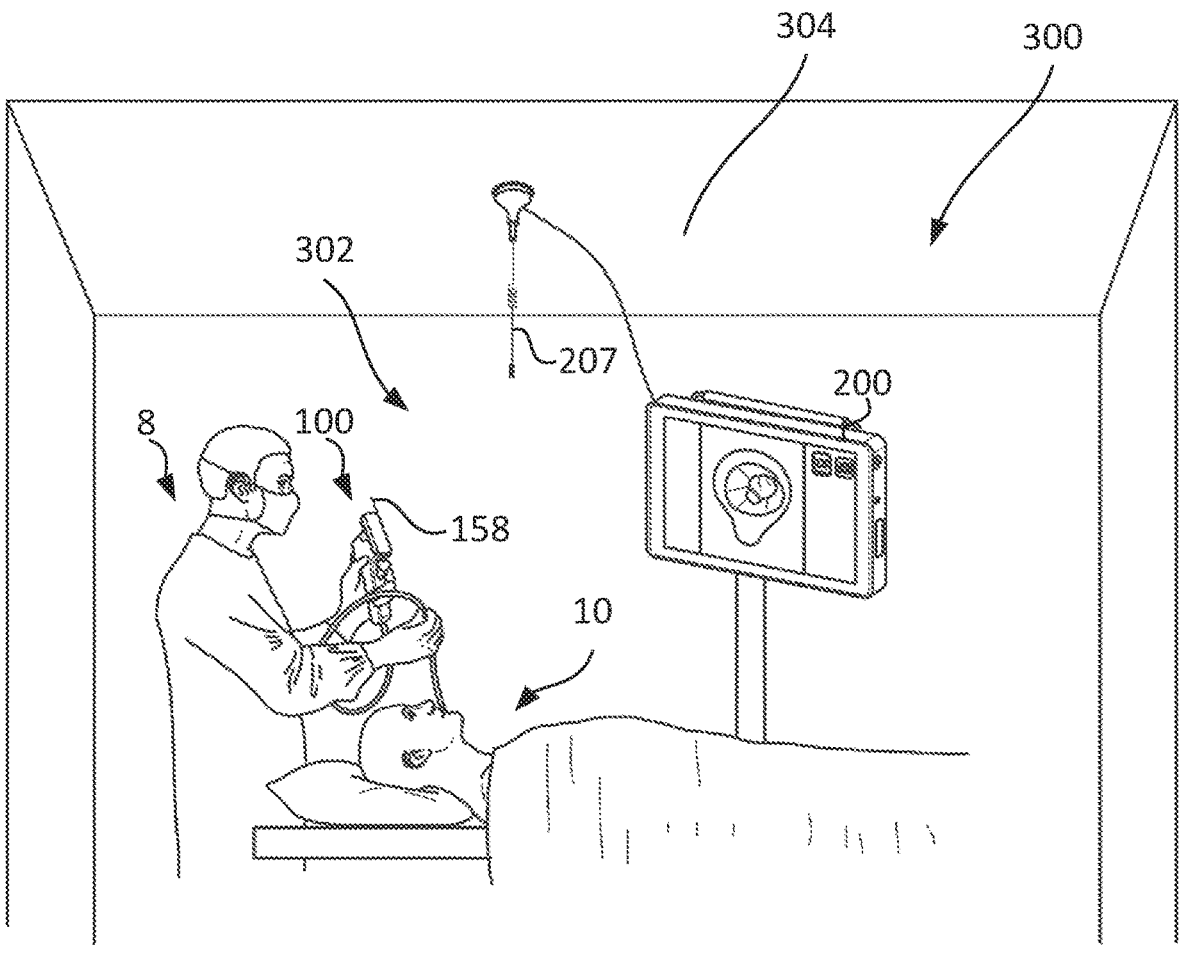
FIG. 7 schematically illustrates an example operating room including the medical visualization system of FIG. 4 and the medical visualization device of FIG. 2.

FIG. 7 schematically illustrates an exemplary operating room 300 with an operating setting 302, wherein an endoscopic procedure is being performed on a patient 10 by an operator 8 of the medical visualisation device 100. The operator 8 is seeing the view from the medical visualisation device 100 at the video processing apparatus 200.

The VPA transceiver of the VPA 200 comprises the VPA antenna 207, and the device transceiver of the medical visualisation device 100 comprises the device antenna 158. Here, the device antenna 158 is shown for the purpose of illustration. Alternatively, the device antenna 158 may be positioned inside the housing of the medical visualisation device 100.

The image data from the medical visualisation device 100 is transmitted to the VPA by wireless communication via the device antenna 158 and the VPA antenna 207. To ensure constant wireless transfer of the image data, it may be advantageous to ensure or promote line of sight between the device antenna 158 and the VPA antenna 207. Therefore, the VPA antenna 207 is positioned external to the housing of the VPA 200. The VPA antenna 207 may be positioned at a distance from the housing, e.g. of more than 2 meters. The VPA antenna 207 may be adapted to be positioned above the operating setting 302, such as at the ceiling 304 of the operating room 300, as illustrated.

The MVD 150 may be pre-programmed with initial data. The initial data may comprise patient data, procedure data, operator data, and other data. The initial data may be uploaded by the VPA from the MVD upon establishing connection between the auxiliary component and the VPA. One benefit of pre-programming the auxiliary component of the MDV is that it small and portable. By contrast, the VPA may be secured in the operating room and while portable, it may be inconvenient to move it. And because the VPA is more expensive than the auxiliary component, it is economical for a hospital to possess many auxiliary components for each PVA. The same holds true in other settings, such as field triage situations, remote medicine and the like.

The wireless communication between the medical visualisation device 100 and the video processing apparatus 200, 200' may be established by activation of a pairing sequence, e.g. by the user pressing a pairing button on the video processing apparatus 200, 200' and on the medical visualisation device 100. In response to activation of the pairing sequence, the device controller 154 and the VPA controller 208 cause the device transceiver 156 and the VPA transceiver 206 to exchange information to setup a data link for subsequent data transfer, e.g. including information regarding communication channel for the data link, identification details of the respective devices, etc.

After establishing the data link, an initialisation sequence may be performed. Alternatively, the initialisation sequence may be performed in response to the auxiliary component 150 and the main component 110 being coupled. The initialisation sequence may include that the VPA receives the device identifier information from the device identifier 136. Based on the device identifier information, the VPA controller 208 is able to process the image data received from the medical visualisation device 100. Based on the device identifier information, the VPA controller 208 may generate and/or provide initial settings data to the VPA transceiver 206 for transmission to the medical visualisation device 100, such as to the device controller 154, which may adjust settings of one or more components of the medical visualisation device 100 based on the initial settings data. Thereby, the settings of the one or more components may be set to a default or initial value, which may be dependent on various information related to the specific device, i.e. based on the device identifier information. Similar to the settings data, explained above, the initial settings data may be indicative of adjustment of the image sensor, e.g. including colour, contrast, gain, and/or exposure settings. Alternatively or additionally, the initial settings data, like the settings data, may be indicative of adjustment of the light emitter.

The initialisation sequence may further include that a designated user interface is loaded on the video processing apparatus 200. For example, a designated user interface may be loaded based on the device identifier information, e.g. depending on the type, model, version, etc. of the medical visualisation device 100.

Figure 8:
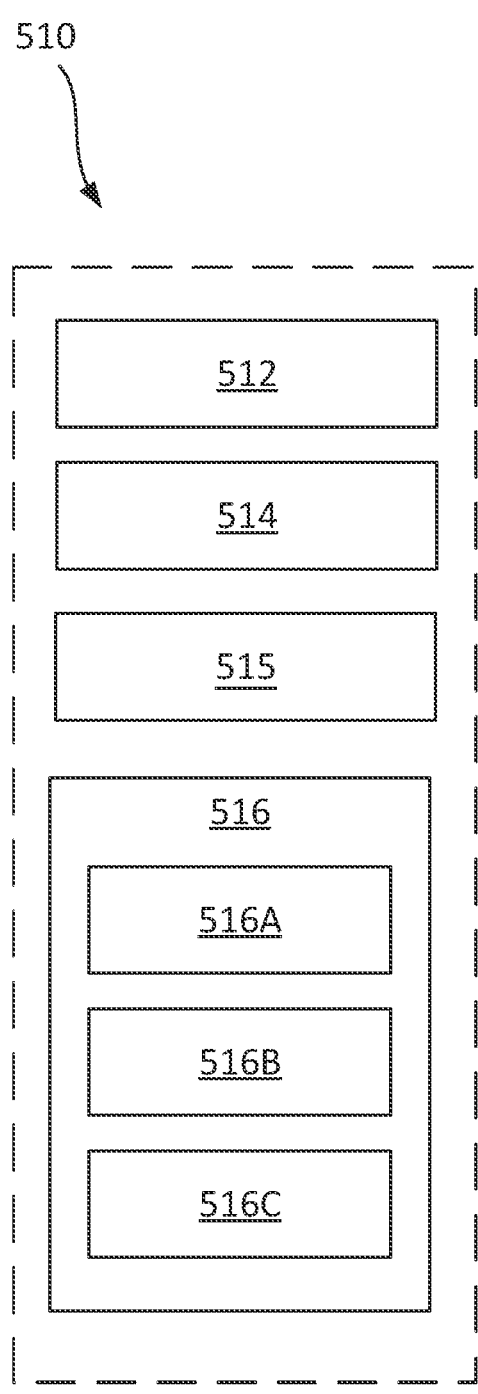
FIG. 8 is a block diagram schematically illustrating an example of data to be transferred from one medical visualization device to another, directly or indirectly.

FIG. 8 is a block diagram schematically illustrating an example of initial data 510 stored in the auxiliary memory 155. The initial data 510 may be loaded by the VPA upon initialisation of a new procedure, e.g. upon establishing connection between the auxiliary component and the VPA. The auxiliary component may be configured to transmit and/or be enablable to transmit the initial data to the VPA using the device transceiver. The VPA controller may be adapted to adjust one or more parameters of the medical visualisation system based on the initial data 510.

For example, the initial data 510 may comprise patient data 512, e.g. of the patient on which the procedure is about to be performed. Thus, the VPA may retrieve and store patient data from the auxiliary component. For example, the auxiliary component may be adapted to follow the patient, and upon performing a procedure, by using the "personal" auxiliary component of the patient, the correct data of the patient is automatically received by the VPA, and the VPA may be adapted to associate the patient data with the image data, such as any stored still images or video sequences. The patient data 512 may include patient name, social security number, etc. The patient data 512 may also include information about the procedure to be performed, medical history, information about allergies, etc. Thereby, all relevant information may be right at hand for the operator of the medical visualisation system.

Alternatively or additionally, the initial data 510 may comprise operator data 514 associated with the operator performing the medical visualisation procedure. Thus, the VPA may retrieve and store operator data from the auxiliary component, such as to log information about the operator performing the procedure. For example, the auxiliary component may be adapted to follow the operator, and upon performing a procedure, by using the "personal" auxiliary component of the operator, the data of the operator is automatically received by the VPA, and the VPA may be adapted to associate the operator data with the image data, such as any stored still images or video sequences. The operator data 514 may alternatively or additionally be indicative of a username or other logon credentials of the operator, such as to facilitate and easier logon process, e.g. of the VPA and/or an associated IT-system. The operator data may also comprise preferences of the operator, such as preferred VPA settings. The operator data may also comprise procedure-specific information. For example, the operator may be a physician that performs bronchoscopies to obtain tissue samples. Information relevant to bronchoscopies, such as models and navigation information that the operator may use to navigate the MVD in the patient, may be included in the operator information. Again, this information may include preferences, such as models the operator prefers to use, routings the operator prefers and so on. Navigation using artificial intelligence and models is described in commonly owned U.S. patent application Ser. No. 18/206,935, titled "Endoscopy Training System," filed on Jun. 7, 2023, which incorporated by reference herein in its entirety.

Alternatively or additionally, the initial data 510 may comprise procedure data 515 associated with the visualization procedure. In one example, the auxiliary component is pre-programmed with data such as images and instructions, process steps, navigation routes, reminders to record images at particular points in the procedure to document that the procedure was performed according to plan, and the like, which may be included to enhance compliance with a particular procedure. Compliance, and the related data, may be developed in a hospital setting as a best practice. The procedure data may then be presented by the VPA on the display to assist the operator in performing the procedure according to the best practice.

The initial data, including patient, operator, and procedure data, may be compiled in a hospital system and then stored in the auxiliary component. A device identifier associated with the auxiliary component may be used in the operating room 300 to recognize the auxiliary component associated with the procedure, the patient, and the operator, to ensure the correct auxiliary component is used.

The auxiliary memory may also work as a storage device for storing image data files and/or video sequence files. Thus, the VPA controller and/or the device controller may store an image data file and/or video sequence file in the auxiliary memory in response to receipt of a user input signal indicative of a user activating an image capture button, as described above in relation to FIG. 1A, or a video capture button. In accordance with the above, the VPA controller and/or the device controller may be adapted to associate the patient data and/or the operator data with the image data file. Thereby, the files stored during the procedure may be conveniently stored on the auxiliary component and follow either the patient or the operator for later retrieval.

Alternatively or additionally. The initial data 510 may comprises operator setup data 516 associated with the operator performing the medical visualisation procedure. Thus, this may be particularly useful when the initial data 510 also comprises operator data 514.

The operator setup data 516 may include image parameters 516A, e.g. including settings for hue, saturation, brightness, contrast, and/or sharpness. The VPA controller may, in response to receiving the initial data 510, adjusts image parameters of the live representation of the image data displayed on the display in accordance with the image parameters 516A of the operator setup data 516. Thus, the system may conveniently adjust parameters to be in accordance with preferences of the operator, thereby reducing unnecessary time to setup the VPA in accordance with individual preferences of an operator.

The medical visualisation system, such as the VPA and/or the medical visualisation device may, as previously described, comprise one or more buttons adapted to receive user inputs. The operator setup data 516 may include button settings 516B indicative of functions assigned to one or more of the buttons, e.g. on the handle of the main component or on the VPA. The VPA controller may, in response to receiving the initial data 510, assign functions to the one or more of the buttons in accordance with the button settings 516B of the operator setup data 516. Thus, the system may conveniently setup the devices in accordance with preferences of the operator, thereby reducing unnecessary manual setup time prior to a procedure.

The VPA controller and/or the device controller may be adapted to perform tasks based on spoken inputs. For example, the VPA may comprise a microphone, or a microphone may be coupled to the VPA, adapted to register utterances from the operator Thus, the operator setup data 516 may include voice control data 516C associated with the operator, e.g. including keywords, training data etc. The VPA controller, after receiving the initial data 510, may identify tasks to be performed based on the spoken inputs and the voice control data 516C of the initial data 516.

The VPA controller may be adapted to store new operator setup data 516, and/or to update the currently stored operator setup data 516 in the auxiliary memory based on a current set of settings of the VPA. For example, the VPA controller may store or update operator setup data in the auxiliary memory in response to receipt of a user input signal indicative of a user requesting storing of the current set of settings. For example, a designated button may be provided, or a certain input, e.g. pressing a predetermined button for more than a predetermined time, may activate a storing/updating procedure of the operator setup data 516.

Safety Circuit.

As disclosed above, the main component 110 may comprise a safety circuit 134. Providing the main component with a safety circuit and/or a device identifier facilitates that the auxiliary component may be used with different main components. Where the main coupling part of the main component may be repositioned relative to the handle of the main component, e.g. by being coupled with flexible device wires, electronic components of the main component, such as the safety circuit and/or the device identifier, may advantageously be provided in the main coupling part, such as to lower the weight of the handle.

The safety circuit may be adapted to prevent excessive current to elements of the medical visualisation device, such as the light emitter and/or the image sensor and/or the device identifier 136. For example, the one or more main terminals 132 may be electrically connected to the light emitter 116, the image sensor 112 and/or the device identifier 136 via the safety circuit. Thereby, the elements of the main component 110 may be protected, in case an auxiliary component able to power another, more power consumptive, device part, is coupled to the main component 110. The safety circuit may comprise a constant current limiting circuit including a transistor, a sense resistor, a reference diode, and voltage reducing diodes (diodes in series). The transistor emitter and collector are connected between the input node and one end of the sense resistor. The voltage reducing diodes are connected between the base of the transistor and the output and the other end of the sense resistor. The reference diode is connected between the base of the transistor and ground. As the current through the two diodes in series begins to rise, they begin to conduct. This lowers the voltage at the base of the transistor and thus reduces the amount of current passing through the collector—emitter junction and subsequently to the output. The safety circuit may comprise a two transistor linear power supply regulator with current limiting. This circuit is like the previous circuit but also includes a second transistor with its collector and emitter connected between the base of the first transistor and the reference diode. The base of the second transistor is connected to the output. The second transistor provides a feedback loop to allow variable control over the output voltage. More complex circuits may be used as provided in integrated circuits such as the Analog Devices LT3092, LM317, LM334, etc. These generally comprise operational amplifiers and therefore may be constructed with individual circuits instead of using an integrated circuit part.

Device Identifier.

As disclosed above, the main component 110 may comprise a device identifier 136. The device identifier 136 may comprise device identifier information, which may be a number or alphanumeric sequence which may uniquely identify the main component 110. The device identifier information may be a serial number of the main component 110. Also, the device identifier information may be indicative of the type and/or model of visualisation device, and may include the type of sensor of the main component. Alternatively or additionally, the device identifier information may be indicative of the brand of the medical visualisation device, production version, firmware version, batch number etc. The information may be combined into one or more codes or files comprising the device identifier information. The device controller 154 may be adapted to obtain the device identifier information from the device identifier 136, e.g. via the one or more auxiliary terminals 172 and one or more main terminals 132.

The device identifier 136 may comprise memory. The device identifier may be a QR-code, bar-code or similar. The device identifier 136 may be connected to the one or more main terminals 132, as illustrated. However, in other exemplary medical visualisation devices, the device identifier 136 may be readable without the necessity to establish an electrical contact. For example, the device identifier 136 may be readable by means of a short-range communication circuit, such as an RFID or NFC circuit. In other exemplary medical visualisation devices, the device identifier 136 may be optically read, e.g. wherein the device identifier is a QR-code or bar code. For example, a camera may be provided in the VPA to read the QR or bar code.

The device controller and/or the VPA controller may be adapted to configure the auxiliary component and/or the VPA to be configured according to the obtained device identifier information, e.g. such as to be compatible with the main component.

A. Auxiliary Component Charging and Copying.

To ensure that the auxiliary component is suitable for use during a visualization procedure, its battery must be sufficiently charged. If it is not, a different, suitably charged, auxiliary component should be used. Different mechanisms for charging batteries and copying initial data are provided herein. In one embodiment, a first auxiliary component communicates with the VPA to transfer data. In a variation thereof, a first auxiliary component communicates with a second auxiliary component to transfer data. In another embodiment, the VPA comprises a component socket operable to charge the battery of an auxiliary component. In a further embodiment, a handling station or system is provided. In an even further embodiment, the VPA comprises or is connectable to the auxiliary component, with a coupling part.

A1. Device-to-VPA Data Transfer.

Figure 9:
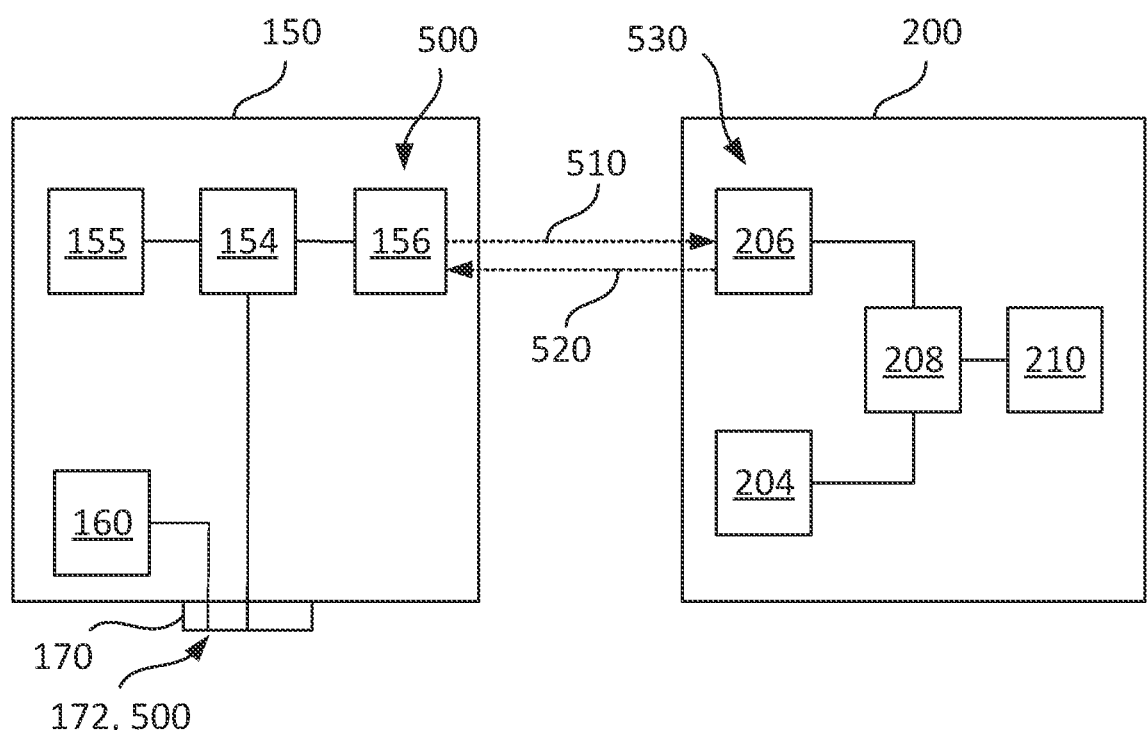
FIG. 9 schematically illustrates data transfers between a medical visualisation device and a video processing apparatus utilizing a high frequency channel, FIG. 10 schematically illustrates data transfers between a medical visualisation device and a video processing apparatus utilizing a short-range wireless channel, FIG. 11 schematically illustrates data transfers between a medical visualisation device and a video processing apparatus utilizing a physical communication channel, FIG. 12 schematically illustrates data transfers between medical visualisation devices utilizing a short-range wireless channel, FIGS. 13 and 14 schematically illustrate one embodiment of a video processing apparatus comprising means to dock and physically connect a medical visualisation device for charging and transferring data.
Figure 10:
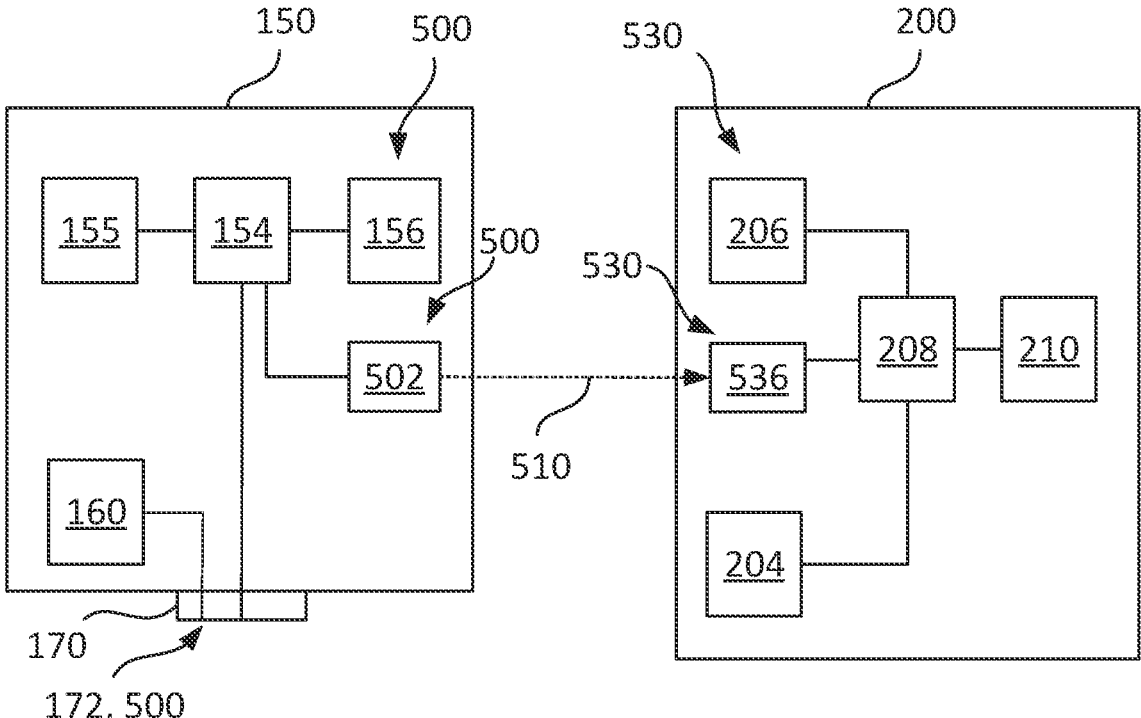
Figure 11:
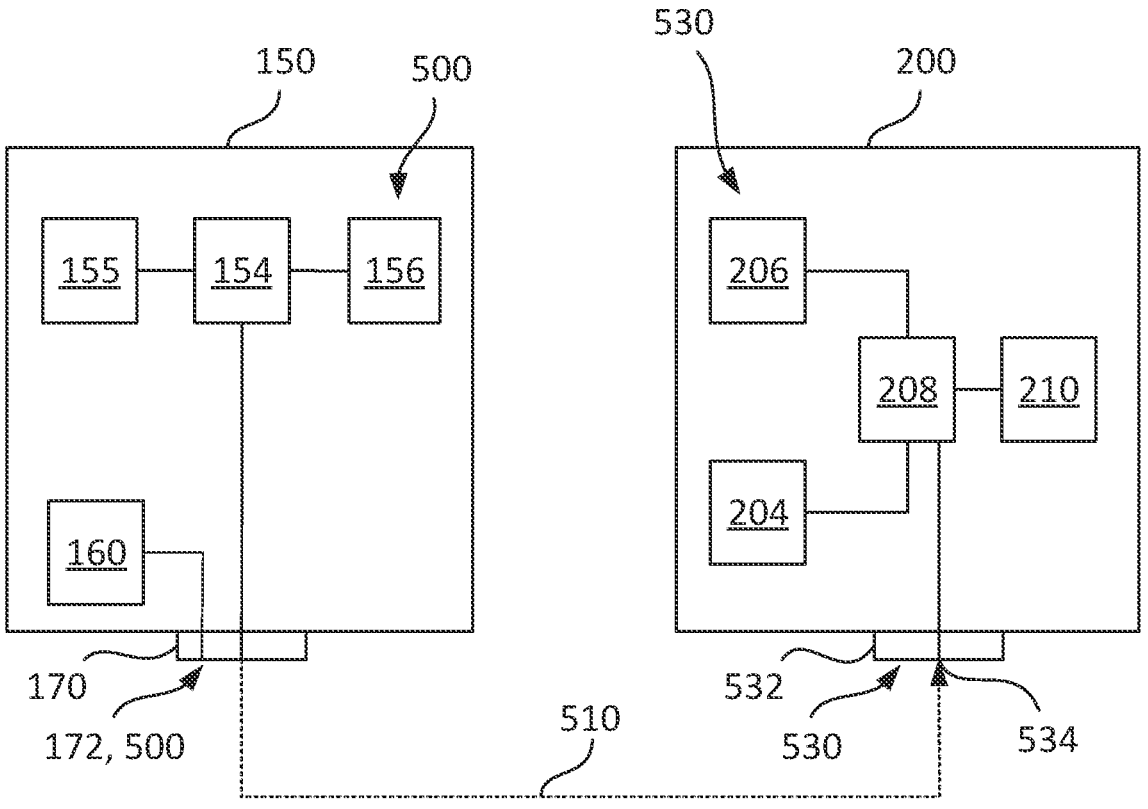

Contactless interfaces include the previously described high frequency upstream and downstream channels 4, 6. Additionally, short-range communication circuits may be provided to establish a short-range communication channel. Upon establishment of communications between the first auxiliary component 150 and the VPA, the VPA controller may cause storage of the transferred initial data 510 in the VPA memory. A second auxiliary component, denoted by numeral 150', may then be paired with the VPA to transfer the initial data 510 (received from the first auxiliary component 150) to the second auxiliary component 150'. As indicated previously, the first transfer may occur responsive to the auxiliary component controller determining that the battery charge is too low, below a threshold, or responsive to a user input. The VPA controller may be programmed to present with a graphical user interface a message instructing an operator to pair the second auxiliary component and to indicate when the second transfer of the initial data is complete. The second transfer may be initiated by the VPA controller responsive to pairing of the second auxiliary component after pairing of the first auxiliary component, optionally within a limited time window. The time window may be less than 10 minutes, optionally less than 5 minutes. Thereafter, the battery of the first auxiliary component may be charged or replaced. FIGS. 9 to 11 exemplify high frequency and short-range communication interfaces.

FIG. 9 is a block diagram schematically illustrating the auxiliary component 150 and the VPA 200. The auxiliary component 150 comprises a plurality of auxiliary communication interfaces 500 including the device transceiver 156 and the auxiliary terminals 172 of the auxiliary coupling part 170. The VPA comprises at least one VPA communication interface 530, including the VPA transceiver 206. The other shown components were described with reference to FIG. 5.

The arrows between the VPA and the auxiliary component represent the transfer of initial data 510 to the VPA and settings or configuration data 520 from the VPA to the auxiliary component via the high frequency upstream and downstream channels 4, 6. This block diagram corresponds to the description of the system described with reference to FIG. 5.

Referring to FIG. 10, the auxiliary communication interfaces 500 may comprise a short-range communication circuit 502, which may be contact or contactless. Example contactless communication circuits include inductive couplings, near field communication (NFC), Bluetooth, ZigBee, and other wireless technologies capable of communicate at short distances, e.g. within a room, at less than Gigahertz frequencies. The VPA communication interfaces 530 may comprise a complementary short-range communication circuit 536, operable to communicate with the short-range communication circuit 502. The short-range communication circuits may be paired to enable short-range data transmission between them. Pairing of Bluetooth, NFC, and ZigBee circuits can be performed as is known in the art. The inductive couplings may be paired by holding the auxiliary component near to the inductive coupling of the VPA for a predetermined period of time. After pairing, the initial data 510 may be transferred from the auxiliary component 150 to the VPA 200. Settings or configuration data 520 from the VPA to the auxiliary component may also be transferred.

FIG. 11 is a block diagram schematically illustrating the auxiliary component 150 and the VPA 200. The VPA communication interfaces 530 includes a VPA coupling part 532 with exposed electrical terminals 534 to contact corresponding exposed electrical terminals of the auxiliary communication interface 500, such as the auxiliary terminals 172 of the auxiliary coupling part 170. The initial data 510 may be transmitted from the auxiliary component 150 to the VPA 200 using the terminals 172, 534. For example, the initial data 510 may be transferred from the auxiliary component 150 to the video processing apparatus 200 after the terminals 172, 534 are connected for a predetermined period of time.

The VPA coupling part 532 may be connectable with the auxiliary coupling part 170 as illustrated, i.e. using the same coupling part of the auxiliary component 150 also used for coupling the main component 110 and the auxiliary component 150. As described below, the physical connection between the auxiliary coupling part 170 and the VPA coupling part 532 may comprise a VPA component socket or a coupling part. The VPA component socket and the coupling part may, in addition to receiving the initial data, charge the battery of the auxiliary component.

In one variation, the short-range wireless interfaces are omitted and the high frequency channel 6 is used to transfer the initial data from the VPA to the second auxiliary component after receipt thereof from the first auxiliary component by the VPA. The VPA controller is programmed, as indicated before, to store the initial data and then, upon establishing the high frequency channel 6, to cause the second transfer. The VPA may encode in the initial data a code or bit to indicate to the auxiliary component controller the nature of the data being received. The auxiliary component controller, upon recognizing the code or bit, will store the initial data. The bit may be toggled to indicate that the initial data is being transferred, for example instead of device settings. Of course, because the VPA already contains the initial data, the second transfer may be omitted. However, the second transfer may be useful to populate the initial data in other or additional auxiliary devices and thus prepare them for use.

A2. Device-to-Device Data Transfer.

Rather than using the VPA as a data bridge between two auxiliary components, as described with reference to FIG. 11, the short-range communication interfaces of the auxiliary components can be used to transfer the initial data from one to the other. The auxiliary components can pair with each other in the same manner as described when pairing an auxiliary component with the VPA.

Figure 12:
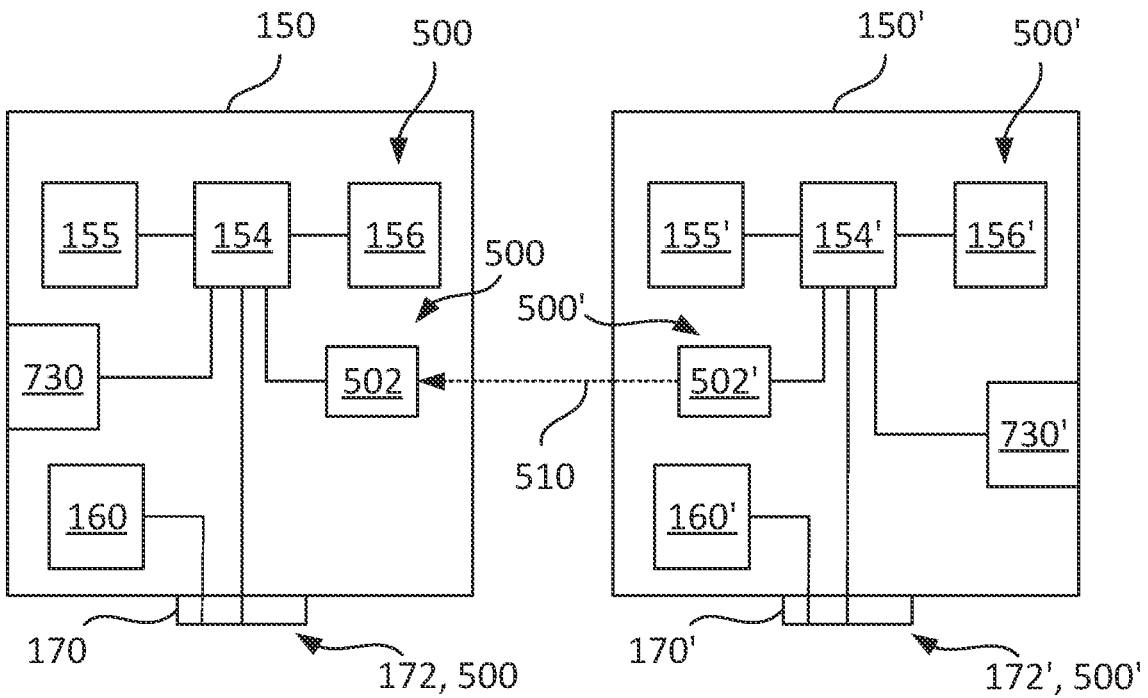

FIG. 12 is a block diagram schematically illustrating communications between the first auxiliary component 150 and the second auxiliary component 150'. An apostrophe is used to denote a component of the second auxiliary component 150' corresponding to the equivalent component of the first auxiliary component 150. The auxiliary components 150, 150' each comprises a rechargeable battery 160, 160' adapted to power electronic components of the auxiliary component 150, 150' and of the respective main component, i.e. of the main component to which it is coupled. Each auxiliary component 150, 150' further comprises an auxiliary memory 155 and one or more auxiliary communication interfaces 500, 500', as described with reference to FIGS. 9 to 11. As shown, the auxiliary components 150, 150' each comprises a plurality of auxiliary communication interfaces 500, 500' including the device transceiver 156, 156', the auxiliary terminals 172, 172', and the short-range communication circuit 502, 502'.

The first auxiliary component and the second auxiliary component may be adapted to transmit, e.g. via the short-range communication circuits, the data from the auxiliary memory of the second auxiliary component to the auxiliary memory of the first auxiliary component, in response to receiving, at auxiliary user interface(s) of the first auxiliary component and/or second auxiliary component, one or more user inputs indicative of a request to transmit the data from the auxiliary memory of the second auxiliary component to the auxiliary memory of the first auxiliary component. Thus, the transmission of the data between the auxiliary components may be provided without the need for further components, such as the handling system described below. The handling system may be referred to as a handling station.

The one or more user inputs indicative of a request to transmit the data from the auxiliary memory of the second auxiliary component to the auxiliary memory of the first auxiliary component may comprise receiving a first user input at the auxiliary user interface of the first auxiliary component and while or after receiving the first user input at the auxiliary user interface of the first auxiliary component receiving a second user input at the auxiliary user interface of the second auxiliary component.

A user input, e.g. at a transmit button, may be received, indicating that a user requests transmitting the data from the auxiliary memory of the second auxiliary component to the auxiliary memory of the first auxiliary component. The data from the auxiliary memory of the second auxiliary component to the auxiliary memory of the first auxiliary component may be transmitted in response to receipt of the user input. The handling system may comprise one or more transmit buttons, e.g. including a first transmit button and/or a second transmit button. The first transmit button may indicate transmission of the data from the second auxiliary component to the first auxiliary component, e.g. by an arrow. The second transmit button may indicate transmission of the data from the first auxiliary component to the second auxiliary component, e.g. by an arrow. The handling system may be adapted to cause the transmittal of the data from the auxiliary memory of the second auxiliary component to the auxiliary memory of the first auxiliary component, in response to a user pressing the first transmit button, e.g. for a predetermined amount of time, e.g. 3 seconds. The handling system may be adapted to cause the transmittal of the data from the auxiliary memory of the first auxiliary component to the auxiliary memory of the second auxiliary component, in response to a user pressing the second transmit button, e.g. for a predetermined amount of time, e.g. 3 seconds.

The auxiliary components 150, 150' may comprise an auxiliary user interface 730, 730'. The auxiliary user interface(s) may comprise a button, a touch screen or other suitable input devices. The operator may activate or actuate the auxiliary user interface 730, 730' to initiate pairing. Alternative schemas to initiate pairing were described above, for example by coupling the auxiliary component with the main component.

If it is desired to establish a physical connection between the auxiliary terminals 172, 172', a cable (not shown) may be provided for that purpose. The cable comprises terminals at both ends arranged to connect with the auxiliary terminals. The terminals of the cable may be provided in a housing physically matching the main coupling part 130, for example.

A3. VPA Charger

The VPA may comprise a component socket operable to charge the battery of an auxiliary component. The component socket may be adapted to engage with the auxiliary component and/or to store the auxiliary component and/or to charge the auxiliary component. The component socket may be adapted to pair the VPA and the auxiliary component. The component socket may comprise one or more VPA terminals. The one or more VPA terminals may be exposed terminals and may comprise one or more charging terminals and/or one or more pairing terminals. The one or more VPA terminals may be adapted to contact corresponding terminals of the auxiliary component.

Providing the VPA with a component socket adapted to engage with the auxiliary component, the auxiliary component may be provided in a convenient position for when it is to be used. The risk of the battery charge being too low to perform a procedure may be reduced as the auxiliary component may be recharged when positioned in the component socket for storing. Also, the auxiliary component may be paired with the VPA, thereby ensuring that the wireless transmission of the video signal is received by the intended VPA, and the user is intuitively made aware of the VPA on which the signal can be expected to be received.

Figure 13:
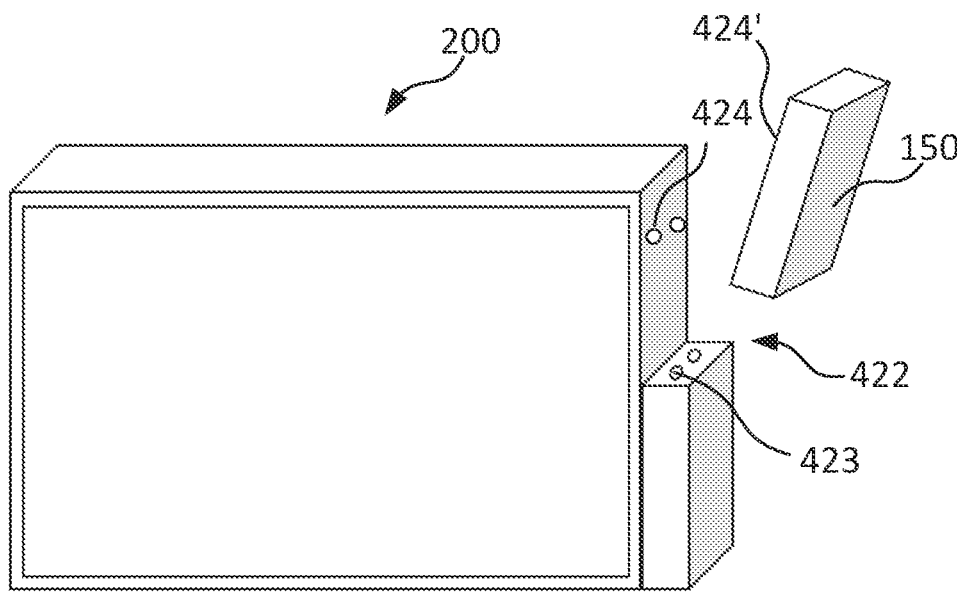
Figure 14:
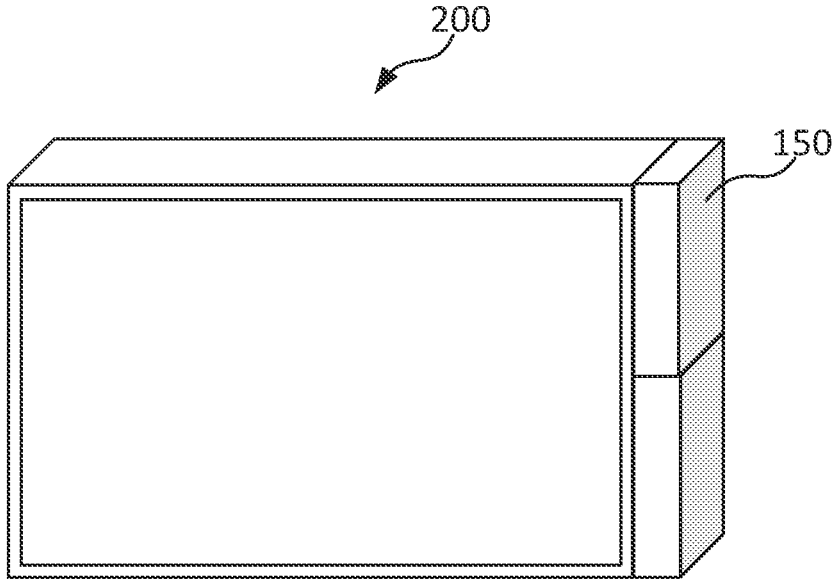

An embodiment of a VPA 200 with a component socket 422, comprising terminals 423, is shown in FIGS. 13 and 14. In FIG. 13 the auxiliary component 150 is not yet attached to the component socket 422. In FIG. 14 the auxiliary component 150 is attached to the component socket 422. As previously described, the VPA 200 comprises a VPA controller 208 and a VPA transceiver 206. The VPA 200 may additionally comprise other elements previously described which for simplicity are omitted from the examples of FIGS. 13 and 14.

The terminals 423 may comprise charging terminals and/or pairing terminals. The component socket 422 is adapted to engage with the auxiliary component 150, such as with the auxiliary coupling part 170 or a secondary auxiliary coupling part 610 (described below) of the auxiliary component 150. Thus, the terminals 172 and 423 may establish electrical connections. The VPA may be adapted to transfer the initial data from the auxiliary component 150 to the VPA 200 via the terminals of the component socket 422 or the wireless connection. The component socket 422 may also or alternatively be adapted to store and/or charge the auxiliary component 150. The VPA may be adapted to pair the wireless communication circuits and transceivers of the VPA 200 and the auxiliary component 150, as described above with reference to FIGS. 9 to 11. The auxiliary component 150 may be held in place in the component socket 422 by magnets. The VPA may include the magnets in a surface thereof, and the auxiliary component 150 may comprise metal parts attracted to the magnets. Of course the placement of the magnets and metal parts may be switched. The metal parts may be also be replaced with magnets positioned in the correct (attracting) polarity. Other forms of mechanical coupling may be used to connect and support the auxiliary component. The coupling may comprise a socket or surfaces shaped to match surfaces of the auxiliary component to form a coupler that is not necessarily a socket.

Magnets and metal parts attracted to magnets may be referred to as magnetic elements. When magnets are used to form a magnetic coupling, they must have the correct polarity to attract. It is to be understood that the correct polarity comprises opposite poles, such that a north pole faces a south pole. When multiple magnets are used on one part, the polarities may be alternated to thus provide attraction and orientation in the magnetic coupling.

In one variation, the component socket 422 may be devoid of terminals, and the component socket 422 may thus serve merely to hold the auxiliary component 150 in a stored position on the VPA 200. A pair of magnets 424 are shown. A metal part or magnets 424' are shown on the auxiliary component 150.

Figure 15:
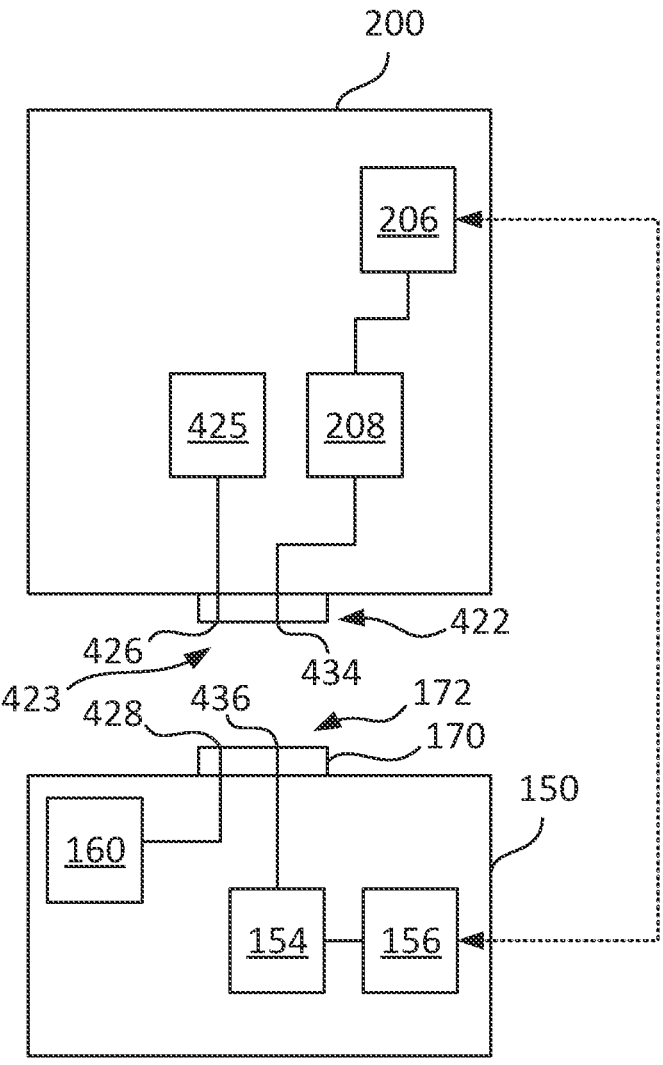
FIGS. 15 and 16 are schematic block diagrams of the embodiment of the video processing apparatus and the medical visualisation device of FIGS. 13 and 14 and of a variation thereof.

FIG. 15 is a block diagram of the VPA 200 and the auxiliary component 150 discussed with reference to FIGS. 13 and 14. The VPA 200 comprises a VPA charging circuit 425 adapted to charge the battery 160 of the auxiliary component 150, when the auxiliary component 150 is engaged with the component socket 422. For example, as illustrated in FIG. 13, the VPA comprise one or more exposed terminals 423, which may include charging terminals 426 to contact corresponding one or more exposed charging terminals 428 of the auxiliary component 150. The charging terminal(s) 428 of the auxiliary component 150 may form part of the auxiliary terminals 172. Hence, the charging terminal(s) 428 may be one or more of the auxiliary terminals 172 adapted to couple to the main component 110. Thereby it may be prevented that the auxiliary component 150 can simultaneously be connected to a charging terminal and to the main component.

The VPA controller 208 may be adapted to pair the device transceiver 206 with the VPA transceiver 156 when the auxiliary component 150 is engaged with the component socket 422. For example, as illustrated in FIG. 13, the VPA may comprise one or more exposed terminals 423, which may include pairing terminals pairing terminals 434 to contact corresponding one or more exposed pairing terminals 436 of the auxiliary component 150. For example, upon contact between the pairing terminals 434, 436, the device transceiver 206 and the VPA transceiver 156 may be paired, e.g. the device controller 154 and/or the VPA controller 208 may cause the device transceiver 206 and the VPA transceiver 156 to exchange information to setup the data link for subsequent data transfer, e.g. including information regarding communication channel for the data link, identification details of the respective devices, etc. The pairing terminal(s) 436 of the auxiliary component 150 may form part of the auxiliary terminals 172. Alternatively, as discussed above, the VPA 200 may be configured to wirelessly pair the transceivers 156, 206 via short-range communication circuits 502, 536, discussed with reference to FIG. 10.

Figure 16:
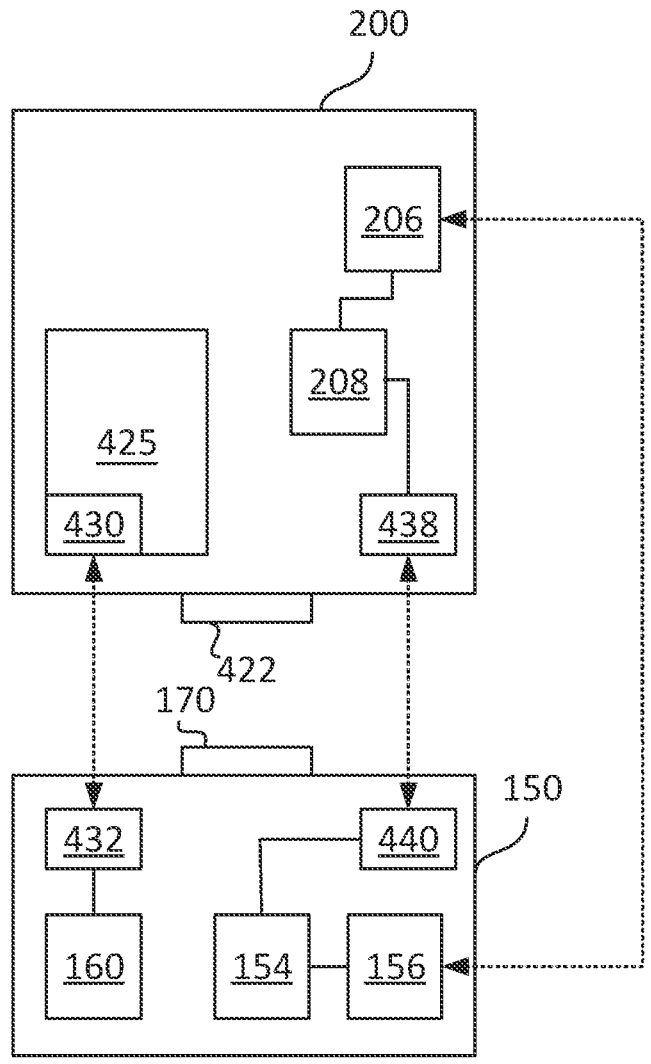

Alternatively, as shown in FIG. 16, the VPA charging circuit 425 may be configured to inductively charge the battery 160 of the auxiliary component 150. For example, the VPA charging circuit 425 may comprise one or more inductive charging coils 430. The inductive charging coil(s) may be adapted to inductively transfer power to one or more inductive receiver coils 432 of the auxiliary component 150. The short-range communication circuits 502, 536, discussed with reference to FIG. 10, are shown as pairing circuits 438, 440, to highlight the difference between charging and pairing.

In FIGS. 15 and 16, the display 204, the VPA memory 210, and the auxiliary memory 155 are omitted to focus attention on the components being discussed. However, the VPA 200 and the auxiliary component 150 include these omitted (from FIGS. 15 and 16) components.

A4. Handling Station or System

The pairing and charging systems described above handle pairing and charging with the VPA and the MVDs. An alternative is to provide a charging and pairing system, referred to as a handling system, that handle those functions and additional functions. An advantage of such as handling system, among other described with reference to the MVD 150 and VPA 200, is that an apparatus can be universally used in a hospital or other setting to handle charging and cleaning of the auxiliary components. The handling system may simplify the use of the visualization system in the hospital or other settings and may leverage the cost of the universal system by contrast with potentially increasing the cost of the several or many VPA and MVDs.

Figure 17:
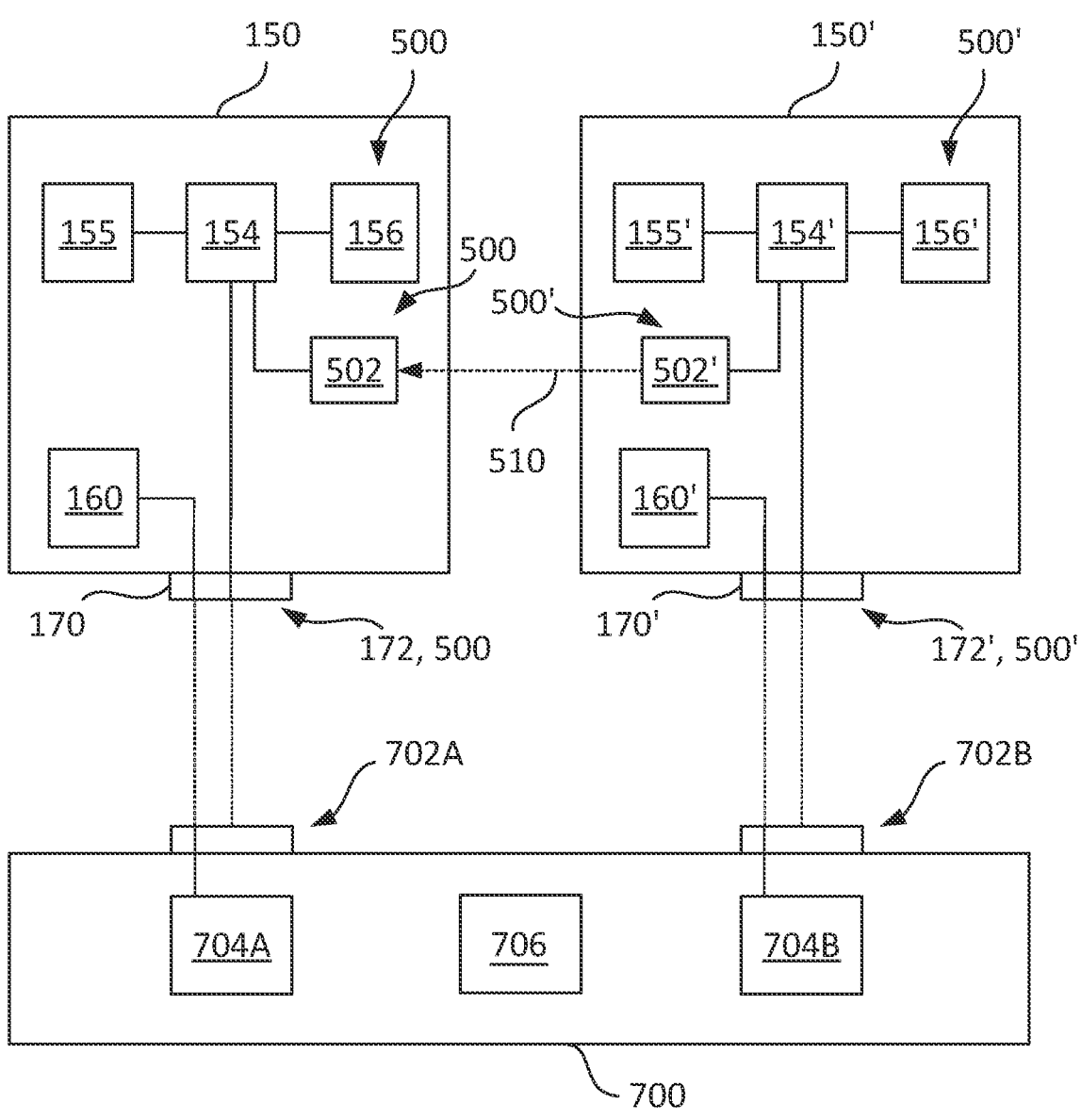
FIGS. 17 to 20 are schematic diagrams of an embodiment of a handling system and variations thereof.

FIG. 17 provides a schematic block diagram of a system including the first and second auxiliary components 150, 150' and a handling system 700 according to the present embodiment thereof. The handling system 700 comprises a first handling system communication interface 702A and a second handling system communication interface 702B. The handling system communication interfaces are adapted to couple with the auxiliary communication interfaces 500, 500' of the first and second auxiliary components 150, 150' via the auxiliary terminals 172 thereof, which were described with reference to FIG. 12. As described there, the auxiliary components 150, 150' may comprise auxiliary user interfaces 730, 730' operable to initiate pairing.

The handling system 700 is adapted to, via the first handling system communication interface 702A and/or the second system communication interface 702B, cause transmittal of data, e.g. the initial data 510 from the auxiliary memory 155' of the second auxiliary component 150' to the auxiliary memory 155 of the first auxiliary component 150. For example, a handling system controller 705 of the handling system 700 may be adapted to cause transmittal of the initial data 510 from one memory to the other via a bus (not shown) connecting selected terminals of the handling system communication interfaces 702A, 702B. The locations of the handling system communication interfaces 702A, 702B may be referred to as component positions.

The handling system controller may send, e.g. via the first system communication interface and/or the second system communication interface, appropriate commands to the first auxiliary component and/or second auxiliary component, to control the transmission of data from the auxiliary memory of the second auxiliary component to the auxiliary memory of the first auxiliary component. Alternatively or additionally, to transmit the data, the handling system controller may be adapted to, e.g. via the second system communication interface, read or receive the data of the auxiliary memory of the second auxiliary component, and, e.g. via the first system communication interface, write or transmit the data from the auxiliary memory of the second auxiliary component to the auxiliary memory of the first auxiliary component.

The handling system may be adapted to, e.g. via the first system communication interface and/or the second system communication interface, cause transmittal of the data from the auxiliary memory of the second auxiliary component to the auxiliary memory of the first auxiliary component by wireless communication between the short-range communication circuit of the first auxiliary component and the short-range communication circuit of the second auxiliary component.

The handling system may comprise a plurality of component positions, e.g. including a first component position adapted to receive the first auxiliary component and a second component position adapted to receive the second auxiliary component. The plurality of component positions may include further component positions, such as a third component position and/or a fourth component positions, such as to allow charging of a higher number of auxiliary components, thereby increasing the likelihood that a fully charged auxiliary component may be available at the handling system. In case of more than one auxiliary component being available to receive the data, the handling system may be adapted to cause transmission of the data to the auxiliary component with the mostly charged battery. The auxiliary components may communicate their state of charge to the handling system controller and the handling system controller may compare the values to determine which of the auxiliary components has the highest charge.

The handling system communication interfaces 702A, 702B may comprise wiring of terminals which upon coupling with the auxiliary components 150, 150' activate a procedure in the auxiliary components 150, 150' to transmit the data 510. As illustrated with reference to FIG. 12, the initial data 510 may be transmitted by wireless communication between the short-range communication circuit 502 of the first auxiliary component 150 and the short-range communication circuit 502' of the second auxiliary component 150. The initial data 510 may, alternatively, be transmitted by wireless communication, between the transceivers 156' 156'. The procedure, subroutine or sequence of processing instructions in the auxiliary components may be structured to receive a signal from the handling system communication interfaces 702A, 702B and upon receipt of the signal commence pairing with the other auxiliary component, if the initial data 510 will be transmitted wirelessly, and initiate transmission via the terminals 172, 172' if the initial data 510 will be transmitted therethrough instead of wirelessly, since pairing not necessary in that case. The signal may be transmitted via a hardwired circuit, such as, for example, establishment of a conductive path between respective terminals of the handling system communication interfaces 702A, 702B, which establish a conductive path between the terminals 172, 172'. If a particular impedance is available, this would indicate that the path is completed and data transmission may begin. Alternatively, the signal may be caused by a handling system controller 706. Even further, pairing may be commenced by activation or actuation of the auxiliary user interfaces 730, 730', when they are present. The handling system may also comprise a handling system memory 707. The handling system memory 707 may be used to buffer data in the process of transferring the data between memories of the auxiliary devices and external memory (discussed below with reference to FIGS. 18 and 20).

The handling system 700 further comprises handling system charging circuits 704A, 704B adapted to charge the rechargeable batteries 160, 160'. In the illustrated example, the handling system 700 comprises a first handling system charging circuit 704A adapted to charge the rechargeable battery 160 of the first auxiliary component 150 and a second handling system charging circuit 704B adapted to charge the rechargeable battery 160' of the second auxiliary component 150'. Charging circuits for rechargeable batteries are well known and will not be described further. Generally, a charging circuit throttles the amount of current flowing to a rechargeable battery to ensure the battery is not overloaded/damaged by the charging process. The current flow may depend on the battery type, capacity, and state of charge. The current flow will typically reduce as the battery charge approaches the battery's capacity. A common charging circuit may also be used, in which case the supply of power is divided between the rechargeable batteries 160, 160'.

The handling system 700 may be adapted to validate the data 510 of the auxiliary memory 155 of the first auxiliary component 150 after transmittal of the initial data 510 from the auxiliary memory 155' of the second auxiliary component 150' to ensure that the data 510 is correctly transmitted and stored in the auxiliary memory 155 of the first auxiliary component 150, such as to make sure the data was successfully transmitted and was not corrupted. A checksum value may be transmitted as part of or separately from the initial data 510. Upon receipt of the initial data 510, the device controller of the first auxiliary component may calculate the checksum value and compare it to the received value to determine if a match, indicative of a correct transmission, is made (e.g. the calculated and transmitted values are identical). Validation and deletion may occur in a similar manner in any of the aforementioned systems, for example those described with reference to FIGS. 5 and 9 to 16. The validation of the data of the auxiliary memory of the first auxiliary component may be caused by the handling system controller or by the device controller of one of the auxiliary components. The second device controller or the handling system controller may request and receive, from the first device controller, a checksum value or other indication to compare to a copy of data held in the memory of the handling system, to perform the comparison and validation. Because of the one-to-many relationship, it is advantageous to add functionality to the handling system instead of the auxiliary components. However, this is not the case if the functionality can be added without adding cost to the auxiliary components.

The handling system 700 may be adapted to delete the initial data 510 from the auxiliary memory 155' of the second auxiliary component 150' after transmittal of the initial data 510 to the auxiliary memory 155 of the first auxiliary component 150 and, preferably, after having validated the initial data 510 of the auxiliary memory 155 of the first auxiliary component 150. Deletion may be responsive to a signal caused by the controller of the first auxiliary component 150 after receipt and/or valuation of the initial data 510. The handling system controller may receive the signal and, in turn, command the second auxiliary component to delete its initial data 510. Alternatively, the second auxiliary component may delete its initial data 510 responsive from the signal from the first auxiliary component or after a predetermined amount of time after the data was transmitted to the first auxiliary component.

Figure 18:
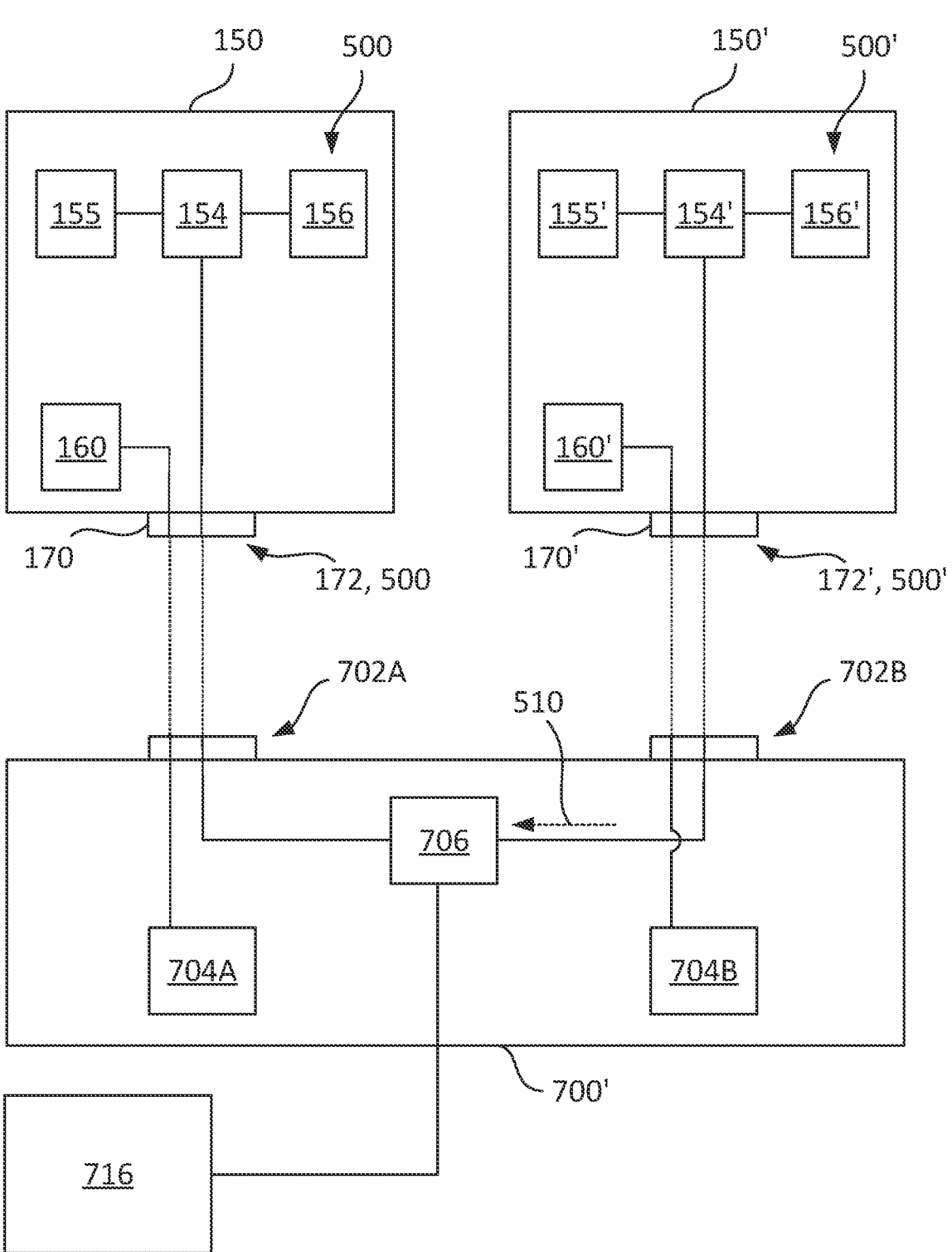

FIG. 18 is a block diagram schematically illustrating a variation of the embodiment of the handling system 700, denoted by numeral 700'. The handling system 700 may comprise the functionality and components of the handling system 700. In the present variation the auxiliary components 150, 150' are similar to the auxiliary components 150, 150' described and illustrated in relation to FIG. 17. However, as illustrated, the short-range communication circuits 502, 502' are omitted to indicate that they are optional. The handling system 700' is similar to the handling system 700. However, as illustrated, the handling system controller 706 is connected to the handling system communication interfaces 702A, 702B. Thus, the handling system 700' transmits the initial data 510 from the auxiliary memory 155' to the auxiliary memory 155, by the handling system controller 706 reading the initial data 510 via the second handling system communication interface 702B and the bus and optionally via the device controller 154' of the second auxiliary component 150', and the handling system controller 706 writing the initial data 510 to the auxiliary memory 155 via the first handling system communication interface 702A and optionally via the device controller 154 of the first auxiliary component 150. Initiation of transmission may be handled by the handling system controller 706 communicating with the device controllers 154, 154' or directly reading and writing to the auxiliary memories 155, 155'.

The handling system 700' may further be connectable to an external memory 716, e.g. at a server. The handling system 700', such as the handling system controller 706 of the handling system 700', may be adapted to store the initial data 510 at the external memory. For example, the external memory 716 may provide a backup in case data at an auxiliary component is corrupted or lost.

Although the handling system and pairing has been described with reference to the initial memory 510, the devices, components, systems and methods described above are equally applicable to transver any data between the auxiliary memories 155, 155' and/or the VPA memory or the external memory 716.

Figure 19:
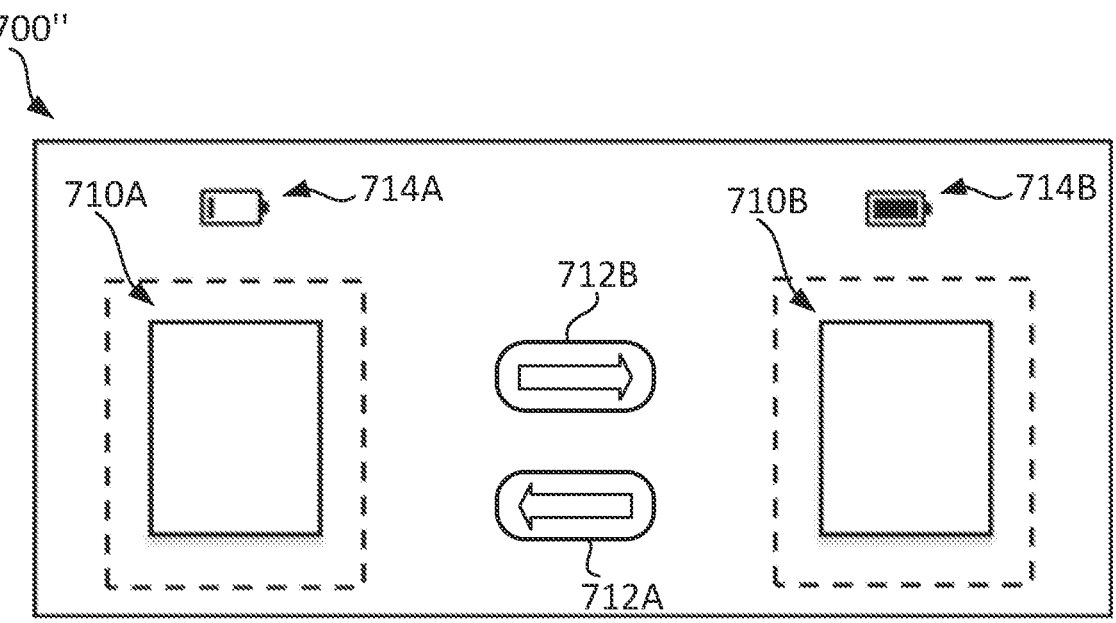

FIG. 19 schematically illustrates another variation of the handling system 700, denoted by numeral 700". The handling system 700" may comprise the functionality and components of the preceding variations of the handling system 700. The handling system 700" comprises a plurality of component positions including a first component position 710A adapted to receive the first auxiliary component (not shown) and a second component position 710B adapted to receive the second auxiliary component (not shown). The component positions 710A, 710B may comprise terminals of the handling system communication interfaces 702A, 702B as described above. The positions may comprise coupling parts similar to the main coupling part 130.

The user may position a first auxiliary component in the first component position 710A and a second auxiliary component in the second component position 710B to have data transmitted from the second auxiliary component to the first auxiliary component and/or from the first auxiliary component to the second auxiliary component. In one example, the data may be transmitted automatically after the user has positioned the auxiliary components, e.g. after a predetermined time, optionally after providing a visual or audible indication of data being transmitted, to allow the user a chance to cancel the transmittal, if it was not intended. In other example, as illustrated, the handling system 700" may comprise one or more transmit buttons 712A, 712B, and be adapted to cause the transmittal of data upon a user pressing the first transmit button. The first transmit button may be pressed for a predetermined amount of time, e.g. 3 seconds, to prevent accidental transmissions. For example, the handling system 700" may comprise a first transmit button 712A and may be adapted to cause the transmittal of data from the auxiliary memory of the second auxiliary component, i.e. the auxiliary component being positioned in the second component position 710B, to the auxiliary memory of the first auxiliary component, i.e. the auxiliary component being positioned in the first component position 710A, upon a user pressing the first transmit button 712A.

The handling system 700" may comprise a second transmit button 712B, and the handling system 700" may be adapted to cause the transmittal of data from the auxiliary memory of the first auxiliary component, i.e. the auxiliary component being positioned in the first component position 710A, to the auxiliary memory of the second auxiliary component, i.e. the auxiliary component being positioned in the second component position 710B, upon a user pressing the second transmit button 712B.

By providing both a first and a second transmit button 712A, 712B, the user may arbitrarily choose which of the auxiliary components should receive the data of the other auxiliary component.

The handling system 700" may further comprise one or more battery indicators 714A, 714B adapted to display a visual indication of estimated battery capacity of the rechargeable battery of the first auxiliary component and/or the second auxiliary component, i.e. the auxiliary component being positioned in the first component position 710A and/or the second component position 710B, respectively. For example, the handling system 700" comprises a first battery indicator 714A adapted to display a visual indication of estimated battery charge of the rechargeable battery of the auxiliary component positioned in the first component position 710A. Furthermore, the handling system 700" comprises a second battery indicator 714B adapted to display a visual indication of estimated battery charge of the rechargeable battery of the auxiliary component positioned in the second component position 710B.

Figure 20:
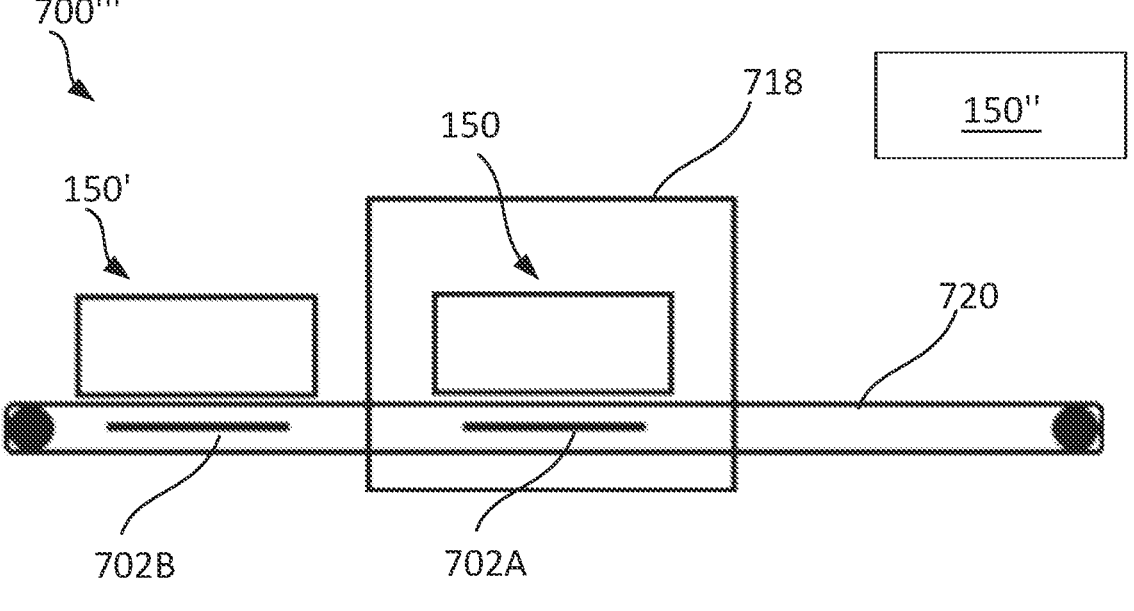

FIG. 20 schematically illustrates another variation of the handling system 700, denoted by numeral 700'''. The handling system 700" may comprise the functionality and components of the handling system 700 and the variations of the handling system 700. The handling system 700'''' comprises, in addition to the component positions 710A, 710B, a disinfection area 718 adapted to disinfect an auxiliary component positioned therein. For example, the disinfection area 718 may comprise a chamber where the auxiliary component is subjected to ultraviolet radiation, gas, heat, steam, and/or a disinfecting fluid. The handling system 700—is adapted to transmit of the initial data 510 from the auxiliary memory of the second auxiliary component 150' to the auxiliary memory of the first auxiliary component 150, position the second auxiliary component in the disinfection area 718. Thus, a newly disinfected auxiliary component may be available for later receipt of the initial data 510.

The handling system 700''' may further comprise a conveyor, such as a conveyor belt 720, as illustrated, for repositioning the auxiliary components 150, 150'. For example, the conveyor belt 720 may, e.g. after transferring the data from the second auxiliary component 150' to the first auxiliary component 150, move the second auxiliary component to the prior position of the first auxiliary component, e.g. above the first handling system communication interface 702A and/or within the disinfection area 718, and provide the first auxiliary component 150 for retrieval by the user on the opposite side of the disinfection area 718. The handling system controller may control operation of the conveyor belt, driven by electric motors. The handling system controller may thus control how long the auxiliary component stays in the disinfection area, may control operation of UV lights, fluid sprays, and the like to ensure that disinfection is complete. The handling system controller may control disinfection responsive to completion of the data transfer, which may be initiated by handling system controller. Alternatively, the handling system controller may receive a signal from the auxiliary component indicating that the data transfer is complete.

Also shown is a third auxiliary component, denoted by numeral 150" and discussed below. The third auxiliary component may be the same or different from either of the first or second auxiliary components. However, the third auxiliary component includes the components necessary to function as described, including auxiliary memory, controller, interfaces, transceiver, etc.

Figure 21:
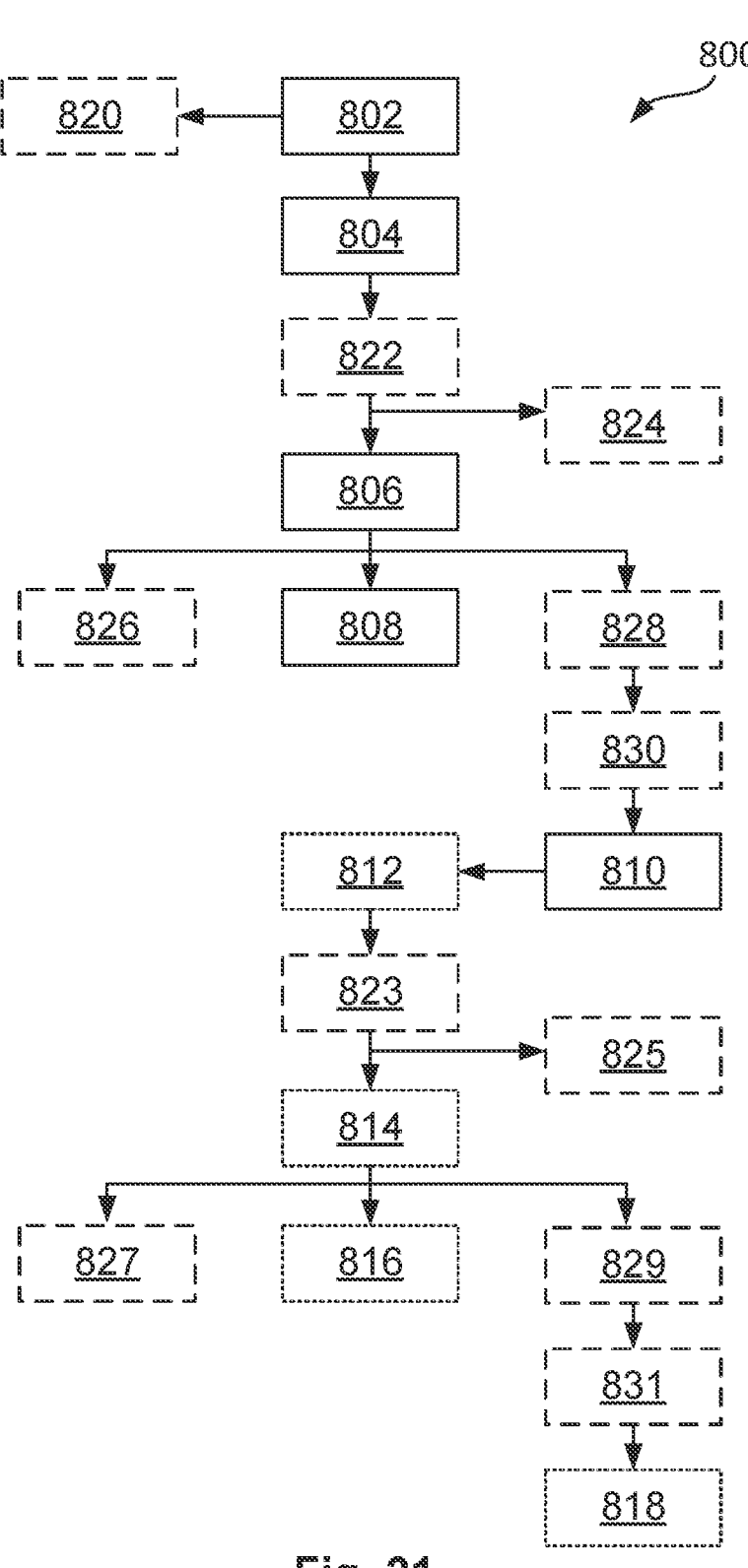
FIGS. 21 and 22 are flowcharts of a method of using the handling systems of FIGS. 17 to 20, and a variation thereof.

FIG. 21 is a block diagram of an embodiment of a method, denoted by numeral 800, for handling auxiliary components, e.g. including a first auxiliary component 150 and a second auxiliary component 150', as described in relation to the previous figures. Some of the functions of the method are performed by the handling system, unless the function is performed by a user as indicated below, for example by providing the auxiliary components. In the context of this description of the method, the data is transferred from the second auxiliary component 150' to the first auxiliary component 150. Thus, the terms first and second in this context refer to the auxiliary components and not the positions in the handling system. However, the method is simpler to understand if the first and second auxiliary component are received in the first and second component positions, respectively.

The method 800 comprises, at 802, receiving a first auxiliary component and, at 804, receiving a second auxiliary component, at a handling system, such as the handling system 700, 700', 700", or 700'". Said receiving may be in first and second component positions of the handling system. The second auxiliary component may be received before the first auxiliary component.

After receiving the first and second auxiliary components, the method 800 comprises, at 806, transmitting or transferring the data, such as initial data, from the auxiliary memory of the second auxiliary component to the auxiliary memory of the first auxiliary component.

After transmitting the data at 806, the method 800 comprises, at 810, providing, releasing, and/or making available the first auxiliary component for retrieval, e.g. for the user to retrieve the first auxiliary component, now including a copy of the data previously stored in the auxiliary memory of the second auxiliary component.

Optionally, the method 800 may further comprise charging, at 820, the rechargeable battery of the first auxiliary component. Said charging may be performed immediately after receiving the first auxiliary component, at 802, or any time thereafter.

Optionally, transmitting the data may be responsive to receiving, at 822, a user input to initiate the transfer of the data. The user input may be responsive to a transmit button actuated by the user. The data transmission is initiated, at 806, in response to receiving the user input at 822.

Optionally, after transmitting the data, at 806, and before providing the first auxiliary component for retrieval, at 810, the method 800 may comprise, at 828, validating the data of the auxiliary memory of the first auxiliary component. Validation was previously described in connection with the figures describing the handling systems.

Optionally, the method 800 may further comprise deleting the data, at 830, from the auxiliary memory of the second auxiliary component. The data may be deleted after validating the data at 828, or if validation is not performed, after receiving an indication that the data transfer is complete. The indication may be a signal from the first auxiliary component or from the handling system controller.

The method 800 further comprises charging the rechargeable battery of the second auxiliary component, at 808. Said charging may be initiated immediately after receiving the second auxiliary component, at 804, or, as illustrated, after transmitting the data, at 806. Said charging may be initiated at any time after transmitting the data.

Optionally, the method 800 may comprise storing, at 824, the data from the auxiliary memory of the second auxiliary component at an external memory. Said storing may be performed concurrently or sequentially with transmission or transfer of the data to the first auxiliary component from the second auxiliary component. Said storing at the external memory may be performed while transmitting the data to the first auxiliary component and/or in response to receiving the user input at the transmit button. The data may be temporarily stored or buffered in a memory of handling system and from there transmitted to the external memory.

Optionally, the method 800 may comprise disinfecting, at 826, the second auxiliary component. Disinfection may be performed after transmitting the data to the auxiliary memory of the first auxiliary component, at 806, so as to not delay said transmission and, additionally, in case disinfection affects the auxiliary memory of the second auxiliary component. Although not illustrated, the method 800 may also comprise disinfection of the first auxiliary component. Disinfection of the first auxiliary component may be performed after receipt of the first auxiliary component, potentially while receiving the data from the second auxiliary component. In one variation, the first auxiliary component and/or the second auxiliary component are disinfected before transmission of the data to the first auxiliary component. Of course, the data may be stored in the memory of the handling system, as a precaution, and deleted therefrom after receipt by the first auxiliary component.

Optionally, the method 800 may further comprise receiving, at 812, a third auxiliary component, after providing the first auxiliary component for retrieval, and, optionally, after the first auxiliary component has been retrieved by a user or removed from the handling system position. Hence, the third auxiliary component may be received in the same position as the first auxiliary component was originally received.

Optionally, the method 800 may further comprise transmitting, at 814, the data from the auxiliary memory of the third auxiliary component to the auxiliary memory of the second auxiliary component.

Optionally, the method 800 may further comprise providing, at 818, the second auxiliary component for retrieval. Said providing may be performed after transmitting, at 814, the data from the auxiliary memory of the third auxiliary component to the auxiliary memory of the second auxiliary component.

Optionally, the method 800 may further comprise validating, at 829, the data of the auxiliary memory of the second auxiliary component. Said validating occurs after transmitting, at 814, the data to the auxiliary memory of the second auxiliary component and prior to providing, at 818, the second auxiliary component for retrieval. Validation was previously described in connection with the figures describing the handling systems.

Optionally, the method 800 may further comprise deleting, at 831, the data from the auxiliary memory of the third auxiliary component. e.g. after validating 829 the data, The data may be deleted after validating, at 829, the data or, if validation is not performed, after receiving an indication that the data transfer is complete. The indication may be a signal from the first auxiliary component or from the handling system controller.

Optionally, transmitting the data may be responsive to receiving, at 823, a user input to initiate the transfer of the data. The user input may be responsive to a transmit button actuated by the user. The data transmission of the data from the auxiliary memory of the third auxiliary component to the auxiliary memory of the second auxiliary component is initiated, at 814, in response to receiving the user input at 823.

Optionally, the method 800 may further comprise charging, at 816, the rechargeable battery of the third auxiliary component. Said charging may be initiated immediately after receiving the third auxiliary component, at 812, or after transmitting the data, at 814. Said charging may be initiated at any time after transmitting the data Optionally, the method 800 may further comprise storing, at 825, the data from the auxiliary memory of the third auxiliary component at the external memory. Said storing may be performed concurrently or sequentially with transmission or transfer of the data to the second auxiliary component from the third auxiliary component. Said storing at the external memory may be performed while transmitting the data to the second auxiliary component and/or in response to receiving the user input at the transmit button. The data may be temporarily stored or buffered in the memory of handling system and from there transmitted to the external memory.

Optionally, the method 800 may comprise disinfecting, at 827, the third auxiliary component. Disinfection may be performed after transmitting the data to the auxiliary memory of the second auxiliary component so as to not delay said transmission and, additionally, in case disinfection affects the auxiliary memory of the third auxiliary component. Disinfection of the third auxiliary component may be performed after receipt of the third auxiliary component.

Figure 22:
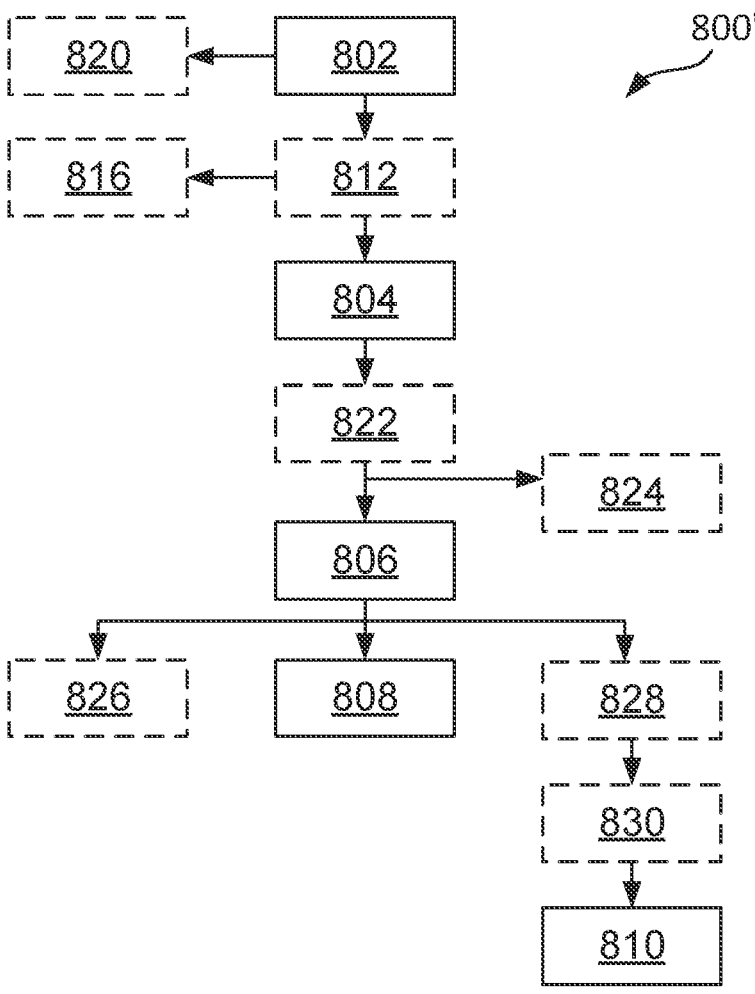

FIG. 22 is a block diagram of another embodiment of the method discussed above, denoted by numeral 800'. The functions of the method as seen in FIG. 22 are as described with reference to FIG. 21 but are performed in different order. In the present embodiment, the third auxiliary component is received, at 812, after receiving, at 802, the first auxiliary component but before receiving, at 804, the second auxiliary component. Therefore, the first and third auxiliary components may be charging before the second auxiliary component is received. If he handling system comprises a third component position/station and corresponding circuit, the order in which the three auxiliary components are receive is not relevant. If he handling system comprises two component positions, the third auxiliary component is removed to make room for the second auxiliary component, so the data transfer from the second auxiliary component to the first auxiliary component can proceed as shown.

In another variation, the handling system 700 only has one position and one charging circuit. In the present variation the handling system 700 may comprise a button operable to receive the user input to begin pairing. Thus, the auxiliary component being charged can receive the data wirelessly from another, paired, auxiliary component. Alternatively, a pairing button in the auxiliary component(s) may be used to initiate pairing, as described above. A charge indicator, as described above, can be included also. The handling system memory and controller can be included to transfer the data to an external memory. Such a handling system is more economical and may be placed in an operating room, where it is intended to charge auxiliary components used in the particular operating room, for example. The handling system 700 according to the present variation includes the first handling system communication interface 702A. The handling system 700 according to the present variation may include the disinfection area 718, adapted to disinfect an auxiliary component positioned therein as described above.

In a scenario where the battery of an auxiliary component is too low to allow transfer of data, it may need to be recharged to send or receive the data. The auxiliary memory of the auxiliary components may be non-transitory, allowing retrieval of the data even after the battery has been completely depleted.

B. Wearable Device.

Figure 23:
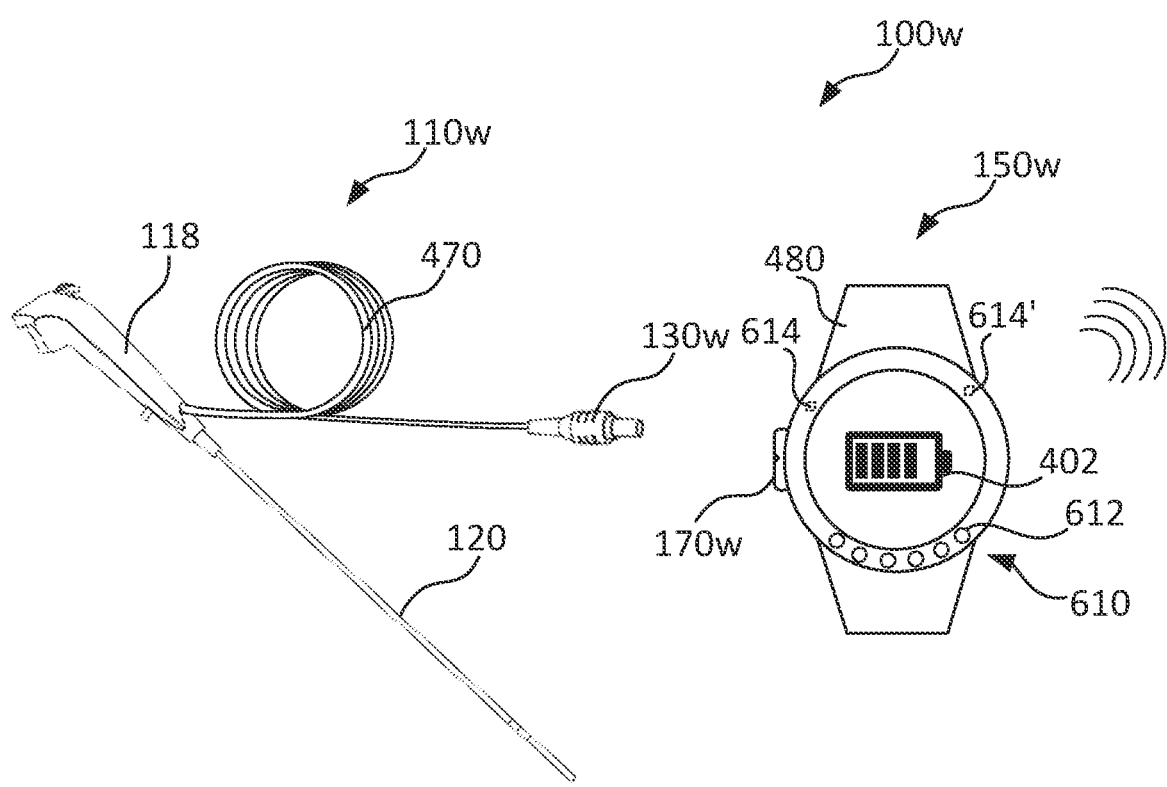
FIGS. 23 to 25 depict an embodiment of a visualization system comprising a wearable auxiliary component.

FIG. 23 illustrates another embodiment of the medical visualisation device 100, denoted by numeral 100w, wherein the auxiliary component 150w is a wearable device, such as a wristwatch. The auxiliary housing may be provided as the housing of the wearable device, i.e. the auxiliary housing and/or the device antenna may, thereby, be worn by the operator in a position that promotes line of sight with the VPA antenna. The VPA antenna and the device antenna may be positioned with line of sight there between.

The auxiliary component may be adapted for attachment to an operator of the medical visualisation system, such as to an arm of the operator or a head of the operator. Providing the auxiliary component as a wearable device allows convenient positioning of the auxiliary component and facilitates positioning of the auxiliary component at an increased distance from the patient, thereby reducing the risk of contaminating the auxiliary component, effectively reducing the risk of spreading infections.

The auxiliary component 150w comprises a wearing element 480, such as a strap, as illustrated. The wearing element 480 may comprise a belt, hook-n-loop patch, and any other means to removably attach the auxiliary component 150w onto a person. The auxiliary component 150w, being a wearable device, may be particularly advantageous if the auxiliary component 150w is to follow a certain person, e.g. if the auxiliary memory comprises personal data, such as patient data, operator data, or operator settings data.

In the illustrated example, the medical visualisation device 100w comprises a main component 110w with one or more flexible device wires 470. The flexible device wire(s) 470 extends between the main coupling part 130w and the handle 118 of the main component 110w. The main terminals of the main coupling part 130w may be electrically connected to the light emitter and the image sensor (e.g. located at the distal end of the insertion cord 120) through the flexible device wire(s) 470. The flexible device wire(s) 470 may be flexible to enable a user to bend the wires, such as to position the main coupling part 130w appropriately to attach to the auxiliary coupling part 170w of the auxiliary component 150w. The auxiliary and coupling parts may be, respectively, plugs and receptacles. Alternatively, they may be inductive couplings operable to transmit and receive data.

Magnets may be provided to the inductive couplings to physically couple them in the proper orientation and position relative to each other.

The main component 110w may look like prior art endoscopes on the outside. However, internally, it may be simplified by removing circuits needed to configure the image sensor, and such circuits may be included in the auxiliary component 150w, thereby reducing the cost and environmental impact of the disposable component of the medical visualization device. However, a prior art medical visualization device may be used as a main component, thereby providing flexibility and reducing supply-chain inventory and manufacturing complexity.

Figure 24:
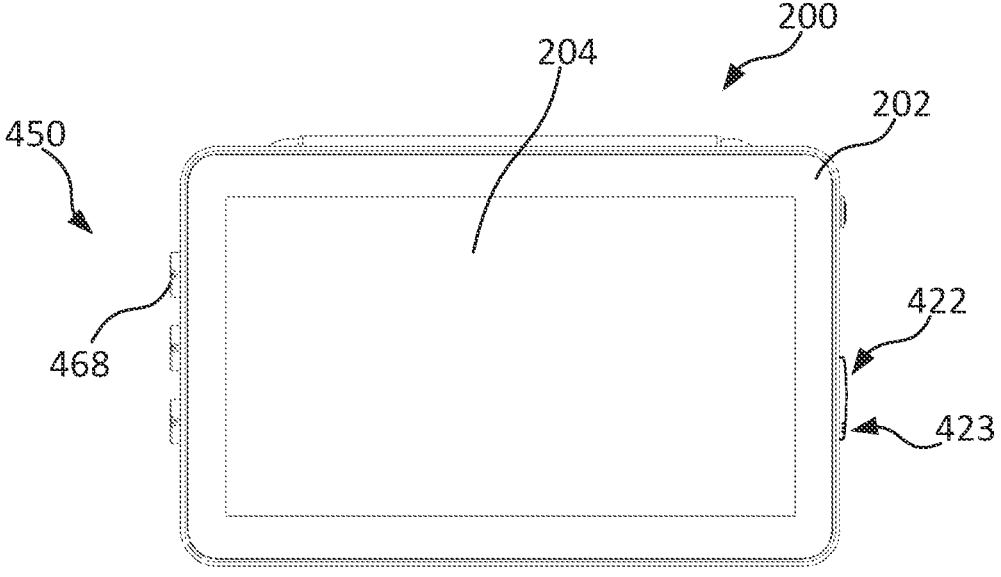

The auxiliary coupling part 170w of the auxiliary component 150w, adapted to couple with the main coupling part 130w of the main component 110w, may be similar to a coupling socket 468 of a VPA 200 shown in FIG. 24. Thereby, the operator may couple the main coupling part 130w directly to the VPA 200 by use of a coupling socket 468 of the VPA 200. Such coupling may be advantageous in case the auxiliary component 150w is not working properly and wireless transmission of the image data to the VPA (described above) is not working.

The auxiliary component 150w, as illustrated, comprises a battery indicator 402. The battery indicator 402 is indicative of remaining charge of the battery. The battery indicator 402 may be a graphical representation and/or one or more LEDs or other suitable means for providing an indication of remaining battery capacity. The battery indicator 402 may be provided using an e-ink display, e.g. such that the battery indicator 402 only uses power when updating the display, e.g. once every day when not being used. The battery indicator 402 may function as the battery indicator 162, 162' described with reference to FIGS. 4A and 4B.

The battery indicator 402 may be a button adapted to receive a user input. For example, the user may press the battery indicator 402, and the auxiliary device may be adapted to, in response to receiving the user input on the battery indicator 402 to indicate the present battery capacity. For example, the battery indicator 402 may, in response to receiving the user input, light up the battery indicator 402 in accordance with the current battery capacity. The battery indicator 402 may, in response to receiving the user input on the battery indicator 402, display the plurality of bars in accordance with the current battery capacity. Thus, battery power may be conserved by displaying the indication of battery capacity "on demand" when a user presses the battery indicator 402. Alternatively or additionally, when the battery capacity is critically low, the battery indicator 402 may indicate battery capacity, e.g. by flashing red, e.g. regardless of receiving or not receiving user input. The battery indicator 402 may be provided using an e-ink display, e.g. such that the battery indicator 402 only uses power when updating the display, e.g. once every day when not being used.

Although the battery indicator 402 is illustrated as being provided on top of the auxiliary device 150w, it should be understood that it may be positioned at other convenient positions, depending on the circumstances.

The auxiliary component 150w comprises a secondary auxiliary coupling part 610 having one or more secondary auxiliary terminals 612, e.g. electrically connected to the device controller and/or the one or more auxiliary terminals of the auxiliary coupling part 170w. The secondary auxiliary coupling part 610 may provide for a wired coupling with the VPA in case the wireless connection fails.

The secondary auxiliary coupling part 610 comprise secondary auxiliary magnetic elements 614, 614'. The secondary auxiliary magnetic elements 614, 614' may be adapted to align, and potentially orient, the secondary auxiliary terminals 612 with VPA terminals and couple the secondary auxiliary coupling part 610 with the VPA coupling part. The secondary auxiliary magnetic elements comprise a first secondary auxiliary magnetic element 614 and a second secondary auxiliary magnetic element 614'. The first secondary auxiliary magnetic element 614 and the second secondary auxiliary magnetic element 614' may have opposite polarity, e.g. the first secondary auxiliary magnetic element 614 may be north, and the second secondary auxiliary magnetic element 614' may be south.

Thus, by utilizing magnetic elements at the main coupling part and the auxiliary coupling part the user may easily attach the main coupling part 130w and the auxiliary coupling part 170w simply by positioning the main coupling part 130w onto the auxiliary coupling part 170w.

FIG. 24 illustrates an embodiment of a variation of the VPA 200. The VPA 200 in the present variation further comprises a VPA coupling part 450 including a coupling socket 468 configured to receive the main coupling part 130w. The VPA coupling part 450 is adapted to couple with the main coupling part 130w of the main component 110w. Thus, a wired backup solution may be provided in case wireless transmission between the medical visualisation device 100w and the video processing apparatus 200 is not possible, e.g. if the battery of the medical visualisation device 100 is empty.

The VPA may comprise a VPA charging circuit. The VPA charging circuit may be adapted to charge the battery of the auxiliary component, when the auxiliary component is engaged with the VPA As will be explained later with reference to FIGS. 25 and 26, the coupling socket 468 may also receive a coupling plug 466 (shown in FIGS. 27 and 28) of the VPA coupling part 450. The VPA coupling part 450 comprises one or more VPA terminals 452. The VPA terminal(s) 452 are adapted to connect to the main terminal(s) 132w of the main coupling part 130w, when the VPA coupling part 450 is coupled with the main coupling part 130w. The VPA controller may be electrically connected to the one or more VPA terminal(s) 452. Furthermore, the VPA controller may be adapted to receive the image data, via the VPA coupling part 450, from the image sensor of the medical visualisation device 100w and cause the display 204 to display a live representation of the image data.

The VPA 200 in the present variation comprises a component socket 422 adapted to engage with the auxiliary component 150w. For example, the component socket 422 may be adapted to store and/or charge the auxiliary component 150w. The component socket 422 may also or alternatively be adapted to pair the transceivers of the VPA 200 and the auxiliary component 150w, similarly as described with reference to FIGS. 13 and 14. The component socket 422 may comprise one or more terminals 423, which may comprise charging terminals and/or pairing terminals. The auxiliary component 150w may be held in place in the component socket 422 by magnetic elements, as described with reference to FIGS. 13 and 14.

The auxiliary component 150w may comprise the auxiliary user interface 730. The auxiliary user interface may comprise a button, a touch screen or other suitable input device. Buttons and user interfaces in watches are well known and will not be described further. Their functionality is as described above.

Figure 25:
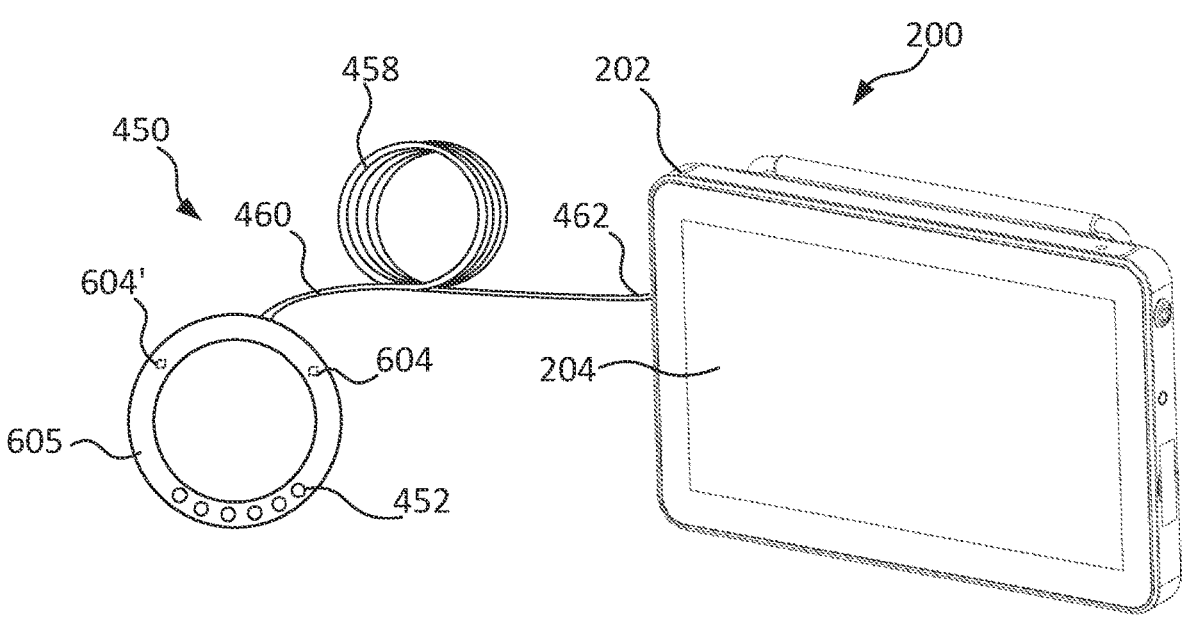

FIG. 25 illustrates another variation of the VPA coupling part 450 adapted to couple with the secondary auxiliary coupling part 610 shown in FIG. 23. The one or more VPA terminals 452 are adapted to connect to the one or more secondary auxiliary terminals 612 of the secondary auxiliary coupling part 610. The VPA controller may be adapted to, e.g. when the VPA coupling part 450 is coupled with the secondary auxiliary coupling part 610, receive the image data and/or the encoded image data from the auxiliary component 150w.

In the present embodiment the VPA coupling part 450 comprises one or more wires 458 extending between a distal end 460 and a proximal end 462. At the proximal end 462, the VPA coupling part is connected to the circuits of the VPA located inside the housing 202, such as the VPA controller, memory, etc. The connection may be direct or, preferably, via the coupling socket 468, which is configured to receive the coupling plug 466 of the VPA coupling part 450. The VPA terminal(s) 452 are arranged at the distal end 460 of the one or more wires 458 and are electrically connected to the VPA controller through the one or more wires 458. The wire(s) 458 may be flexible to enable a user to bend the wires, such as to arrange the VPA coupling part appropriately to attach to the secondary auxiliary coupling part. The wires 458 may be substituted by a circuit board or a rigid circuit.

In the present embodiment, the VPA coupling part 450 comprises a support structure 605 holding VPA magnetic elements 604, 604' and the VPA terminals 452. The secondary auxiliary magnetic elements 614, 614' (see FIG. 23) are thus aligned to couple with the VPA magnetic elements 604, 604', and the secondary auxiliary terminals 612 are aligned to couple with the VPA terminals 452. Thus, the user may easily attach the VPA coupling part 450 and the secondary auxiliary coupling part 610 by positioning the support structure 605 of the VPA coupling part 450, comprising the VPA terminals 452 and the VPA magnetic elements 604, 604', onto the secondary auxiliary coupling part 610. Some of the magnetic elements are magnets and some may be metal portions that are attracted to the magnets.

Figure 26:
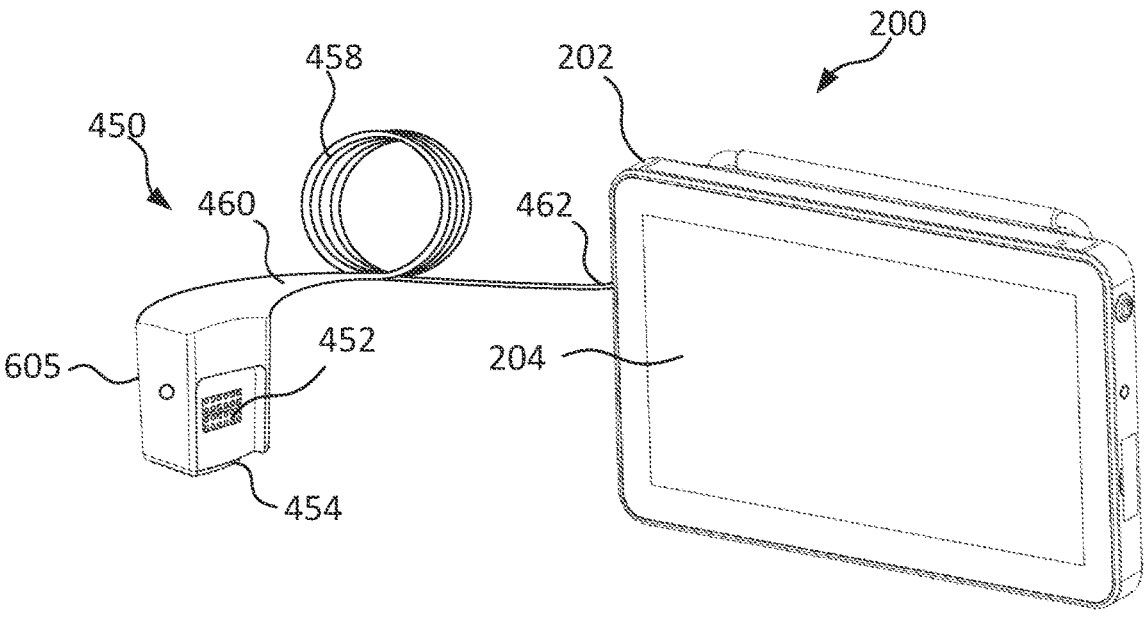
FIG. 26 depicts an embodiment of a video processing apparatus configured to make an electrical, or physical, connection with an auxiliary component of a medical visualization device, such as the auxiliary component shown in FIGS. 3A and 3B.

FIG. 26 illustrates a further variation of the VPA coupling part 450 that illustrates that the VPA coupling part 450 can also be applicable to non-wearable auxiliary components. In the present embodiment, the VPA coupling part 450 is adapted to couple with the main coupling part 130 of the main component 110 (see FIGS. 3A and 3B) of the auxiliary component 150, which is not a wearable device. The VPA coupling part 450 comprises a VPA primary engagement member 454 adapted to engage with the main primary engagement member of the main coupling part. The VPA primary engagement member 454 may be a cooperating member of the support structure 605, such as a protrusion, as illustrated, or a recess, or another suitable engagement member. Thus, a wired backup solution may be provided in case wireless transmission between the medical visualisation device 100 and the video processing apparatus 200 is not possible, e.g. if the battery of the medical visualisation device 100 is empty. The support structure 605 supports the VPA terminals 452 and the VPA primary engagement member 454 suitably positioned to mechanically couple with the main primary engagement member of the main coupling part 130.

Figure 27:
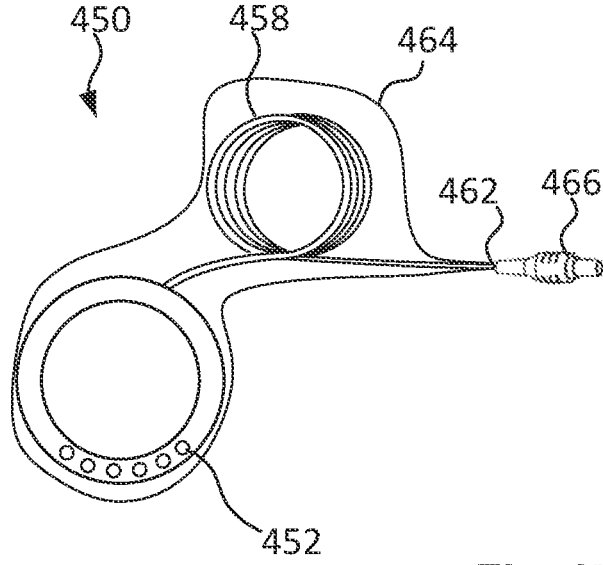
FIGS. 27 and 28 depicts an embodiment of a sealing package.
Figure 28:
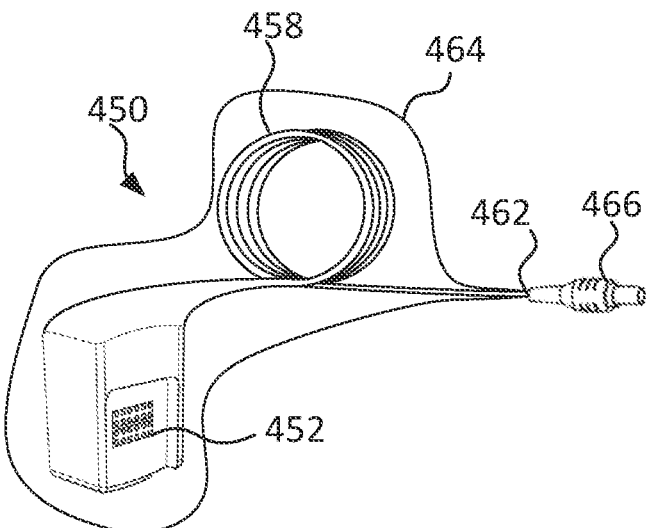

FIGS. 27 and 28 illustrate a sealing package 464. The VPA terminals 452 may be enclosed in the sealing package 464 and then the sealing package 464 may be closed to seal the VPA terminals 452. Also shown is the coupling plug 466 discussed above, for coupling the VPA wires 458 to the VPA 200. The coupling plug 466 may be arranged outside the sealing package 464, such as to allow connecting the coupling plug 466 with the coupling socket 468 of the VPA 200. The VPA coupling part 450 may thereby be connected before needed for the procedure, and stay sterile, and when needed the operator only needs to open the sealing package 464 and couple the VPA coupling part 450 with the secondary auxiliary coupling part of the auxiliary component. The VPA coupling part 450, e.g. the coupling plug 466, may indicate, e.g. by light or sound, if the parts inside the sealing package 466 are not properly working, prompting replacement of VPA coupling part 450. A diagnostic test may be performed, which is a self-test of the electronic components. The self-test is performed by the VPA and may comprise continuity and impedance measurements and comparison of the measurements to expected values. The VPA 200, such as VPA controller, may notify a user, via a message on the display, if the VPA coupling part 450 is defective.

Figure 29:
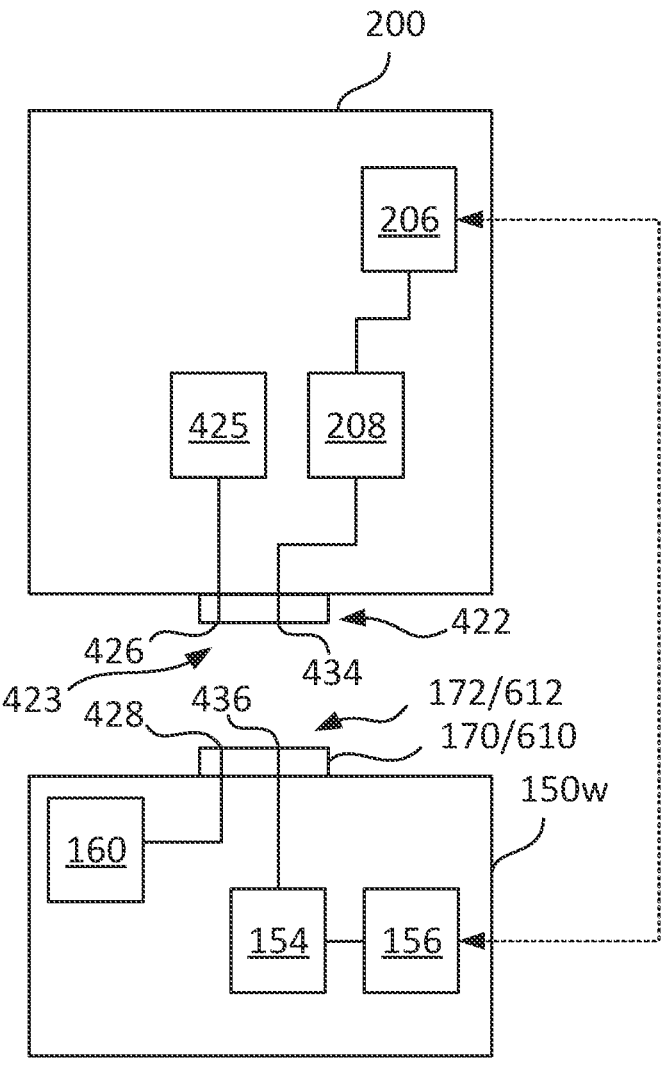
FIGS. 29 and 30 are schematic block diagrams of the embodiment of the video processing apparatus and the medical visualisation device of FIGS. 23 to 25.
Figure 30:
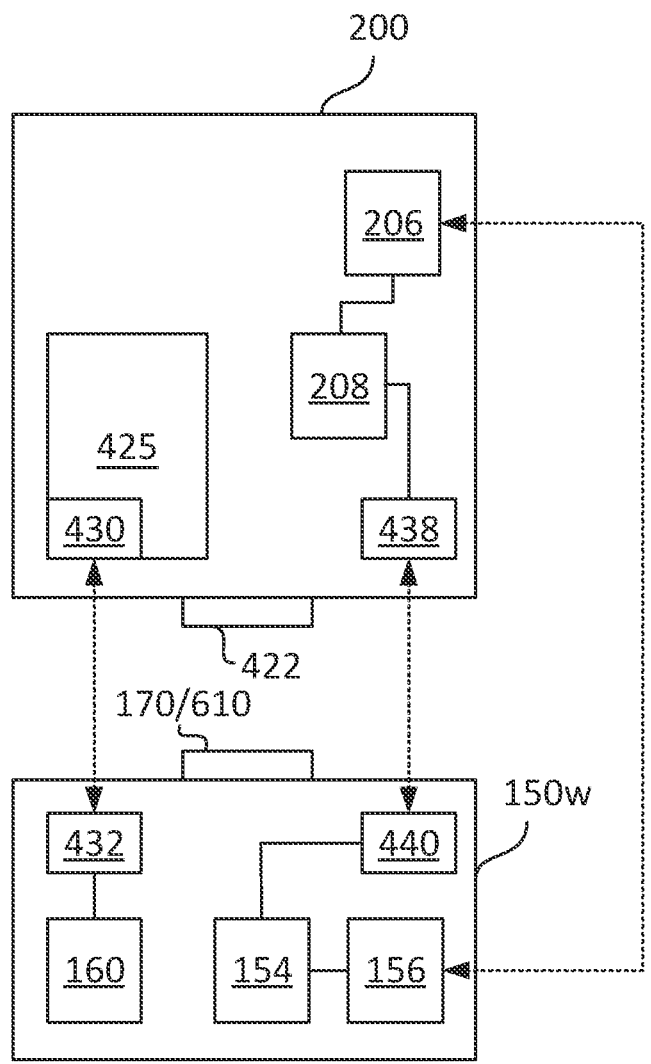

FIGS. 29 and 30 are schematic block diagrams of the VPA 200 and auxliary component 150w. These diagrams are the same as FIGS. 15 and 16, except for the "w" designation indicating that the auxiliary component 150w is wearable and the addition of numerals 610/612. As shown and described with reference to FIGS. 15 and 16, the VPA 200 and auxliary component 150w may establish short-range and inductive wireless connections.

Figure 31:
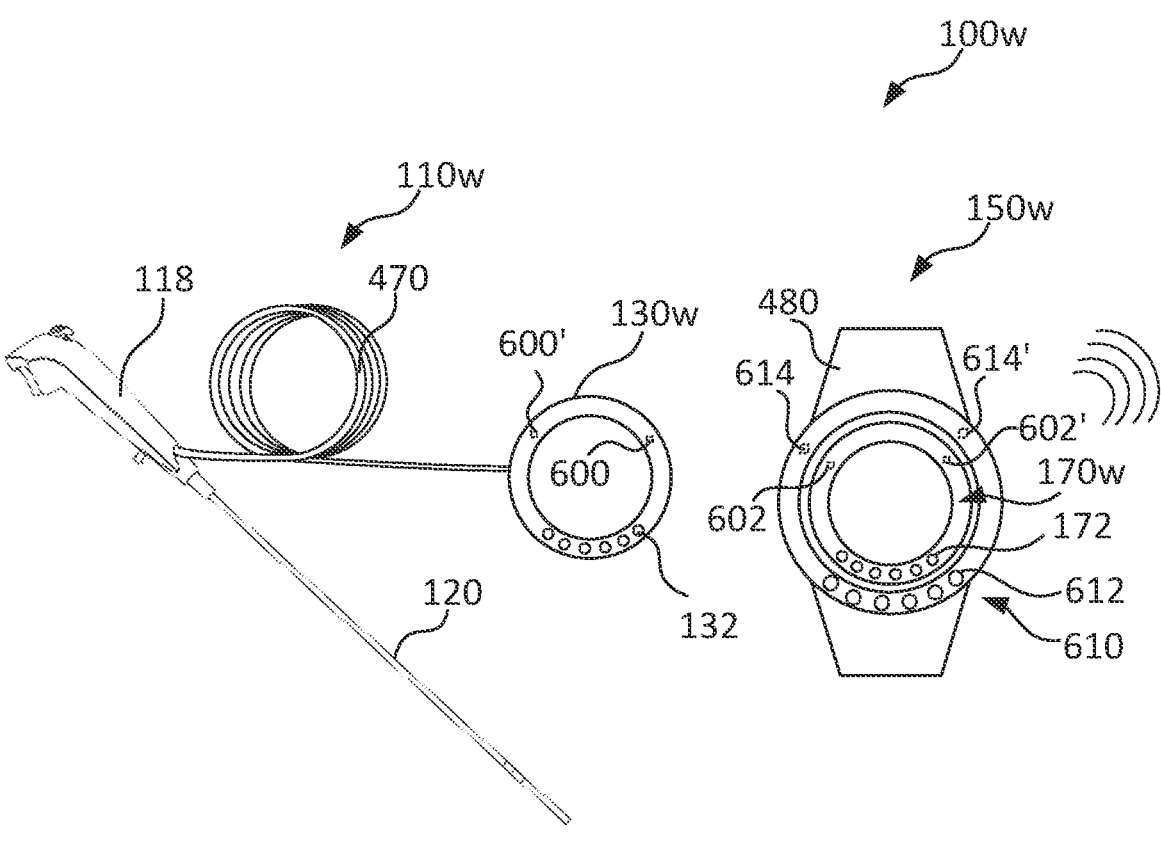
FIG. 31 depicts a variation of the embodiment of the wearable auxiliary component depicted in FIG. 23.

FIG. 31 illustrates another embodiment of the medical visualisation device 100w, wherein the auxiliary component 150w is a wearable device, such as a wristwatch, and is similar in most respects as the embodiment of the auxiliary component 150w depicted in FIG. 23. The embodiments differ in the manner in which the auxiliary component 150w couples with the main component 110w. More specifically, the main coupling part 130w in FIG. 23 is a plug connector that is received by the auxiliary coupling part 170w of the auxiliary component 150'. By contrast, the main coupling part 130w in FIG. 31 comprises a magnetic coupling that couples magnetically with the auxiliary coupling part 170w of the auxiliary component 150'. The magnetic coupling was previously described with reference to FIGS. 23 and 25, except that there it was used to connect the auxiliary component 150' to the VPA whereas here it is used to connect the main component 110'.

The main terminals of the main coupling part 130w may be electrically connected to the light emitter and the image sensor (e.g. located at the distal end of the insertion cord 120) through the flexible device wire(s) 470. The flexible device wire(s) 470 may be flexible to enable a user to bend the wires, such as to position the main coupling part 130w appropriately to attach to the auxiliary coupling part 170w of the auxiliary component 150w.

The auxiliary component 150w comprises a battery indicator 402 indicative of remaining charge of the battery. The battery indicator 402 may be as described above with reference to FIG. 23, such as a button adapted to receive a user input or an e-ink display.

The auxiliary component 150w comprises the secondary auxiliary coupling part 610 with the one or more secondary auxiliary terminals 612 electrically connected to the device controller The secondary auxiliary coupling part 610 may provide for a wired coupling with the main component 110w in case the wireless connection fails.

The auxiliary coupling part 170w of the auxiliary component 150w comprises magnetic elements 602, 602' that function as the magnetic elements 614, 614'. It also comprises the auxiliary terminals 172. The magnetic elements 602, 602' and the auxiliary terminals 172 are mounted on a support structure. As shown, the support structure has a hollow disc shape that fits inside a hollow disc supporting the magnetic elements 614, 614'. Of course the magnetic elements 602, 602' and the magnetic elements 614, 614' and the auxiliary terminals 172 can be supported in any suitable manner.

The magnetic elements 602, 602' are adapted to align with magnetic elements 600, 600' of the main coupling part 130w, which in this case also includes terminals 132, which are positioned to align with the auxiliary terminals 172. Thus, although the coupling mechanism in the present embodiment differs from the one in FIG. 23, both embodiments provide an alternative way to electrically connect the main component 130w and the auxiliary component 150w. The main magnetic elements 600, 600' comprise a first main magnetic element 600 and a second main magnetic element 600'. The auxiliary magnetic elements 602, 602' comprise a first auxiliary magnetic element 602 and a second auxiliary magnetic element 602'. The first main magnetic element 600 may have a primary polarity, e.g. north, and the second main magnetic element 600' may have a secondary polarity, e.g. south, i.e. the secondary polarity may be opposite the primary polarity to provide orientation. The first auxiliary magnetic element 602 may have a polarity opposite the first main magnetic element 600, e.g. the secondary polarity, i.e. to enable attraction of the first main magnetic element 600 and repulsion of the second main magnetic element 600'. The second auxiliary magnetic element 602' may have a polarity opposite the second main magnetic element 600', e.g. the primary polarity, i.e. to enable attraction of the second main magnetic element 600' and repulsion of the first main magnetic element 600. Orientation in this manner may be provided in any of the magnetic couplings disclosed herein.

Figure 32:
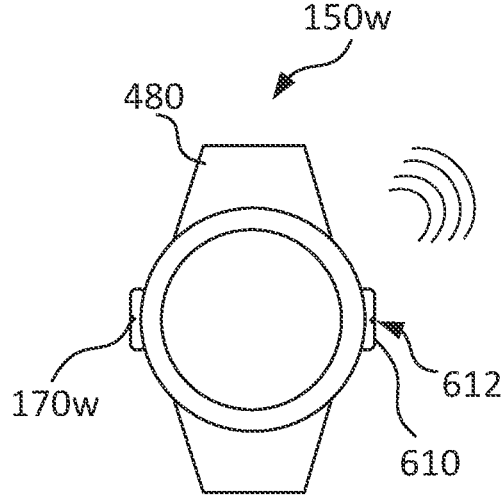
FIG. 32 depicts a variation of the embodiment of a wearable auxiliary component and the video processing apparatus of FIGS. 23 to 25.
Figure 32:
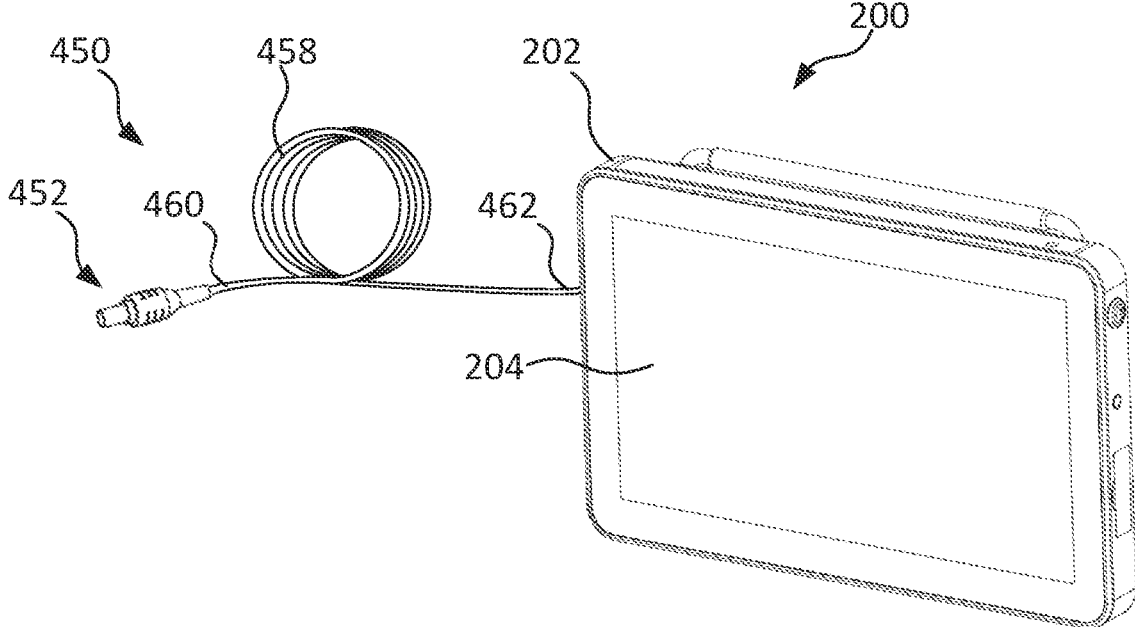

FIG. 32 illustrates yet another embodiment of the medical visualisation device 100w, wherein the auxiliary component 150w is a wearable device, such as a wristwatch. The main component 110 is the same as depicted in FIG. 23. The main component 110w comprises flexible device wires 470 extending between the main coupling part 130w and the handle 118 of the main component 110w. The main terminals of the main coupling part 130w may be electrically connected to the light emitter and the image sensor (e.g. located at the distal end of the insertion cord 120) through the wires 470. The auxiliary and coupling parts 170w, 130w may be, respectively, a receptacle and a plug, as shown, or vice versa.

The secondary auxiliary terminals 612 of the secondary auxiliary coupling part 610 with the VPA coupling part may be, respectively, a receptacle and a plug, as shown, or vice versa. The receptacle receives a plug 452 of the VPA coupling part 450. The VPA coupling part 450 is a variation of the VPA coupling part 450 shown in FIGS. 25 and 26, and except for the connection means, functions in the same manner as described there.

Variations of the VPA 200 can be provided with various features of the VPA 200 but including or excluding other features. For example, it might not be desirable to provide a video display screen with a touch screen, or it might be desirable to omit a display screen altogether. Omission of the display screen might be beneficial to take advantage of evolving video display technologies which improve resolution and reduce cost. Provision of exchangeable medical device interfaces allows for adoption of evolving image sensor and endoscope technologies, thus use of existing or future-developed external video displays could allow presentation of higher resolution or otherwise improved video. Use of external video displays could also leverage existing capital investments.

A positioning interface, or interface, functions to control the position of the insertion cord. The handle 118 is an example of a positioning interface and, unless stated otherwise, the terms are used interchangeably. The positioning interface may also provide the steering controls, e.g. knobs, levers, buttons, and the like, to steer the field of view of the image sensor and the elevator controls. Alternatively, a different positioning interface can be provided that is connected to the insertion cord and is detachably connected to a robotic arm. The insertion cord thus extends from the robotic arm, and the medical visualization device is detachable from the robotic arm. The robotic arm responds to signals, including voice commands from an operator, to rotate, translate, and otherwise position the proximal end of the insertion cord, as an operator would do manually. The positioning interface can include control actuators, including manual control actuators. Alternatively or additionally, control actuators can be provided in or on the robotic arm or by the robotic system including the robotic arm, thereby potentially reducing the cost of the medical visualization device. Example control actuators include single axis actuators, including linear motion actuators. A linear motion actuator may comprise a threaded rod coupled to a threaded nut portion, in which a motor rotates the rod to translate the nut portion.

Exemplary embodiments of the present disclosure are set out in the following items:

1. A medical visualisation device having: an image sensor adapted to generate image data indicative of a view from the medical visualisation device, a light emitter adapted to provide illumination of the view, a device processing unit adapted to receive the image data from the image sensor and encode the image data to provide encoded image data based on the image data, a device transceiver adapted to communicate with a VPA transceiver of a VPA, the device transceiver being adapted to receive the encoded image data from the device processing unit and transmit the encoded image data using a downstream data channel from the device transceiver to the VPA wireless communication module, and wherein the device transceiver is adapted to receive settings data using an upstream data channel from the VPA transceiver to the device wireless communication module.

2. Medical visualisation device according to item 1, wherein the upstream data channel is limited to less than 500 bits per second, such as less than 250 bits per second, such as less than 100 bits per second, such as less than 80 bits per second.

3. Medical visualisation device according to any of the preceding items, wherein the device processing unit is adapted to receive the settings data from the device transceiver and adjust settings of one or more components of the medical visualisation device based on the settings data.

4. Medical visualisation device according to item 3, wherein the one or more components include the image sensor and the device processing unit is adapted to adjust settings of the image sensor, e.g. including colour, contrast, gain, and/or exposure settings, based on the settings data.

5. Medical visualisation device according to any of items 3-4, wherein the one or more components include the light emitter and the device processing unit is adapted to adjust settings of the light emitter, e.g. including current, brightness and/or PWM settings.

6. Medical visualisation device according to any of the preceding items, wherein the communication between the device transceiver and the VPA transceiver is in accordance with Wireless HD specification.

7. Medical visualisation device according to any of the preceding items, wherein the device transceiver is a wireless HD chipset.

8. Medical visualisation device according to any of the preceding items, wherein the image data has a first resolution, such as at least 400×400 pixels, and is generated at a first frame rate, such as at least 30 frames per second.

9. Medical visualisation device according to any of the preceding items, wherein the encoded image data uses a format with a total number of bits, such as 24 bits, and wherein a first portion of the total number of bits is used to encode the image data, wherein the first portion of the total number of bits is less than the total number of bits.

10. Medical visualisation device according to item 9, wherein the first portion of the first number of bits is 10 bits.

11. Medical visualisation device according to any of items 9-10 wherein a second portion of the total number of bits is used to embed additional information, such as battery status or settings information.

12. Medical visualisation device according to any of the preceding items, wherein the device transceiver is adapted to communicate with the VPA transceiver using a radio frequency at more than 10 GHz.

13. Medical visualisation device according to item 12, wherein the radio frequency is between 57-66 GHz, such as between 57-64 GHz, such as between 57.05-64 GHz, such as between 59-64 GHz, such as between 59.4-63.56, such as between 59.4-62.9 GHz.

14. Medical visualisation device according to any of the preceding items being an endoscope.

15. Medical visualisation device according to any of the preceding items, wherein the medical visualisation device comprises a handle and an insertion cord extending from the handle to a distal tip, and wherein the view from the medical visualisation device is a view from the distal tip of the insertion cord.

16. Medical visualisation device according to item 15, wherein the handle comprises a control button adapted to receive an input in a first input direction, and wherein the touch input in the first input direction causes a bending section of the insertion cord to bend in a first bending direction.

17. Medical visualisation device according to any of items 1-13 being a laryngoscope.

18. Medical visualisation device according to any of the preceding items comprising a main component comprising the image sensor and the light emitter, wherein the main component is disposable, and the device processing unit and the device transceiver are provided in an auxiliary component adapted to be coupled to the main component, wherein the auxiliary component is reusable.

19. Medical visualisation device according to item 18 as dependent on any of items 15 or 16, wherein the main component comprises the handle and the insertion cord.

20. Medical visualisation device according to any of the preceding items, wherein the device transceiver comprises a device antenna.

21. Medical visualisation device according to any of the preceding items comprising a battery adapted to power the medical visualisation device.

22. Medical visualisation device according to item 21 as dependent on item 18, wherein the battery is provided in the auxiliary component.

23. Medical visualisation device according to any of items 21 or 22, wherein the battery is a rechargeable battery.

24. A VPA operable to receive image data from a medical visualisation device, the VPA comprising: a first housing, a VPA transceiver adapted to communicate with a device transceiver of the medical visualisation device, the VPA transceiver being adapted to receive encoded image data using a downstream data channel from the device transceiver to the VPA wireless communication module, and wherein the VPA transceiver is adapted to transmit settings data using an upstream data channel from the VPA transceiver to the device wireless communication module, a VPA controller adapted to receive the encoded image data from the VPA transceiver and decode the encoded image data and cause a display to display a live representation of the image data.

25. VPA according to item 24 comprising the display, e.g. accommodated in the first housing.

26. VPA according to any of items 24-25, wherein the VPA controller is adapted to provide the settings data based on the image data to adjust settings of one or more components of the medical visualisation device.

27. VPA according to any of items 24-26, wherein the VPA transceiver comprises a VPA antenna, wherein the VPA antenna is positioned external to the first housing.

28. VPA according to item 27, wherein the VPA antenna is adapted to be positioned at a distance from the first housing of more than 2 meters.

29. VPA according to any of items 27 or 28, wherein the VPA antenna is adapted to be positioned above an operating setting in an operating room, such as at the ceiling of the operating room.

30. VPA according to any of items 27-29, wherein the VPA antenna is positioned above the first housing.

31. A medical visualisation system comprising a first medical visualisation device according to any of items 1-23 and a VPA according to any of items 24-30.

32. Medical visualisation system according to item 31 comprising a second medical visualisation device according to any of items 1-23, wherein the first medical visualisation device and the second medical visualisation device are different.

33. Medical visualisation system according to item 32, wherein the first medical visualisation device is configured for a first clinical purpose and the second medical visualisation device is configured for a second clinical purpose.

34. Medical visualisation system according to any of items 32-33, wherein the image sensor of the first medical visualisation device is a first image sensor type and the image sensor of the second medical visualisation device is a second image sensor type.

35. Medical visualisation system according to any of items 31-34, at least as dependent on items 20 and 27, wherein the VPA antenna and the device antenna is positioned with line of sight there between.

41. A medical visualisation system comprising a first medical visualisation device for performing a medical visualisation procedure and a VPA, wherein a main component of the first medical visualisation device comprises: an image sensor adapted to generate image data indicative of a view from the main component, a light emitter adapted to provide illumination of the view, and a main coupling part having one or more main terminals electrically connected to the light emitter and the image sensor, the VPA comprises: a first housing, one or more VPA communication interfaces including a VPA wireless communication module, a VPA controller, and a VPA memory, the VPA being operable to cause a display to display a live representation of the image data, the medical visualisation system further comprising an auxiliary component comprising: an auxiliary coupling part adapted to couple with the main coupling part, the auxiliary coupling part comprising one or more auxiliary terminals adapted to connect to the one or more main terminals of the main coupling part, when the auxiliary coupling part is coupled with the main coupling part, a device processing unit electrically connected to the one or more auxiliary terminals and adapted to receive the image data from the image sensor, when the auxiliary component is coupled to the main component, and encode the image data to provide encoded image data based on the image data, one or more auxiliary communication interfaces including a device transceiver connected to the processing unit and adapted to communicate with the VPA transceiver of the VPA, the device transceiver being adapted to receive the encoded image data from the device processing unit and transmit the encoded image data using a downstream data channel to the VPA transceiver of the VPA, and an auxiliary memory storing initial data, wherein the auxiliary component is configured to transmit the initial data to the VPA, and wherein the VPA controller is adapted to receive the initial data and adjust one or more parameters of the medical visualisation system based on the initial data.

42. Medical visualisation system according to item 41, wherein the VPA comprises the display, e.g. accommodated in the first housing.

43. Medical visualisation system according to any one of items 41-42, wherein the initial data comprises patient data, and wherein the VPA controller is adapted to associate the patient data with the image data.

44. Medical visualisation system according to any one of items 41-43, wherein the initial data comprises operator data indicative of an operator performing the medical visualisation procedure, and wherein the VPA controller is adapted to associate the operator data with the image data.

45. Medical visualisation system according to any one of items 41-44, wherein the VPA controller or the device processing unit stores an image data file in the auxiliary memory in response to receipt of a user input signal indicative of a user activating an image capture button, wherein the image data file corresponds to the image data received when the image capture button was activated.

46. Medical visualisation system according to item 45, wherein the VPA displays with the display one or more VPA buttons comprising the image capture button, and/or wherein the main component comprises one or more device buttons comprising the image capture button.

47. Medical visualisation system according to any of items 45-66 as dependent on any of items 43 or 44, wherein the VPA controller is adapted to associate the patient data and/or the operator data with the image data file.

48. Medical visualisation system according to any one of items 41-47, wherein the initial data comprises operator setup data associated with the operator performing the medical visualisation procedure.

49. Medical visualisation system according to item 48, wherein the operator setup data includes image parameters including one or more of settings of hue, saturation, brightness, contrast, and sharpness, and wherein the VPA controller in response to receiving the initial data adjusts image parameters of the live representation of the image data displayed on the display in accordance with the image parameters of the operator setup data.

50. Medical visualisation system according to any of items 48-49 comprising one or more buttons adapted to receive user inputs, and wherein the operator setup data includes button settings indicative of functions assigned to one or more of the buttons, and wherein the VPA controller in response to receiving the initial data assigns functions to the one or more of the buttons in accordance with the button settings of the operator setup data.

51. Medical visualisation system according to any of items 48-50, wherein the VPA controller is adapted to perform tasks based on spoken inputs, and the operator setup data includes voice control data associated with the operator performing the medical visualisation procedure, and wherein the VPA controller, after receiving the initial data, identifies tasks to be performed based on the spoken inputs and the voice control data of the initial data.

52. Medical visualisation system according to any one of items 41-51, wherein the VPA controller is adapted to store new operator setup data in the auxiliary memory based on a current set of settings of the VPA.

53. Medical visualisation system according to item 52, wherein the VPA controller stores the new operator setup data in the auxiliary memory in response to receipt of a user input signal indicative of a user requesting storing of the current set of settings, wherein optionally the user requesting storing of the current set of settings includes pressing a predetermined button for more than a predetermined time.

54. Medical visualisation system according to any one of items 41-53, wherein the one or more VPA communication interfaces comprises exposed electrical terminals to contact corresponding exposed electrical terminals of the one or more auxiliary communication interface, and wherein the VPA controller is adapted to receive the initial data via the exposed electrical terminals of the one or more VPA communication interfaces.

55. Medical visualisation system according to any one of items 41-54, wherein the one or more VPA communication interfaces comprises a short-range communication circuit adapted to inductively communicate with a corresponding short-range communication circuit of the one or more auxiliary communication interface, and wherein the VPA controller is adapted to receive the initial data via the short-range communication circuit of the one or more VPA communication interfaces.

56. Medical visualisation system according to any one of items 41-55, wherein the device processing unit is adapted to encode the initial data together with the image data in the encoded image data, and wherein the initial data is transmitted to the VPA embedded in the encoded image data.

57. Medical visualisation system according to any one of items 41-56, wherein the device transceiver transmits the initial data to the VPA transceiver of the VPA during an initialisation procedure before encoding the image data and transmitting the encoded image data.

58. Medical visualisation system according to any one of items 41-57, wherein the auxiliary component comprises a battery electrically connected to the one or more auxiliary terminals, the device processing unit and the device wireless communication module, the battery being adapted to power the device processing unit and the device wireless communication module, the battery further being adapted to power the image sensor and light emitter of the main component when the auxiliary component is coupled to the main component.

59. Medical visualisation system according to any one of items 41-58, comprising a second medical visualisation device, and wherein a main component of the second medical visualisation device comprises: an image sensor adapted to generate image data indicative of a view from the main component of the second medical visualisation device, a light emitter adapted to provide illumination of the view, and a main coupling part having one or more main terminals electrically connected to the light emitter and the image sensor, the main coupling part of the second medical visualisation device being adapted to couple with the auxiliary coupling part of the auxiliary component.

60. Medical visualisation system according to item 59, wherein the first medical visualisation device is configured for a first clinical purpose and the second medical visualisation device is configured for a second clinical purpose.

61. Medical visualisation system according to any of items 59-60, wherein the image sensor of the first medical visualisation device is a first image sensor type and the image sensor of the second medical visualisation device is a second image sensor type.

71. A handling system for handling auxiliary components, including a first auxiliary component and a second auxiliary component, of a medical system, wherein each auxiliary component is adapted to be coupled to a respective main component, and wherein each auxiliary component comprises a rechargeable battery adapted to power electronic components of the auxiliary component and of the respective main component, each auxiliary component further comprising an auxiliary memory and an auxiliary communication interface, the handling system comprising a first system communication interface adapted to couple with the auxiliary communication interface of the first auxiliary component and a second system communication interface adapted to couple with the auxiliary communication interface of the second auxiliary component, the handling system being adapted to, via the first system communication interface and/or the second system communication interface, cause transmittal of data from the auxiliary memory of the second auxiliary component to the auxiliary memory of the first auxiliary component, the handling system further comprises a system charging circuit adapted to charge the rechargeable battery of the second auxiliary component.

72. Handling system according to item 71, wherein the handling system comprises a system processing unit, and wherein to transmit the data the system processing unit is adapted to, via the second system communication interface, read or receive the data of the auxiliary memory of the second auxiliary component, and, via the first system communication interface, write or transmit the data from the auxiliary memory of the second auxiliary component to the auxiliary memory of the first auxiliary component.

73. Handling system according to item 71, wherein each of the auxiliary components comprises a short-range communication circuit, and wherein the handling system is adapted to, via the first system communication interface and/or the second system communication interface, to cause transmittal of the data from the auxiliary memory of the second auxiliary component to the auxiliary memory of the first auxiliary component by wireless communication between the short-range communication circuit of the first auxiliary component and the short-range communication circuit of the second auxiliary component.

74. Handling system according to any one of items 71-73, wherein the system charging circuit includes a first system charging circuit adapted to charge the rechargeable battery of the first auxiliary component and a second system charging circuit adapted to charge the rechargeable battery of the second auxiliary component.

75. Handling system according to any one of items 71-74, comprising a plurality of component positions including a first component position adapted to receive the first auxiliary component and a second component position adapted to receive the second auxiliary component.

6. Handling system according to any one of items 71-75, comprising a first transmit button, and wherein the handling system is adapted to cause the transmittal of data from the auxiliary memory of the second auxiliary component to the auxiliary memory of the first auxiliary component, in response to a user pressing the first transmit button.

77. Handling system according to any one of items 71-76, comprising a second transmit button, and wherein the handling system is adapted to cause transmittal of data from the auxiliary memory of the first auxiliary component to the auxiliary memory of the second auxiliary component, in response to a user pressing the second transmit button.

78. Handling system according to any one of items 71-77, comprising one or more battery indicators adapted to display a visual indication of estimated battery capacity of the rechargeable battery of the first auxiliary component and/or the second auxiliary component.

79. Handling system according to item 78, wherein the one or more battery indicators includes a first battery indicator adapted to display a visual indication of estimated battery capacity of the rechargeable battery of the first auxiliary component and a second battery indicator adapted to display a visual indication of estimated battery capacity of the rechargeable battery of the second auxiliary component.

80. Handling system according to any one of items 71-79, wherein the handling system is connectable to an external memory, and wherein the handling system is adapted to, via the second system communication interface, to read or receive the data from the auxiliary memory of the second auxiliary component and store the data at the external memory.

81. Handling system according to any one of items 71-80, comprising a disinfection area adapted to disinfect an auxiliary component positioned in the disinfection area, and wherein the handling system is adapted to, after causing transmittal of the data from the auxiliary memory of the second auxiliary component to the auxiliary memory of the first auxiliary component, position the second auxiliary component in the disinfection area.

82. Handling system according to item 81 wherein the disinfection area comprising a chamber wherein an auxiliary component is subjected to ultraviolet radiation, heat, steam, gas and/or a disinfectant.

83. Handling system according to any one of items 71-82, comprising a conveyor for repositioning the auxiliary components.

84. Handling system according to any one of items 71-83, adapted to validate the data of the auxiliary memory of the first auxiliary component after transmittal of the data to the auxiliary memory of the first auxiliary component.

85. Handling system according to any one of items 71-84, adapted to delete the data from the auxiliary memory of the second auxiliary component after transmittal of the data to the auxiliary memory of the first auxiliary component.

86. A method for handling auxiliary components, including a first auxiliary component and a second auxiliary component, of a medical system, wherein each auxiliary component is adapted to be coupled to a respective main component, and wherein each auxiliary component comprises a rechargeable battery adapted to power electronic components of the auxiliary component and of the respective main component, each auxiliary component further comprising an auxiliary memory and an auxiliary communication interface, the method comprises receiving a first auxiliary component, receiving a second auxiliary component, transmitting data from the auxiliary memory of the second auxiliary component to the auxiliary memory of the first auxiliary component, charging the rechargeable battery of the second auxiliary component, and providing the first auxiliary component for retrieval after transmitting the data from the auxiliary memory of the second auxiliary component to the auxiliary memory of the first auxiliary component.

87. Method according to item 86, wherein the second auxiliary component is received after receiving the first auxiliary component.

88. Method according to any of items 86-87 further comprising: receiving a third auxiliary component after providing the first auxiliary component for retrieval, transmitting the data from the auxiliary memory of the third auxiliary component to the auxiliary memory of the second auxiliary component, charging the rechargeable battery of the third auxiliary component, and providing the second auxiliary component for retrieval after transmitting the data from the auxiliary memory of the third auxiliary component to the auxiliary memory of the second auxiliary component.

89. Method according to any of items 86-87 further comprising: receiving a third auxiliary component after receiving the first auxiliary component and before receiving the second auxiliary component, charging the rechargeable battery of the third auxiliary component.

90. Method according to any of items 86-89 comprising, after receiving the first auxiliary component, charging the rechargeable battery of the first auxiliary component.

91. Method according to any of items 86-90 comprising receiving a user input at a transmit button, and in response to receiving the user input transmitting the data from the auxiliary memory of the second auxiliary component to the auxiliary memory of the first auxiliary component.

92. Method according to any of items 86-91 comprising storing the data from the auxiliary memory of the second auxiliary component at an external memory.

93. Method according to any of items 86-92 comprising, after transmitting the data to the auxiliary memory of the first auxiliary component, disinfecting the second auxiliary component.

94. Method according to any of items 86-93 comprising, after transmitting the data to the auxiliary memory of the first auxiliary component, validating the data of the auxiliary memory of the first auxiliary component.

95. Method according to any of items 86-94 comprising, after transmitting the data to the auxiliary memory of the first auxiliary component, deleting the data from the auxiliary memory of the second auxiliary component.

96. Medical system comprising auxiliary components, including a first auxiliary component and a second auxiliary component, wherein each auxiliary component is adapted to be coupled to a respective main component, and wherein each auxiliary component comprises an auxiliary memory and a short-range communication circuit and an auxiliary user interface, and wherein the first auxiliary component and second auxiliary component are adapted to transmit, via the short-range communication circuits, data from the auxiliary memory of the second auxiliary component to the auxiliary memory of the first auxiliary component, in response to receiving, at the auxiliary user interface(s) of the first auxiliary component and/or second auxiliary component, one or more user inputs indicative of a request to transmit the data from the auxiliary memory of the second auxiliary component to the auxiliary memory of the first auxiliary component.

97. Medical system according to item 96, wherein the one or more user inputs indicative of a request to transmit the data from the auxiliary memory of the second auxiliary component to the auxiliary memory of the first auxiliary component comprises receiving a first user input at the auxiliary user interface of the first auxiliary component and while or after receiving the first user input at the auxiliary user interface of the first auxiliary component receiving a second user input at the auxiliary user interface of the second auxiliary component.

98. Medical system comprising the handling system according to any of items 71-85 and the first auxiliary component and the second auxiliary component.

101. A medical visualisation device comprising a main component and an auxiliary component, the main component comprising: an image sensor adapted to generate image data indicative of a view from the main component, a light emitter adapted to provide illumination of the view, a main coupling part having one or more main terminals electrically connected to the light emitter and the image sensor, the auxiliary component being couplable to the main component and comprising: an auxiliary coupling part adapted to couple with the main coupling part, the auxiliary coupling part comprising one or more auxiliary terminals adapted to connect to the one or more main terminals of the main coupling part, when the auxiliary coupling part is coupled with the main coupling part, a device processing unit electrically connected to the one or more auxiliary terminals and adapted to receive the image data from the image sensor, when the auxiliary component is coupled to the main component, and encode the image data to provide encoded image data based on the image data, a device transceiver connected to the device processing unit and adapted to communicate with a VPA transceiver of a VPA, the device transceiver being adapted to receive the encoded image data from the device processing unit and transmit the encoded image data using a downstream data channel to the VPA wireless communication module, a battery electrically connected to the one or more auxiliary terminals, the device processing unit and the device wireless communication module, the battery being adapted to power the device processing unit and the device wireless communication module, the battery further being adapted to power the image sensor and light emitter of the main component, when the auxiliary component is coupled to the main component.

102. Medical visualisation device according to item 101, wherein the main component comprises a safety-circuit adapted to preventing excessive current to the light emitter and/or image sensor, and the one or more main terminals being electrically connected to the light emitter and the image sensor via the safety circuit.

103. Medical visualisation device according to any one of items 101-102, wherein the main component comprises a device identifier comprising device identifier information, and wherein the device processing unit is adapted to obtain the device identifier information from the device identifier.

104. Medical visualisation device according to item 103, wherein the device identifier includes an electronically readable memory connected to the one or more main terminals.

105. Medical visualisation device according to any one of items 101-104, wherein the device transceiver comprises a device antenna.

106. Medical visualisation device according to any one of items 101-105 being an endoscope.

107. Medical visualisation device according to any one of items 101-106, wherein the main component comprises a handle and an insertion cord extending from the handle to a distal tip, and wherein the view from the main component is a view from the distal tip of the insertion cord.

108. Medical visualisation device according to item 107, wherein the handle comprises a control button adapted to receive an input in a first input direction, and wherein the touch input in the first input direction causes a bending section of the insertion cord to bend in a first bending direction.

109. Medical visualisation device according to any one of items 101-105 being a laryngoscope.

110. Medical visualisation device according to any one of items 101-109, wherein the device processing unit comprises an image signal processor (ISP), a complex programmable logic device (CPLD), a field-programmable gate array (FPGA), and/or a buffer memory.

111. Medical visualisation device according to any one of items 101-110, wherein the main component is disposable, and the auxiliary component is reusable and adapted to be coupled to a plurality of main components.

112. Medical visualisation device according to any one of items 101-111, wherein the auxiliary component comprises an auxiliary housing, and wherein the device processing unit and the device transceiver are enclosed by the auxiliary housing, the auxiliary housing being fluid-tight to the outside such that the auxiliary component is adapted for wet cleaning, e.g. by immersion in a liquid.

113. Medical visualisation device according to item 112, wherein the auxiliary housing is surface coated with a sealing liquid, e.g. by immersion in the sealing liquid, to make the auxiliary housing fluid-tight.

114. Medical visualisation device according to any one of items 101-113, wherein the main coupling part has a main surface with a main primary engagement member, and the auxiliary coupling part has an auxiliary primary engagement member adapted to engage with the main primary engagement member of the main coupling part to restrict movement of the auxiliary primary engagement member along the main surface.

115. Medical visualisation device according to item 114, wherein the main coupling part comprises a primary surface accommodating exposed portions of the one or more main terminals, and wherein the primary surface is substantially perpendicular to the main surface.

116. Medical visualisation device according to any of items 114-115, wherein the main coupling part has a main secondary engagement member, and the auxiliary coupling part has an auxiliary secondary engagement member adapted to engage with the main secondary engagement member of the main coupling part to restrict movement of the auxiliary secondary engagement member perpendicular to the main surface.

117. Medical visualisation device according to item 116 as dependent on item 115, wherein the primary surface is between the main primary engagement member and the main secondary engagement member.

118. Medical visualisation device according to any one of items 101-117, wherein the auxiliary component comprises a battery indicator indicative of remaining capacity of the battery.

119. An auxiliary component couplable to a main component to form a medical visualisation device, wherein the main component comprises an image sensor adapted to generate image data indicative of a view from the main component, a light emitter adapted to provide illumination of the view, and a main coupling part having one or more main terminals electrically connected to the light emitter and the image sensor, the auxiliary component comprising: an auxiliary coupling part adapted to couple with the main coupling part, the auxiliary coupling part comprising one or more auxiliary terminals adapted to connect to the one or more main terminals of the main coupling part, when the auxiliary coupling part is coupled with the main coupling part, a device processing unit electrically connected to the one or more auxiliary terminals and adapted to receive the image data from the image sensor, when the auxiliary component is coupled to the main component, and encode the image data to provide encoded image data based on the image data, a device transceiver connected to the device processing unit and adapted to communicate with a VPA transceiver of a VPA, the device transceiver being adapted to receive the encoded image data from the device processing unit and transmit the encoded image data using a downstream data channel to the VPA wireless communication module, a battery electrically connected to the one or more auxiliary terminals, the device processing unit and the device wireless communication module, the battery being adapted to power the device processing unit and the device wireless communication module, the battery further being adapted to power the image sensor and light emitter of the main component, when the auxiliary component is coupled to the main component.

120. A medical visualisation system comprising a first medical visualisation device according to any of items 101-118 and the VPA operable to receive image data from the medical visualisation device, the VPA comprising: a first housing, the VPA transceiver adapted to communicate with the device transceiver of the medical visualisation device, the VPA transceiver being adapted to receive encoded image data using the downstream data channel from the device transceiver to the VPA wireless communication module, a VPA controller adapted to receive the encoded image data from the VPA wireless communication module, decode the encoded image data, and cause a display to display a live representation of the image data.

121. Medical visualisation system according to item 120, wherein the VPA comprises the display, e.g. accommodated in the first housing.

122. Medical visualisation system according to any of items 120-121, wherein the VPA transceiver comprises a VPA antenna, wherein the VPA antenna is arranged external to the first housing.

123. Medical visualisation system according to item 122, wherein the VPA antenna is adapted to be positioned at a distance from the first housing of more than 2 meters.

124. Medical visualisation system according to any of items 122-123, wherein the VPA antenna is adapted to be positioned above an operating setting in an operating room, such as at a ceiling of the operating room.

125. Medical visualisation system according to any of items 122-124, wherein the VPA antenna is positioned above the first housing.

126. Medical visualisation system according to any of items 122-125, at least as dependent on item 5, wherein the VPA antenna and the device antenna is positioned with line of sight there between.

127. Medical visualisation system according to any of items 120-126, wherein the VPA comprises a component socket adapted to engage with the auxiliary component.

128. Medical visualisation system according to item 127, wherein the VPA comprises a VPA charging circuit adapted to charge the battery, when the auxiliary component is engaged with the component socket.

129. Medical visualisation system according to item 128, wherein the VPA charging circuit comprises exposed charging terminals to contact corresponding exposed charging terminals of the auxiliary component, the one or more auxiliary terminals may comprise the charging terminals of the auxiliary component.

130. Medical visualisation system according to item 128, wherein the VPA charging circuit comprises one or more inductive charging coils adapted to inductively transfer power to one or more inductive receiver coils of the auxiliary component.

131. Medical visualisation system according to any of items 127-130, wherein the VPA controller is adapted to pair the device transceiver with the VPA transceiver when the auxiliary component is engaged with the component socket.

132. Medical visualisation system according to item 131, wherein the component socket comprises exposed pairing terminals to contact corresponding exposed pairing terminals of the auxiliary component, the one or more auxiliary terminals may comprise the pairing terminals of the auxiliary component.

133. Medical visualisation system according to any of items 131-132, wherein the VPA comprises a short-range pairing circuit adapted to wirelessly communicate with a corresponding short-range pairing circuit of the auxiliary component.

134. Medical visualisation system according to any of items 120-133, wherein the VPA comprises a VPA coupling part adapted to couple with the main coupling part, the VPA coupling part comprising one or more VPA terminals adapted to connect to the one or more main terminals of the main coupling part when the VPA coupling part is coupled with the main coupling part, and wherein the VPA controller is electrically connected to the one or more VPA terminals and adapted to receive the image data from the image sensor and cause the display to display a live representation of the image data.

135. Medical visualisation system according to item 134, wherein the VPA comprises one or more flexible VPA wires, wherein the one or more VPA terminals are arranged at a distal end of the one or more flexible VPA wires, and wherein the one or more VPA terminals are electrically connected to the VPA controller through the one or more flexible VPA wires.

136. Medical visualisation system according to item 135, wherein the one or more flexible VPA wires and the one or more VPA coupling terminals are enclosed in a sealed package, and a coupling plug coupled to a proximal end of the one or more flexible VPA wires is arranged outside the sealed package, and the VPA comprises a coupling socket for receiving the coupling plug.

137. Medical visualisation system according to any of items 120-135, wherein the main component comprises one or more flexible device wires extending between the main coupling part and a handle of the main component, and wherein the one or more main terminals are electrically connected to the light emitter and the image sensor through the one or more flexible device wires.

138. Medical visualisation system according to any of items 120-137 comprising a second medical visualisation device, the second medical visualisation comprising a main component comprising: an image sensor adapted to generate image data indicative of a view from the main component of the second medical visualisation device, a light emitter adapted to provide illumination of the view, and a main coupling part having one or more main terminals electrically connected to the light emitter and the image sensor, wherein the auxiliary component of the first medical visualisation device is couplable to the main component of the second medical visualisation device.

139. Medical visualisation system according to any of items 120-137 comprising a second medical visualisation device according to any of items 1-18, e.g. wherein the first medical visualisation device and the second medical visualisation device are different.

140. Medical visualisation system according to item 139, wherein the auxiliary component of the first medical visualisation device and the auxiliary component of the second medical visualisation device is the same.

141. Medical visualisation system according to any of items 138-140, wherein the first medical visualisation device is configured for a first clinical purpose and the second medical visualisation device is configured for a second clinical purpose.

142. Medical visualisation system according to any of items 138-141, wherein the image sensor of the first medical visualisation device is a first image sensor type and the image sensor of the second medical visualisation device is a second image sensor type.

143. Medical visualisation system according to any of items 138-142, wherein the main component of the second visualisation device comprises a safety-circuit adapted to prevent excessive current to the light emitter and/or image sensor of the second visualisation device, and the one or more main terminals of the second visualisation device being electrically connected to the light emitter and the image sensor via the safety circuit.

151. A medical visualisation system comprising a main component and an auxiliary component, the main component comprising: an image sensor adapted to generate image data indicative of a view from the main component, a light emitter adapted to provide illumination of the view, and a main coupling part having one or more main terminals electrically connected to the light emitter and the image sensor, the auxiliary component being couplable to the main component and comprising: an auxiliary coupling part adapted to couple with the main coupling part, the auxiliary coupling part comprising one or more auxiliary terminals adapted to connect to the one or more main terminals of the main coupling part, when the auxiliary coupling part is coupled with the main coupling part, a device processing unit electrically connected to the one or more auxiliary terminals and adapted to receive the image data from the image sensor, when the auxiliary component is coupled to the main component, and encode the image data to provide encoded image data based on the image data, a device transceiver connected to the device processing unit and adapted to communicate with a VPA transceiver of a VPA, the device transceiver being adapted to receive the encoded image data from the device processing unit and transmit the encoded image data using a downstream data channel to the VPA wireless communication module, and a battery electrically connected to the one or more auxiliary terminals, the device processing unit and the device wireless communication module, the battery being adapted to power the device processing unit and the device wireless communication module, the battery further being adapted to power the image sensor and light emitter of the main component, when the auxiliary component is coupled to the main component.

152. Medical visualisation system according to item 151, wherein the auxiliary component comprises a wearing element adapted to attach the auxiliary component to an operator of the medical visualisation system.

153. Medical visualisation system according to any of items 151-152, wherein the main coupling part comprises one or more main magnetic elements, and the auxiliary coupling part comprises one or more auxiliary magnetic elements, the one or more main magnetic elements and the one or more auxiliary magnetic elements being adapted to align the one or more auxiliary terminals with the one or more main terminals and couple the auxiliary coupling part and the main coupling part.

154. Medical visualisation system according to item 153, wherein the one or more main magnetic elements comprises a first main magnetic element having a primary polarity and a second main magnetic element having a secondary polarity being opposite the primary polarity, and wherein the one or more auxiliary magnetic elements comprises a first auxiliary magnetic element having the secondary polarity and a second auxiliary magnetic element having the primary polarity.

155. Medical visualisation system according to any one of items 151-154, wherein the main coupling part comprises a safety-circuit adapted to prevent excessive current to the light emitter and/or image sensor, and the one or more main terminals being electrically connected to the light emitter and the image sensor via the safety circuit.

156. Medical visualisation system according to any any one of items 151-155, wherein the main coupling part comprises a device identifier indicative of device identifier information, and wherein the device processing unit is adapted to obtain the device identifier information from the device identifier.

157. Medical visualisation system according to item 156, wherein the device identifier includes an electronically readable memory connected to the one or more main terminals.

158. Medical visualisation system according to any one of items 151-157, wherein the main component comprises a handle.

159. Medical visualisation system according to item 158, wherein the main component comprises one or more flexible wires extending between the main coupling part and the handle, and wherein the one or more main terminals are electrically connected to the light emitter and the image sensor through the one or more flexible wires.

160. Medical visualisation system according to any of items 158-159, wherein the main component comprises an insertion cord extending from the handle to a distal tip, and wherein the view from the main component is a view from the distal tip of the insertion cord.

161. Medical visualisation system according to any one of items 151-161, comprising the VPA, the VPA comprising: a first housing, the VPA transceiver adapted to communicate with the device wireless communication module, the VPA transceiver being adapted to receive the encoded image data from the device wireless communication module, a VPA controller electrically connected to the VPA transceiver and adapted to receive the encoded image data from the VPA wireless communication module, decode the encoded image data, and cause a display to display a live representation of the image data, and a VPA coupling part comprising one or more VPA terminals electrically connected to the VPA controller.

162. Medical visualisation system according to item 161, wherein the VPA comprises the display, e.g. accommodated in the first housing.

163. Medical visualisation system according to any of items 161-162, wherein the VPA coupling part is adapted to couple with the main coupling part, and the one or more VPA terminals are adapted to connect to the one or more main terminals of the main coupling part, and the VPA controller being adapted to, when the VPA coupling part is coupled with the main coupling part, receive the image data from the image sensor and cause the display to display a live representation of the image data.

164. Medical visualisation system according to any of items 161-163, wherein the auxiliary component comprises a secondary auxiliary coupling part having one or more secondary auxiliary terminals, and the VPA coupling part is adapted to couple with the secondary auxiliary coupling part, and the one or more VPA terminals are adapted to connect to the one or more secondary auxiliary terminals of the secondary auxiliary coupling part, and the VPA controller being adapted to, when the VPA coupling part is coupled with the secondary auxiliary coupling part, receive the image data and/or the encoded image data from the auxiliary component and cause the display to display a live representation of the image data.

165. Medical visualisation system according to any of items 161-164, wherein the VPA coupling part comprises one or more flexible VPA wires, wherein the one or more VPA terminals is arranged at a distal end of the one or more flexible VPA wires, and wherein the one or more VPA terminals are electrically connected to the VPA controller through the one or more flexible VPA wires.

166. Medical visualisation system according to item 165, wherein the one or more flexible VPA wires and the one or more VPA terminals are enclosed in a sealed package, and a plug coupled to a proximal end of the one or more flexible VPA wires is arranged outside the sealed package, and the VPA comprising a socket for receiving the plug.

167. Medical visualisation system according to any of items 161-166, wherein the VPA controller is adapted to perform an electronic analysis of the VPA coupling part at predetermined intervals, and in accordance with registering a non-working condition of the VPA coupling part, the VPA controller activates a warning indication to prompt the user to replace the VPA coupling part.

168. Medical visualisation system according to any one of items 151-168, comprising a plurality of medical visualisation devices including a first medical visualisation device and a second medical visualisation device, wherein the main component forms part of the first medical visualisation device and the second medical visualisation device comprises another main component comprising: an image sensor adapted to generate image data indicative of a view from the main component of the second medical visualisation device, a light emitter adapted to provide illumination of the view, and a main coupling part having one or more main terminals electrically connected to the light emitter and the image sensor.

169. Medical visualisation system according to item 168, wherein the auxiliary component is couplable to the main component of the second medical visualisation device, and the main coupling part of the second medical visualisation device being adapted to couple with the auxiliary coupling part of the auxiliary component.

170. Medical visualisation system according to any one of items 168-169, wherein the first medical visualisation device is configured for a first clinical purpose and the second medical visualisation device is configured for a second clinical purpose.

171. Medical visualisation system according to any of items 168-170, wherein the image sensor of the first medical visualisation device is a first image sensor type and the image sensor of the second medical visualisation device is a second image sensor type.

172. Medical visualisation system according to any of items 168-171, wherein the main component of the second visualisation device comprises a safety-circuit adapted to prevent excessive current to the light emitter and/or image sensor of the second visualisation device, and the one or more main terminals of the second visualisation device being electrically connected to the light emitter and the image sensor via the safety circuit.

173. An auxiliary component couplable to a main component of a medical visualisation device, wherein the main component comprises an image sensor adapted to generate image data indicative of a view from the main component, a light emitter adapted to provide illumination of the view, and a main coupling part having one or more main terminals electrically connected to the light emitter and the image sensor, the auxiliary component comprising: an auxiliary coupling part adapted to couple with the main coupling part, the auxiliary coupling part comprising one or more auxiliary terminals adapted to connect to the one or more main terminals of the main coupling part, when the auxiliary coupling part is coupled with the main coupling part, a device processing unit electrically connected to the one or more auxiliary terminals and adapted to receive the image data from the image sensor, when the auxiliary component is coupled to the main component, and encode the image data to provide encoded image data based on the image data, a device transceiver connected to the device processing unit and adapted to communicate with a VPA transceiver of a VPA, the device transceiver being adapted to receive the encoded image data from the device processing unit and transmit the encoded image data using a downstream data channel to the VPA wireless communication module, a battery electrically connected to the one or more auxiliary terminals, the device processing unit and the device wireless communication module, the battery being adapted to power the device processing unit and the device wireless communication module, the battery further being adapted to power the image sensor and light emitter of the main component, when the auxiliary component is coupled to the main component.

174. Auxiliary component according to item 173 comprising a wearing element adapted to attach the auxiliary component to an operator.

Throughout the description, the use of the terms "first", "second", "third", "fourth", "primary", "secondary", "tertiary" etc. does not imply any particular order or importance but are included to identify individual elements. Furthermore, the labelling of a first element does not imply the presence of a second element and vice versa.

The invention claimed is:
1. A medical visualisation system comprising:
a main component including an image sensor and a light emitter, the main component being configured to sense a view with the image sensor;
a first auxiliary component configured to physically couple and decouple with the main component and, if coupled to the main component, transmit image data based on the view, the first auxiliary component comprising a controller, a first memory, a high frequency wireless transceiver, a short-range communication circuit, and a first rechargeable battery;
a second auxiliary component configured to physically couple and decouple with the main component and, if coupled to the main component, transmit image data based on the view, the second auxiliary component comprising a controller, a second memory, a high frequency wireless transceiver, a short-range communication circuit, and a second rechargeable battery, the second memory having embedded therein data; and a video processing apparatus comprising a high frequency wireless transceiver configured to establish an image data communication channel with the high frequency wireless transceiver of the first auxiliary component or with the high frequency wireless transceiver of the second auxiliary component and to receive the image data via the image data communication channel,
wherein the first auxiliary component is configured to, based on the data, cause adjustment of one or more components of (a) the main component and/or (b) the video processing apparatus.

2. The medical visualisation system of claim 1, wherein the first auxiliary component is configured to cause adjustment of one or more components of the video processing apparatus by sending the data to the video processing apparatus.

3. The medical visualisation system of claim 2, wherein the data comprises one or more of operator data, patient data, operator setup data, and/or procedure data.

4. The medical visualisation system of claim 1, wherein the first auxiliary component is configured to receive the data and to cause adjustment of settings of the image sensor and/or the light emitter.

5. The medical visualisation system of claim 4, wherein the first auxiliary component is configured to establish a short-range wireless communication channel with the second auxiliary component using their respective short-range communication circuits, and to receive the data using the short-range wireless communication channel.

6. The medical visualisation system of claim 1, wherein the first auxiliary component is a wearable device.

7. The medical visualisation system of claim 1, wherein the image data is encoded to conform to a high frequency communication standard.

8. The medical visualisation system of claim 1, the medical visualisation system further comprising magnetic coupling means to physically couple and decouple the first auxiliary component to the main component or to the video processing apparatus.

9. The medical visualisation system of claim 8, wherein the first auxiliary component is a wearable device.

10. The medical visualisation system of claim 9, wherein the magnetic coupling means are configured to secure the first auxiliary component to the video processing apparatus, the first auxiliary component and the video processing apparatus comprising terminals configured to establish an electrical connection, the video processing apparatus comprising a charging circuit, and the electrical connection configured to charge the first rechargeable battery.

11. The medical visualisation system of claim 10, wherein at least one of the terminals is configured to establish an electrical communication channel between the video processing apparatus and the first auxiliary component, the electrical communication channel being configured to transfer the data from the video processing apparatus to the first auxiliary component.

12. The medical visualisation system of claim 1, the medical visualisation system further comprising a handling station including a charging circuit to charge the first rechargeable battery, and wherein the first auxiliary component is configured to receive the data while the first auxiliary component is coupled to the handling station.

13. The medical visualisation system of claim 12, wherein the handling station comprises non-wireless means to transfer the data from the second auxiliary component to the first auxiliary component while the first auxiliary component and the second auxiliary component are coupled to the handling station.

14. The medical visualisation system of claim 12, wherein the handling station comprises a disinfection chamber configured to disinfect the second auxiliary component after transmission of the data to the first auxiliary component is completed.

15. The medical visualisation system of claim 1, wherein the video processing apparatus is configured to cause presentation of images on a display, the images being based on the image data.

16. The medical visualisation system of claim 1, wherein the main component comprises a main component coupling part and the first auxiliary component comprises a first auxiliary component coupling part, wherein the main component coupling part and the first auxiliary component coupling part comprise corresponding engagement members to mechanically couple and decouple the main component coupling part and the first auxiliary component coupling part.

17. The medical visualisation system of claim 16, wherein the main component coupling part comprises electrical terminals and the first auxiliary component coupling part comprises corresponding electrical terminals configured to electrically connect with the electrical terminals of the main component coupling part to transmit the image data when the main component is mechanically coupled with the first auxiliary component.

18. The medical visualisation system of claim 16, wherein the video processing apparatus (VPA) comprises a VPA coupling part configured to physically couple and decouple with the main component coupling part.

19. The medical visualisation system of claim 15, wherein the video processing apparatus comprises the display.

20. The medical visualisation system of claim 1, further comprising a charging station, the charging station comprising a controller, a buss, a first handling system communication interface and a second handling system communication interface, the first handling system communication interface and the second handling system communication interface electrically connected via the bus to the controller, the first handling system communication interface configured to physically couple and decouple with the first auxiliary component, the second handling system communication interface configured to physically couple and decouple with the second auxiliary component, and the controller configured to cause transfer of the data between the first auxiliary component and the second auxiliary component.

* * * * *